(12) United States Patent
Yamaguchi et al.

(10) Patent No.: US 12,096,690 B2
(45) Date of Patent: Sep. 17, 2024

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Tomoya Yamaguchi, Kanagawa (JP); Hideko Yoshizumi, Kanagawa (JP); Hiromitsu Kido, Kanagawa (JP); Airi Ueda, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 17/893,355

(22) Filed: Aug. 23, 2022

(65) Prior Publication Data

US 2023/0027613 A1    Jan. 26, 2023

Related U.S. Application Data

(63) Continuation of application No. 16/249,209, filed on Jan. 16, 2019, now Pat. No. 11,462,696.

(30) Foreign Application Priority Data

Jan. 19, 2018    (JP) .................... 2018-007073

(51) Int. Cl.
*H01L 51/00*     (2006.01)
*C07D 491/048*   (2006.01)
(Continued)

(52) U.S. Cl.
CPC ..... *H10K 85/6576* (2023.02); *C07D 491/048* (2013.01); *H10K 85/657* (2023.02);
(Continued)

(58) Field of Classification Search
None
See application file for complete search history.

(56) References Cited

U.S. PATENT DOCUMENTS 7,175,922 B2    2/2007    Jarikov et al.
7,183,010 B2    2/2007    Jarikov
(Continued)

FOREIGN PATENT DOCUMENTS

CN    104136430 A    11/2014
CN    107163057 A     9/2017
(Continued)

OTHER PUBLICATIONS

Chinese Office Action (Application No. 201910053913.2) Dated Nov. 9, 2022.
(Continued)

*Primary Examiner* — Jay Yang
(74) *Attorney, Agent, or Firm* — Husch Blackwell LLP

(57) ABSTRACT

A novel organic compound is provided. That is, a novel organic compound that is effective in improving element characteristics and reliability is provided. The organic compound is represented by General Formula (G1) having a dibenzobenzofuroquinoxaline skeleton or a dibenzobenzothienoquinoxaline skeleton.

(Continued)

(G1)

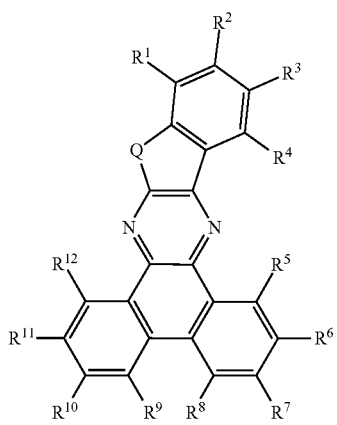

In General Formula (G1), Q represents O or S, at least one of $R^1$ to $R^{12}$ represents a first group having a substituted or unsubstituted condensed aromatic ring or condensed heteroaromatic ring having 3 to 30 carbon atoms, and the other or others of $R^1$ to $R^{12}$ each independently represent any one of hydrogen, a halogeno group, a hydroxy group, an amino group, a nitro group, and a group having 1 to 50 carbon atoms.

14 Claims, 15 Drawing Sheets

(51) Int. Cl.
*H10K 85/60* (2023.01)
*H10K 50/11* (2023.01)
*H10K 50/15* (2023.01)
*H10K 50/16* (2023.01)
*H10K 50/17* (2023.01)
*H10K 50/81* (2023.01)
*H10K 50/82* (2023.01)
*H10K 50/842* (2023.01)
*H10K 59/38* (2023.01)
*H10K 71/00* (2023.01)
*H10K 71/16* (2023.01)
*H10K 71/60* (2023.01)
*H10K 101/10* (2023.01)
*H10K 101/30* (2023.01)
*H10K 101/40* (2023.01)
*H10K 102/00* (2023.01)
*H10K 102/10* (2023.01)

(52) U.S. Cl.
CPC ..... *H10K 85/6572* (2023.02); *H10K 85/6574* (2023.02); *H10K 50/11* (2023.02); *H10K 50/15* (2023.02); *H10K 50/16* (2023.02); *H10K 50/17* (2023.02); *H10K 50/171* (2023.02); *H10K 50/81* (2023.02); *H10K 50/82* (2023.02); *H10K 50/8426* (2023.02); *H10K 59/38* (2023.02); *H10K 71/00* (2023.02); *H10K 71/16* (2023.02); *H10K 71/60* (2023.02); *H10K 2101/10* (2023.02); *H10K 2101/30* (2023.02); *H10K 2101/40* (2023.02); *H10K 2102/103* (2023.02); *H10K 2102/311* (2023.02); *H10K 2102/351* (2023.02)

(56) References Cited

U.S. PATENT DOCUMENTS

| | | | |
|---|---|---|---|
| 7,332,857 B2 | 2/2008 | Seo et al. | |
| 7,597,967 B2 | 10/2009 | Kondakova et al. | |
| 7,906,226 B2 | 3/2011 | Matsuura et al. | |
| 7,993,760 B2 | 8/2011 | Komori et al. | |
| 8,034,465 B2 | 10/2011 | Liao et al. | |
| 8,105,701 B2 | 1/2012 | Matsuura et al. | |
| 8,274,214 B2 | 9/2012 | Ikeda et al. | |
| 8,470,455 B2 | 6/2013 | Matsuura et al. | |
| 8,853,680 B2 | 10/2014 | Yamazaki et al. | |
| 8,963,127 B2 | 2/2015 | Pieh et al. | |
| 8,981,355 B2 | 3/2015 | Seo | |
| 8,993,129 B2 | 3/2015 | Endo et al. | |
| 8,994,263 B2 | 3/2015 | Shitagaki et al. | |
| 9,054,317 B2 | 6/2015 | Monkman et al. | |
| 9,079,879 B2 | 7/2015 | Kadoma et al. | |
| 9,159,942 B2 | 10/2015 | Seo et al. | |
| 9,175,213 B2 | 11/2015 | Seo et al. | |
| 9,356,250 B2 | 5/2016 | Ohsawa et al. | |
| 9,604,928 B2 | 3/2017 | Shitagaki et al. | |
| 9,695,158 B2 | 7/2017 | Inoue et al. | |
| 9,899,608 B2 | 2/2018 | Kadoma et al. | |
| 10,224,490 B2 | 3/2019 | Kadoma et al. | |
| 10,734,589 B2 | 8/2020 | Suzuki et al. | |
| 11,121,326 B2 | 9/2021 | Suzuki et al. | |
| 11,530,224 B2 | 12/2022 | Parham et al. | |
| 11,643,414 B2 | 5/2023 | Parham et al. | |
| 2003/0175553 A1 | 9/2003 | Thompson et al. | |
| 2005/0048310 A1 | 3/2005 | Cocchi et al. | |
| 2005/0221116 A1 | 10/2005 | Cocchi et al. | |
| 2006/0134464 A1 | 6/2006 | Nariyuki | |
| 2006/0210828 A1 | 9/2006 | Nakayama et al. | |
| 2007/0090756 A1 | 4/2007 | Okada et al. | |
| 2012/0217487 A1 | 8/2012 | Yamazaki et al. | |
| 2012/0248968 A1* | 10/2012 | Ogiwara ............... | H10K 50/11 313/504 |
| 2013/0165653 A1 | 6/2013 | Inoue et al. | |
| 2014/0110686 A1 | 4/2014 | Fujita et al. | |
| 2014/0117331 A1 | 5/2014 | Kim et al. | |
| 2014/0291645 A1 | 10/2014 | Inoue et al. | |
| 2015/0041784 A1 | 2/2015 | Shizu et al. | |
| 2015/0069352 A1 | 3/2015 | Kim et al. | |
| 2016/0141515 A1 | 5/2016 | Hayama et al. | |
| 2016/0163997 A1 | 6/2016 | Noh et al. | |
| 2016/0322569 A1 | 11/2016 | Yen | |
| 2017/0186971 A1 | 6/2017 | Kanamoto et al. | |
| 2017/0294594 A1 | 10/2017 | Inoue et al. | |
| 2020/0024282 A1* | 1/2020 | Parham ............... | H10K 85/6576 |
| 2023/0117837 A1 | 4/2023 | Parham et al. | |

FOREIGN PATENT DOCUMENTS

| | | |
|---|---|---|
| CN | 109689658 A | 4/2019 |
| DE | 11 2012 005 364 T5 | 10/2014 |
| EP | 1 202 608 A2 | 5/2002 |
| EP | 2 363 398 A1 | 9/2011 |
| EP | 2 808 323 A1 | 12/2014 |
| JP | 2004-241374 A | 8/2004 |
| JP | 2008-288344 A | 11/2008 |
| JP | 2010-182699 A | 8/2010 |
| JP | 2011-201869 A | 10/2011 |
| JP | 2013-256490 A | 12/2013 |
| JP | 2015-227324 A | 12/2015 |
| JP | 2016-135775 A | 7/2016 |
| JP | 2018-188418 A | 11/2018 |
| JP | 2019-521081 | 7/2019 |
| JP | 2019-532951 | 11/2019 |
| JP | 2019-532952 | 11/2019 |
| KR | 2015-0009512 A | 1/2015 |
| KR | 2015-0027443 A | 3/2015 |
| KR | 2015-0132993 A | 11/2015 |
| KR | 2016-0018458 A | 2/2016 |
| KR | 2016-0068641 A | 6/2016 |
| KR | 2017-0100283 A | 9/2017 |
| KR | 2019-0059949 A | 5/2019 |

(56) References Cited

FOREIGN PATENT DOCUMENTS

| TW | 201350558 | | 12/2013 |
|---|---|---|---|
| WO | WO 2013/172255 | A1 | 11/2013 |
| WO | WO 2017/186760 | A1 | 11/2017 |
| WO | WO-2018/033820 | | 2/2018 |
| WO | WO 2018/060218 | A1 | 4/2018 |
| WO | WO-2018060307 | A1 * | 4/2018 |

OTHER PUBLICATIONS

Chen, F et al., "Triplet Exciton Confinement in Phosphorescent Polymer Light-Emitting Diodes," Applied Physics Letters, Feb. 17, 2003, vol. 82, No. 7, pp. 1006-1008.

Tokito, S. et al., "Confinement of Triplet Energy on Phosphorescent Molecules for Highly-Efficient Organic Blue-Light-Emitting Devices," Applied Physics Letters, Jul. 21, 2003, vol. 83, No. 3, pp. 569-571.

Itano, K. et al., "Exciplex Formation at the Organic Solid-State Interface: Yellow Emission in Organic Light-Emitting Diodes Using Green-Fluorescent tris(8-quinolinolato)aluminum and Hole-Transporting Molecular Materials with Low Ionization Potentials," Applied Physics Letters, Feb. 9, 1998, vol. 72, No. 6, pp. 636-638.

Endo, A. et al., "Efficient Up-Conversion of Triplet Excitons Into a Singlet State and Its Application for Organic Light Emitting Diodes," Applied Physics Letters, Feb. 24, 2011, vol. 98, No. 8, pp. 083302-1-083302-3.

Kondakova, M. et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.

Hino, Y et al., "Red Phosphorescent Organic Light-Emitting Diodes Using Mixture System of Small-Molecule and Polymer Host," Japanese Journal of Applied Physics, Apr. 21, 2005, vol. 44, No. 4B, pp. 2790-2794.

Su, S. et al., "RGB Phosphorescent Organic Light-Emitting Diodes by Using Host Materials with Heterocyclic Cores: Effect of Nitrogen Atom Orientations," Chemistry of Materials, 2011, vol. 23, No. 2, pp. 274-284.

Tsuboyama, A. et al., "Homoleptic Cyclometalated Iridium Complexes with Highly Efficient Red Phosphorescence and Application to Organic Light-Emitting Diode," Journal of the American Chemical Society, 2003, vol. 125, No. 42, pp. 12971-12979.

Gong, X. et al., "Phosphorescence from Iridium Complexes Doped into Polymer Blends," Journal of Applied Physics, Feb. 1, 2004, vol. 95, No. 3, pp. 948-953.

Lee, J. et al., "Stabilizing the Efficiency of Phosphorescent Organic Light-Emitting Diodes," SPIE Newsroom, Apr. 21, 2008, pp. 1-3.

Camaggi, C. et al., "Radical Annulations with Nitriles: Novel Cascade Reactions of Cyano-Substituted Alkyl and Sulfanyl Radicals with Isonitriles," TETRAHEDRON, May 21, 1998, vol. 54, No. 21, pp. 5587-5598.

Yersin, H. et al., Highly Efficient OLEDs with Phosphorescent Materials, 2008, pp. 1-97,283-309, Wiley-VCH Verlag GmbH & Co.

Tokito, S. et al., "Improvement in Performance by Doping," Organic EL Display, Aug. 20, 2004, pp. 67-99, Ohmsha.

Jeon, W. et al., "Ideal Host and Guest System in Phosphorescent OLEDs," Organic Electronics, 2009, vol. 10, pp. 240-246, ELSEVIER.

Rausch, A. et al., "Matrix Effects on the Triplet State of the OLED Emitter Ir(4,6-dFppy)2(pic)(FIrpic): Investigations by High-Resolution Optical Spectroscopy," Inorganic Chemistry, 2009, vol. 48, No. 5, pp. 1928-1937.

Zhao, Q. et al., "Synthesis and Photophysical, Electrochemical, and Electrophosphorescent Properties of a Series of Iridium(III) Complexes Based on Quinoline Derivatives and Different β-Diketonate Ligands", ORGANOMETALLICS, Jun. 14, 2006, vol. 25, No. 15, pp. 3631-3638.

Park, Y. et al., "Efficient Triplet Harvesting by Fluorescent Molecules Through Exciplexes for High Efficiency Organic Light-Emitting Diodes," Applied Physics Letters, Apr. 18, 2013, vol. 102, No. 15, pp. 153306-1-153306-5.

Galvez, C. et al., "New Routes to Condensed Thiophene Ring Systems from ortho-Diaminothlophene Derivatives," Journal of Chemical Research, Sep. 1, 1985, vol. 1985, No. 9, pp. 296-297.

German Office Action (Application No. 102019200635.3) Dated Jul. 3, 2023.

* cited by examiner

4000

4200

ORGANIC COMPOUND, LIGHT-EMITTING ELEMENT, LIGHT-EMITTING DEVICE, ELECTRONIC DEVICE, AND LIGHTING DEVICE

This application is a continuation of copending U.S. application Ser. No. 16/249,209, filed on Jan. 16, 2019 which is incorporated herein by reference.

BACKGROUND OF THE INVENTION

1. Field of the Invention

One embodiment of the present invention relates to an organic compound, a light-emitting element, a light-emitting device, an electronic device, and a lighting device. Note that one embodiment of the present invention is not limited thereto. That is, one embodiment of the present invention relates to an object, a method, a manufacturing method, or a driving method. One embodiment of the present invention relates to a process, a machine, manufacture, or a composition of matter. Specific examples include a semiconductor device, a display device, a liquid crystal display device, and the like.

2. Description of the Related Art

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

[Patent Document 1] Japanese Published Patent Application No. 2010-182699

SUMMARY OF THE INVENTION

In development of light-emitting elements, organic compounds used in the light-emitting element are very important to improve the characteristics and reliability. Thus, in one embodiment of the present invention, a novel organic compound is provided. That is, a novel organic compound that is effective in improving element characteristics and reliability is provided. In another embodiment of the present invention, a novel organic compound that can be used in a light-emitting element is provided. In another embodiment of the present invention, a novel organic compound that can be used in an EL layer of a light-emitting element is provided. In another embodiment of the present invention, a highly efficient, highly reliable, and novel light-emitting element using a novel organic compound of one embodiment of the present invention is provided. In another embodiment of the present invention, a novel light-emitting device, a novel electronic device, or a novel lighting device is provided. Note that the description of these objects does not disturb the existence of other objects. In one embodiment of the present invention, there is not necessarily a need to achieve all the objects. Other objects will be apparent from and can be derived from the description of the specification, the drawings, the claims, and the like.

One embodiment of the present invention is an organic compound represented by General Formula (G1) below.

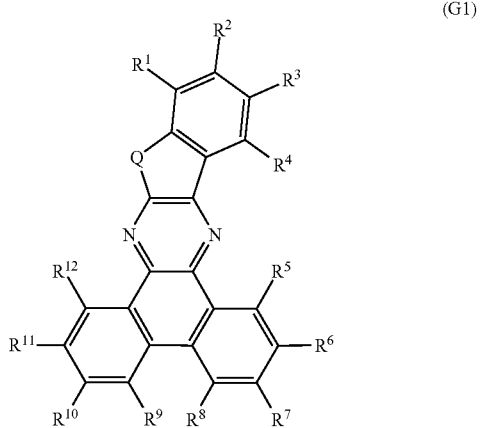

(G1)

In General Formula (G1), Q represents O or S, at least one of $R^1$ to $R^{12}$ represents a first group having a substituted or unsubstituted condensed aromatic ring or condensed heteroaromatic ring having 3 to 30 carbon atoms, and the other or others of $R^1$ to $R^{12}$ each independently represent any one of hydrogen, a halogeno group, a hydroxy group, an amino group, a nitro group, and a group having 1 to 50 carbon atoms.

Another embodiment of the present invention is an organic compound represented by General Formula (G1) below.

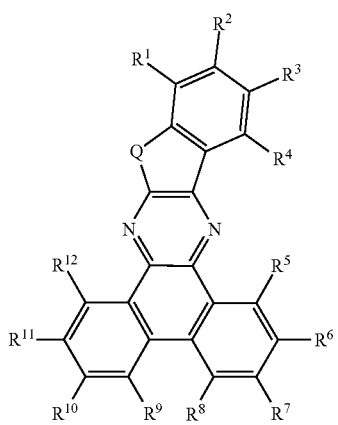
(G1)

In General Formula (G1), Q represents O or S, at least one of $R^1$ to $R^{12}$ represents a first group having a substituted or unsubstituted hole-transport skeleton having 3 to 30 carbon atoms in a ring, and the other or others of $R^1$ to $R^{12}$ each independently represent any one of hydrogen, a halogeno group, a hydroxy group, an amino group, a nitro group, and a group having 1 to 50 carbon atoms.

Another embodiment of the present invention is an organic compound represented by General Formula (G1) below.

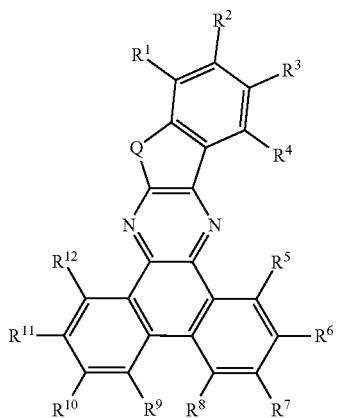
(G1)

In General Formula (G1), Q represents O or S, at least one of $R^1$ to $R^{12}$ represents a first group having any one of a fluorene skeleton, a phenanthrene skeleton, a triphenylene skeleton, a naphthalene skeleton, a dibenzothiophene skeleton, a dibenzofuran skeleton, and a carbazole skeleton, and the other or others of $R^1$ to $R^{12}$ each independently represent any one of hydrogen, a halogeno group, a hydroxy group, an amino group, a nitro group, and a group having 1 to 50 carbon atoms.

In each of the above embodiments, the first group preferably has 3 to 100 carbon atoms in total.

Another embodiment of the present invention is an organic compound represented by General Formula (G1) below.

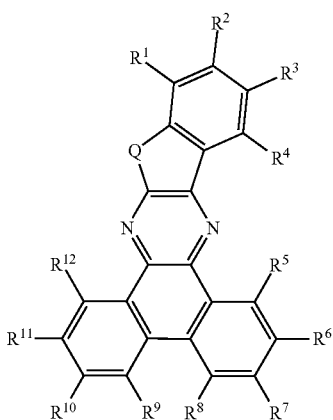
(G1)

In General Formula (G1), Q represents O or S, at least one of $R^1$ to $R^{12}$ represents a first group to which any one of structures represented by General Formulae (A-1) to (A-21) below is bonded through a substituted or unsubstituted arylene group having 6 to 24 carbon atoms in a ring or a substituted or unsubstituted heteroarylene group having 3 to 24 carbon atoms in a ring, and the other or others of $R^1$ to $R^{12}$ each independently represent any one of hydrogen, a halogeno group, a hydroxy group, an amino group, a nitro group, and a group having 1 to 50 carbon atoms.

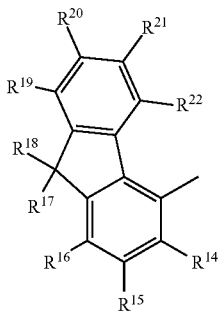
(A-1)

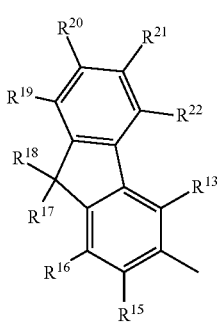
(A-2)

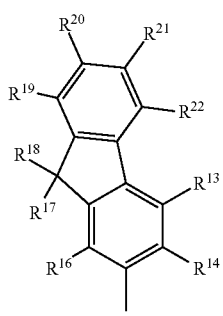
(A-3)
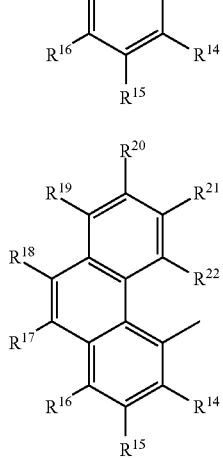
(A-4)
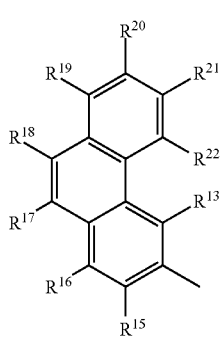
(A-5)
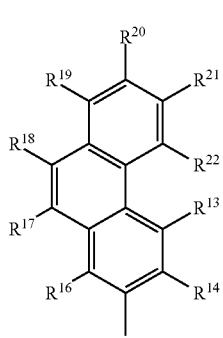
(A-6)
(A-7)
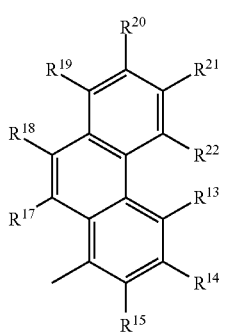
(A-8)
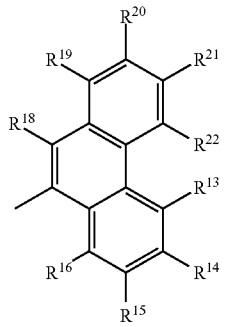
(A-9)
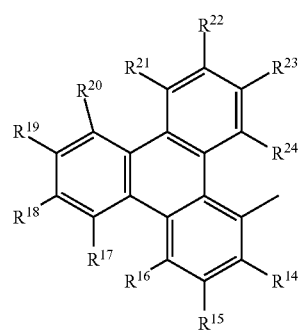
(A-10)
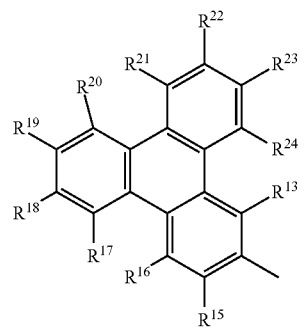
(A-11)
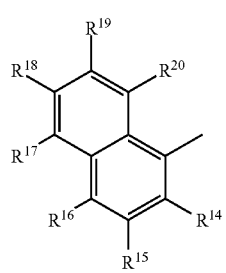
(A-12)

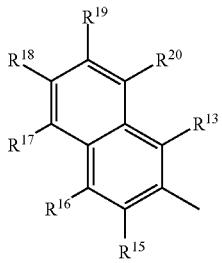
(A-13)

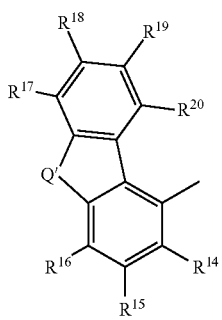
(A-14)

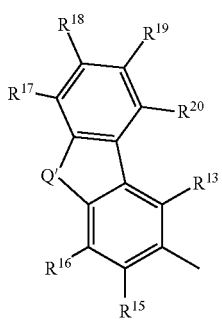
(A-15)

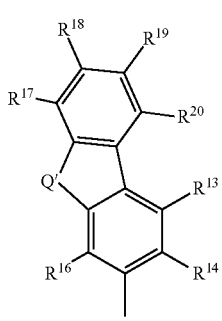
(A-16)

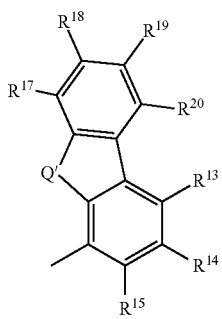
(A-17)

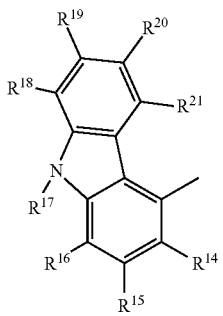
(A-18)

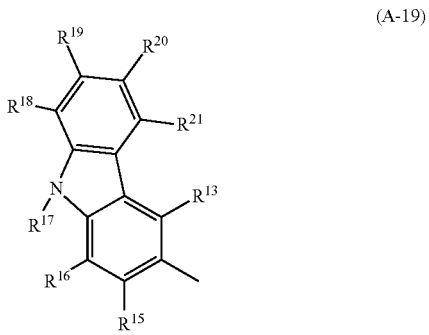
(A-19)

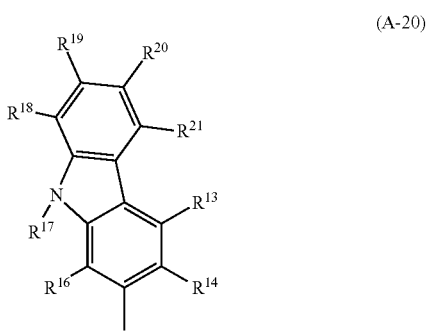
(A-20)

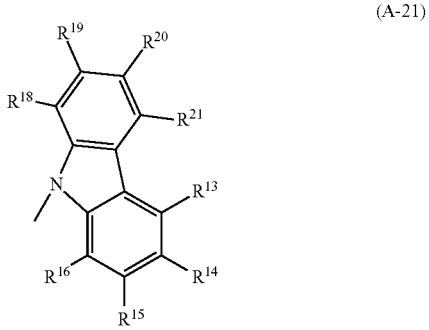
(A-21)

In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

Another embodiment of the present invention is an organic compound represented by General Formula (G1) below.

(G1)
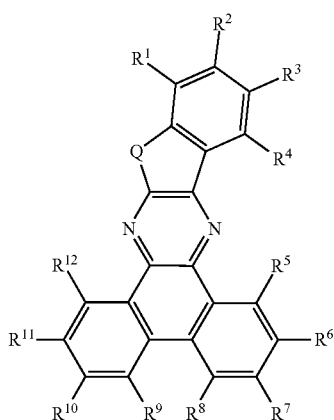
In General Formula (G1), Q represents O or S, at least one of $R^1$ to $R^{12}$ represents a first group represented by any one of General Formulae (A-1) to (A-21) below, and the other or others of $R^1$ to $R^{12}$ each independently represent any one of hydrogen, a halogeno group, a hydroxy group, an amino group, a nitro group, and a group having 1 to 50 carbon atoms.
(A-1)
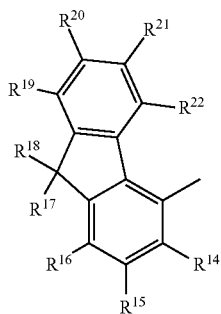
(A-2)
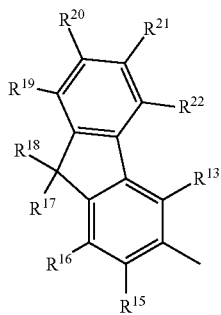
(A-3)
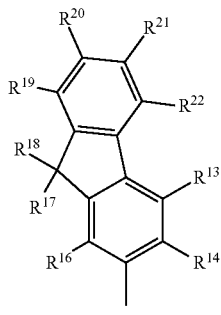
-continued
(A-4)
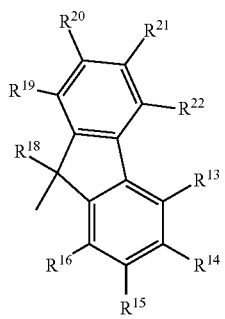
(A-5)
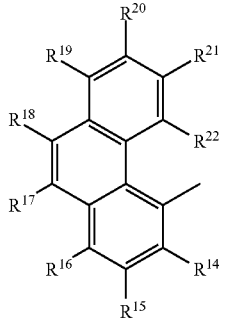
(A-6)
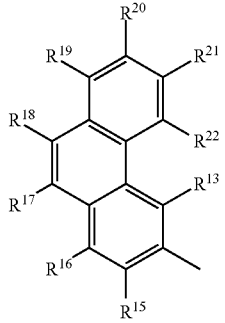
(A-7)
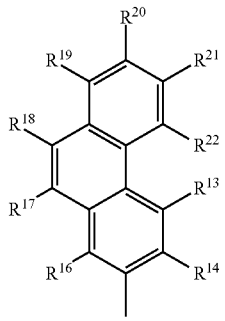
(A-8)
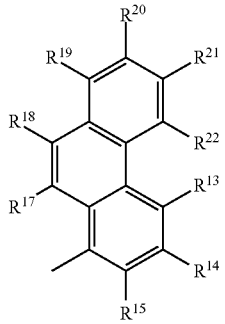

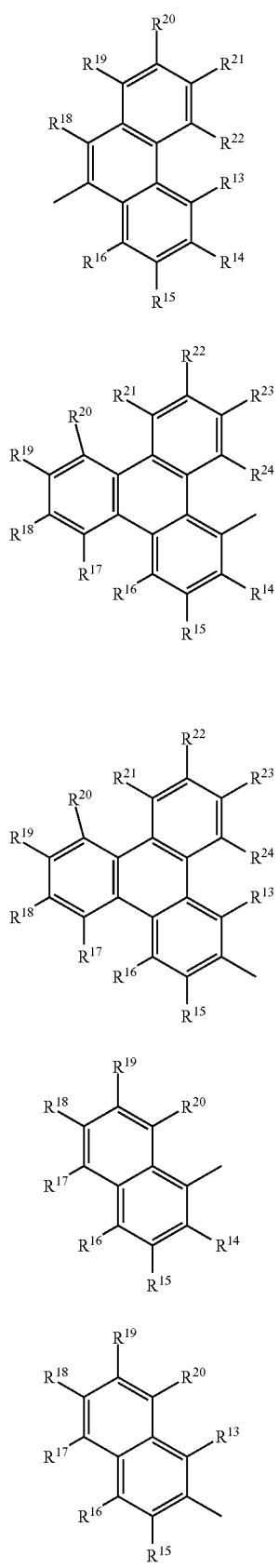 (A-9) (A-10) (A-11) (A-12) (A-13)
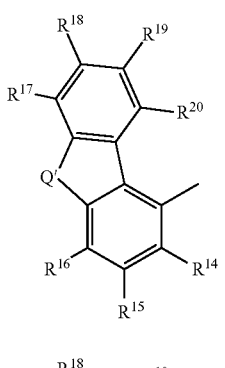 (A-14)
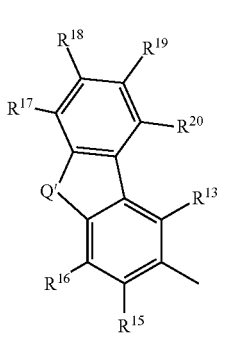 (A-15)
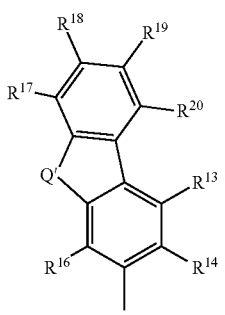 (A-16)
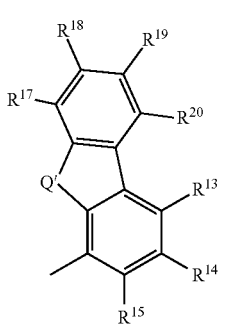 (A-17)
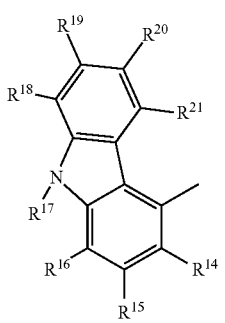 (A-18)

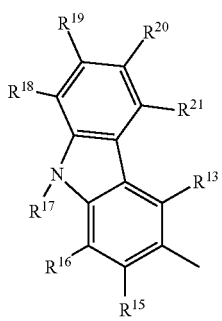

(A-19)

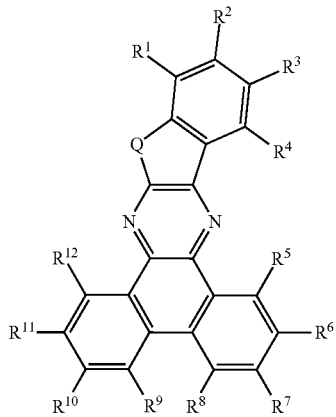

(G1)

In General Formula (G1), Q represents O or S, $R^3$ represents a first group having a substituted or unsubstituted condensed aromatic ring or condensed heteroaromatic ring having 3 to 30 carbon atoms, and R', $R^2$, and $R^4$ to $R^{12}$ each independently represent any one of hydrogen, a halogeno group, a hydroxy group, an amino group, a nitro group, and a group having 1 to 50 carbon atoms.

Another embodiment of the present invention is an organic compound represented by General Formula (G1) below.

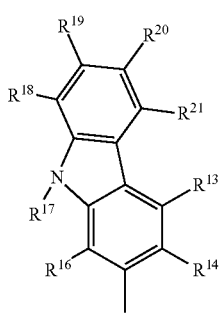

(A-20)

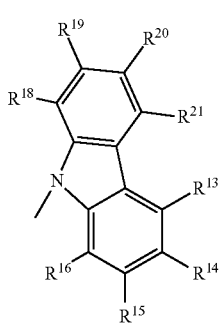

(A-21)

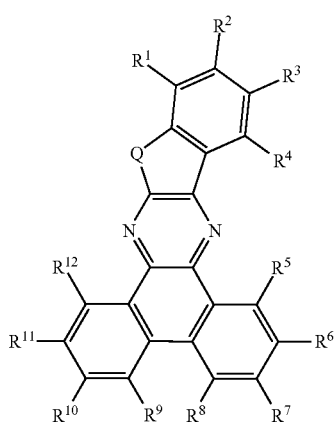

(G1)

In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

Another embodiment of the present invention is an organic compound represented by General Formula (G1) below.

In General Formula (G1), Q represents O or S, $R^3$ represents a first group having a substituted or unsubstituted hole-transport skeleton having 3 to 30 carbon atoms in a ring, and $R^1$, $R^2$, and $R^4$ to $R^{12}$ each independently represent any one of hydrogen, a halogeno group, a hydroxy group, an amino group, a nitro group, and a group having 1 to 50 carbon atoms.

Another embodiment of the present invention is an organic compound represented by General Formula (G1) below.

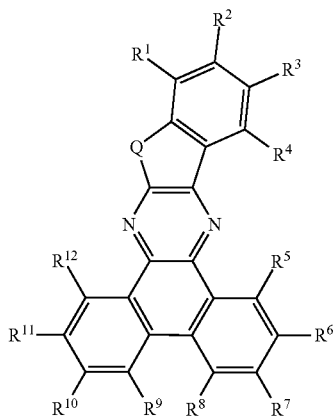

(G1)

In General Formula (G1), Q represents O or S, $R^3$ represents a first group having any one of a fluorene skeleton, a phenanthrene skeleton, a triphenylene skeleton, a naphthalene skeleton, a dibenzothiophene skeleton, a dibenzofuran skeleton, and a carbazole skeleton, and $R^1$, $R^2$, and $R^4$ to $R^{12}$ each independently represent any one of hydrogen, a halogeno group, a hydroxy group, an amino group, a nitro group, and a group having 1 to 50 carbon atoms.

In each of the above embodiments, $R^3$ preferably has 3 to 100 carbon atoms in total.

Another embodiment of the present invention is an organic compound represented by General Formula (G1) below.

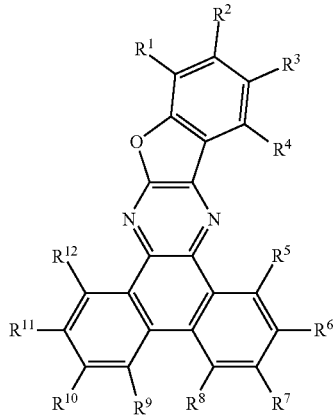

(G1)

In General Formula (G1), Q represents O or S, $R^3$ represents a first group to which any one of structures represented by General Formulae (A-1) to (A-21) below is bonded through a substituted or unsubstituted arylene group having 6 to 24 carbon atoms in a ring or a substituted or unsubstituted heteroarylene group having 3 to 24 carbon atoms in a ring, and $R^1$, $R^2$, and $R^4$ to $R^{12}$ each independently represent any one of hydrogen, a halogeno group, a hydroxy group, an amino group, a nitro group, and a group having 1 to 50 carbon atoms.

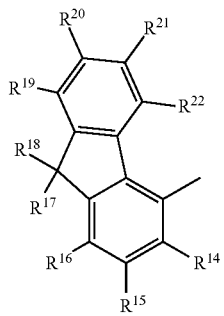

(A-1)

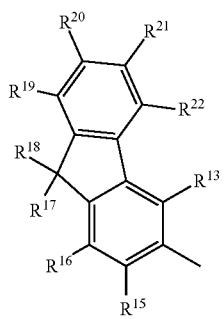

(A-2)

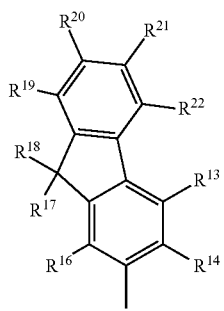

(A-3)

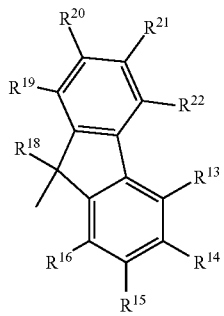

(A-4)

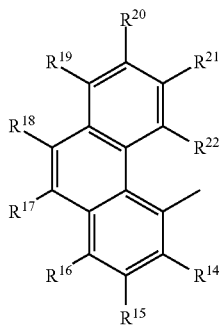

(A-5)

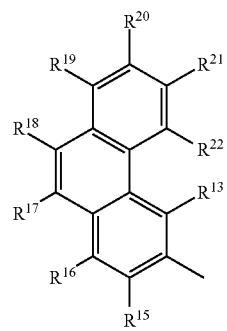
(A-6)
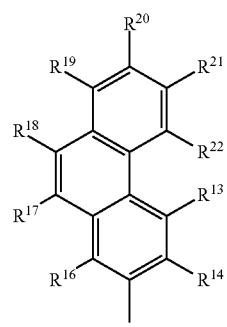
(A-7)
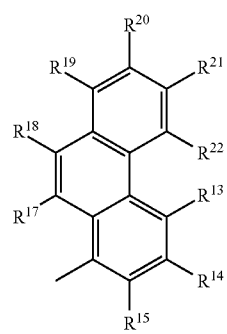
(A-8)
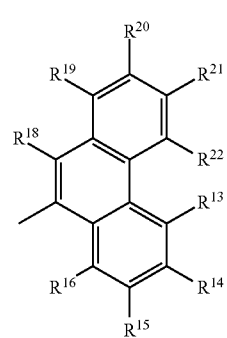
(A-9)
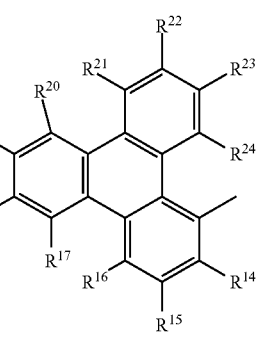
(A-10)
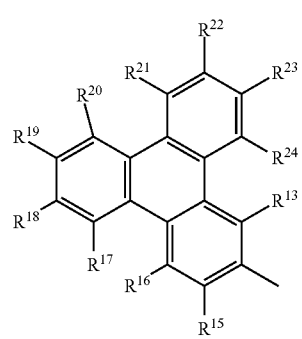
(A-11)
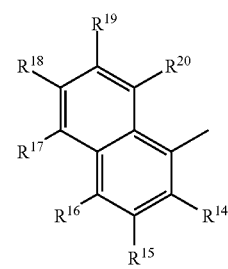
(A-12)
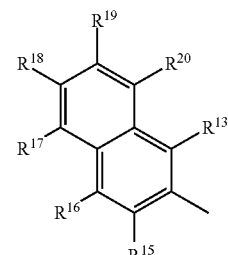
(A-13)
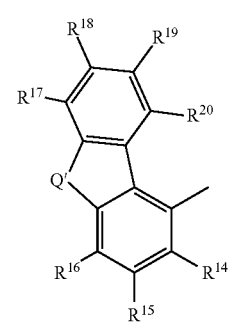
(A-14)
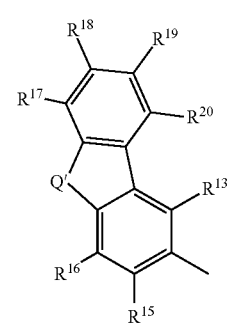
(A-15)

(A-16)
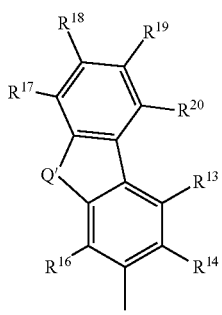

(A-17)
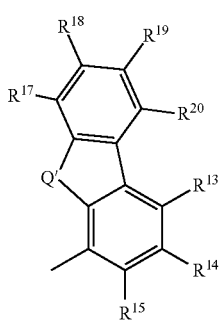

(A-18)
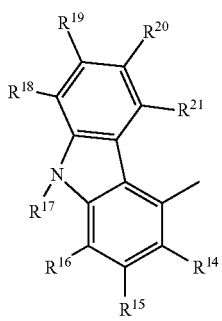

(A-19)
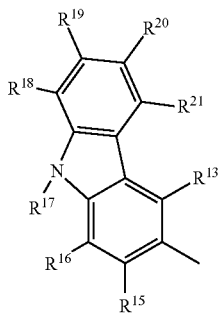

(A-20)
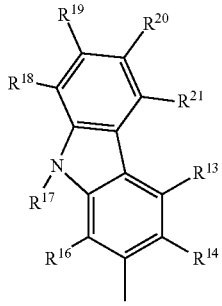

(A-21)
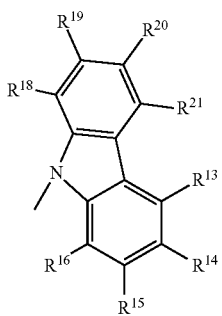

In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

Another embodiment of the present invention is an organic compound represented by General Formula (G1) below.

(G1)
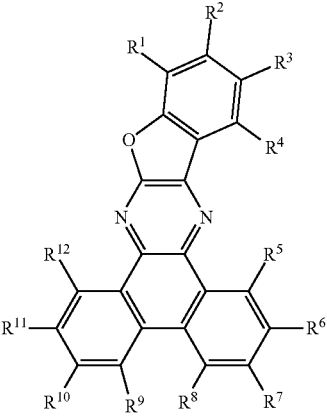

In General Formula (G1), Q represents O or S, $R^3$ represents a first group represented by any one of General Formulae (A-1) to (A-21) below, and $R^1$, $R^2$, and $R^4$ to $R^{12}$ each independently represent any one of hydrogen, a halogeno group, a hydroxy group, an amino group, a nitro group, and a group having 1 to 50 carbon atoms.

(A-1)
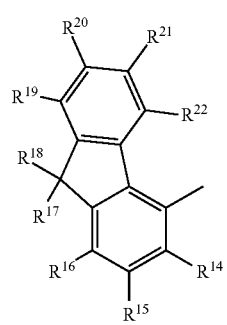

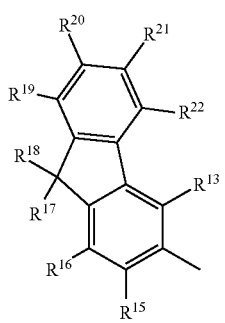 (A-2)
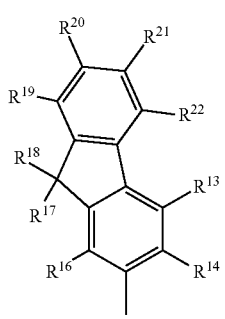 (A-3)
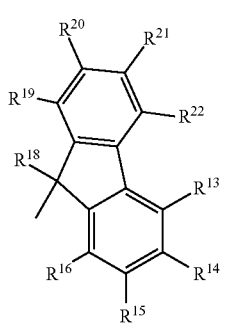 (A-4)
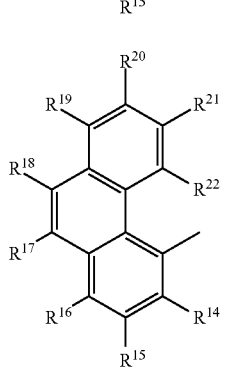 (A-5)
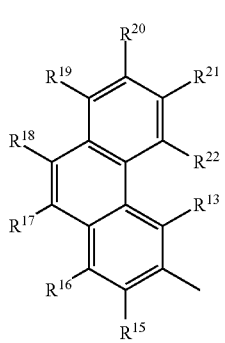 (A-6)
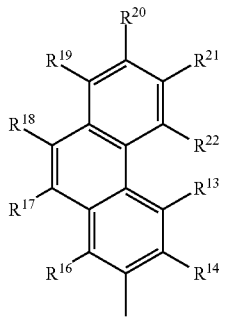 (A-7)
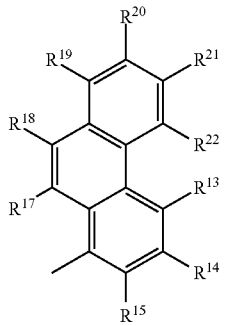 (A-8)
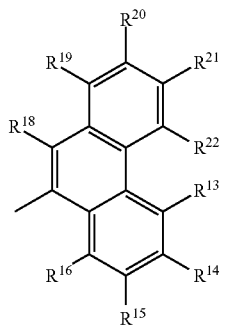 (A-9)
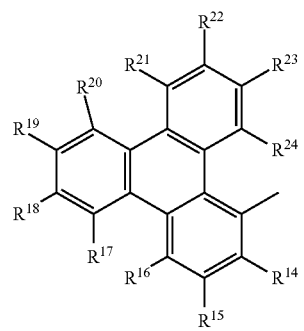 (A-10)
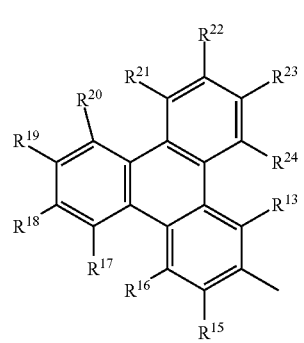 (A-11)

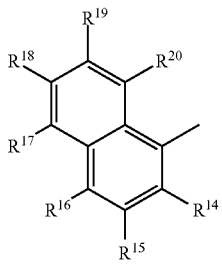
(A-12)
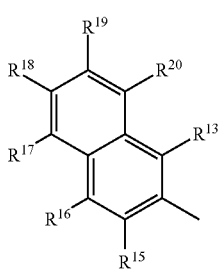
(A-13)
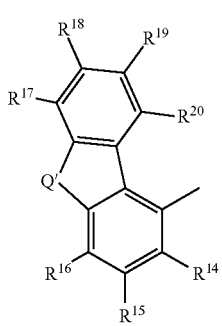
(A-14)
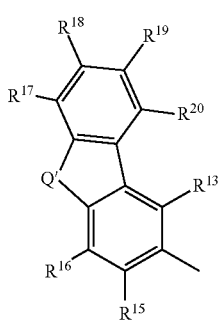
(A-15)
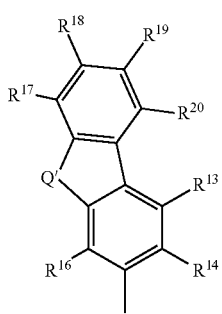
(A-16)
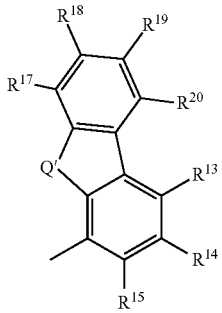
(A-17)
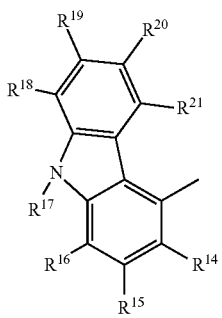
(A-18)
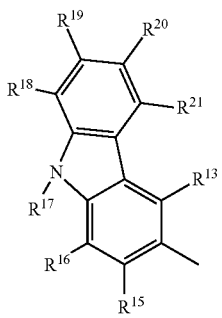
(A-19)
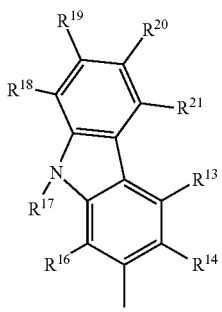
(A-20)
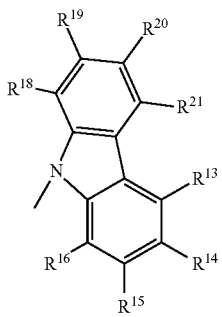
(A-21)
In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

In each of the above embodiments, the group having 1 to 50 carbon atoms is any one of an alkyloxy group, an aryloxy group, an amino group to which an alkyl group is bonded, an amino group to which an aryl group is bonded, a cyano group, a carboxyl group, an alkyloxycarbonyl group, an aryloxycarbonyl group, a silyl group to which an alkyl group is bonded, a silyl group to which an aryl group is bonded, an alkyl group, a cycloalkyl group, a heteroaryl group, and an aryl group.

Another embodiment of the present invention is an organic compound represented by Structural Formula (100) or Structural Formula (125).

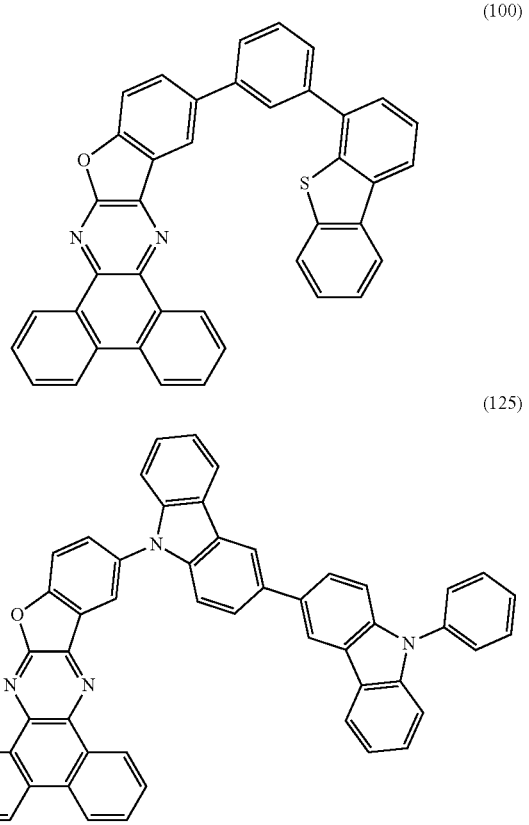

Another embodiment of the present invention is a light-emitting element containing an organic compound having a benzofuroquinoxaline skeleton or a benzothienoquinoxaline skeleton, preferably a light-emitting element containing an organic compound having a dibenzo[f,h][1]benzofuro[2,3-b]quinoxaline skeleton or a dibenzo[f,h][1]benzothieno[2,3-b]quinoxaline skeleton. Note that one embodiment of the present invention also includes a light-emitting element containing the above organic compound and a substance that converts triplet excitation energy into light emission, such as a phosphorescent material containing an organometallic complex or a TADF material.

Another embodiment of the present invention is a light-emitting element containing the organic compound of one embodiment of the present invention described above. Note that one embodiment of the present invention also includes a light-emitting element in which an EL layer provided between a pair of electrodes or a light-emitting layer included in the EL layer contains the organic compound of one embodiment of the present invention. In addition to the above light-emitting elements, a light-emitting device including a transistor, a substrate, and the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

The organic compound of one embodiment of the present invention can be used as a light-emitting substance. Alternatively, the organic compound of one embodiment of the present invention can be used in combination with a light-emitting substance that emits phosphorescence (phosphorescent compound) for a light-emitting layer of a light-emitting element. That is, light emission from a triplet excited state can be obtained from the light-emitting layer; thus, the efficiency of the light-emitting element can be improved, which is very effective. Accordingly, one embodiment of the present invention also includes a light-emitting element in which the organic compound of one embodiment of the present invention and a phosphorescent compound are used in combination in a light-emitting layer. A structure in which the light-emitting layer further contains a third substance may also be employed.

One embodiment of the present invention includes, in its scope, a light-emitting device including a light-emitting element, and a lighting device including the light-emitting device. Accordingly, the light-emitting device in this specification refers to an image display device and a light source (including a lighting device). In addition, the light-emitting device includes, in its category, all of a module in which a connector such as a flexible printed circuit (FPC) or a tape carrier package (TCP) is connected to a light-emitting device, a module in which a printed wiring board is provided at the end of a TCP, and a module in which an integrated circuit (IC) is directly mounted on a light-emitting element by a chip on glass (COG) method.

According to one embodiment of the present invention, a novel organic compound can be provided. In other words, a novel organic compound that is effective in improving the element characteristics and reliability can be provided. According to one embodiment of the present invention, a novel organic compound that can be used in a light-emitting element can be provided. According to one embodiment of the present invention, a novel organic compound that can be used in an EL layer of a light-emitting element can be provided. According to one embodiment of the present invention, a highly efficient, highly reliable, and novel light-emitting element using a novel organic compound of one embodiment of the present invention can be provided. In addition, a novel light-emitting device, a novel electronic device, or a novel lighting device can be provided. Note that the description of these effects does not disturb the existence of other effects. In one embodiment of the present invention, there is not necessarily a need to achieve all the effects. Other effects will be apparent from and can be derived from the description of the specification, the drawings, the claims, and the like.

DETAILED DESCRIPTION OF THE INVENTION

Figure 1A:
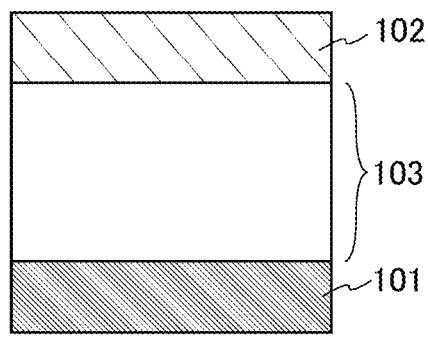
FIGS. 1A to 1E illustrate structures of light-emitting elements.

Embodiments of the present invention will be described below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In the description of modes of the present invention with reference to the drawings in this specification and the like, the same components in different diagrams are commonly denoted by the same reference numeral.

Embodiment 1

In this embodiment, organic compounds of embodiments of the present invention will be described.

The organic compounds of embodiments of the present invention each have a structure represented by General Formula (G1) having a dibenzobenzofuroquinoxaline skeleton or a dibenzobenzothienoquinoxaline skeleton.

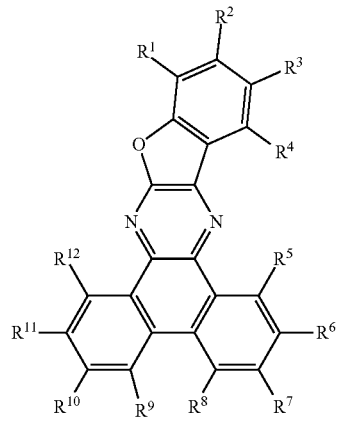

(G1)

In General Formula (G1), Q represents O or S, at least one of $R^1$ to $R^{12}$ represents a first group having a substituted or unsubstituted condensed aromatic ring or condensed heteroaromatic ring having 3 to 30 carbon atoms, and the other or others of $R^1$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, at least one of $R^1$ to $R^{12}$ represents a first group having a substituted or unsubstituted hole-transport skeleton having 3 to 30 carbon atoms in a ring, and the other or others of $R^1$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, at least one of $R^1$ to $R^{12}$ represents a first group having any one of a fluorene skeleton, a phenanthrene skeleton, a triphenylene skeleton, a naphthalene skeleton, a dibenzothiophene skeleton, a dibenzofuran skeleton, and a carbazole skeleton, and the other or others of $R^1$ to $R^{12}$ each independently represent any one of hydrogen, a halogeno group, a hydroxy group, an amino group, a nitro group, and a group having 1 to 50 carbon atoms.

In each of the above structures, the first group preferably has 3 to 100 carbon atoms in total.

Alternatively, in General Formula (G1), Q represents O or S, at least one of $R^1$ to $R^{12}$ represents a first group to which any one of structures represented by General Formulae (A-1) to (A-21) below is bonded through a substituted or unsubstituted arylene group having 6 to 24 carbon atoms in a ring or a substituted or unsubstituted heteroarylene group having 3 to 24 carbon atoms in a ring, and the other or others of $R^1$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, at least one of $R^1$ to $R^{12}$ represents a first group represented by any one of General Formulae (A-1) to (A-21) below, and the other or others of $R^1$ to $R^{12}$ each independently represent any one of hydrogen, a halogeno group, a hydroxy group, an amino group, a nitro group, and a group having 1 to 50 carbon atoms.

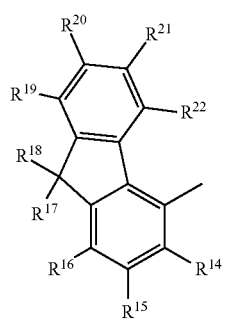
(A-1)
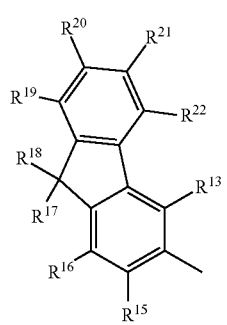
(A-2)
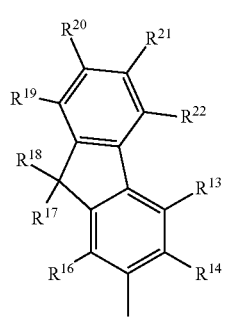
(A-3)
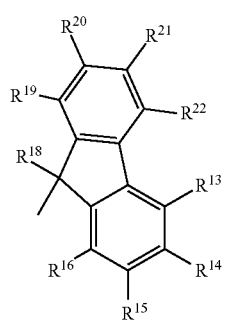
(A-4)
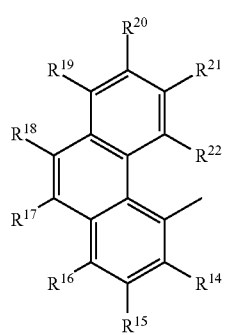
(A-5)
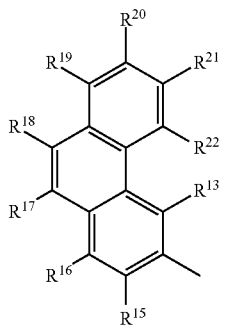
(A-6)
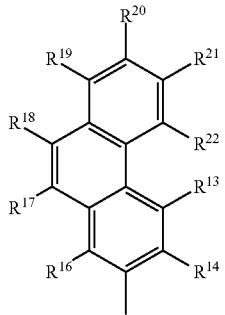
(A-7)
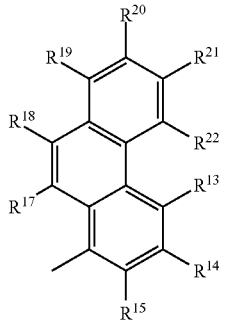
(A-8)
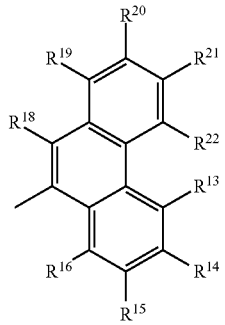
(A-9)
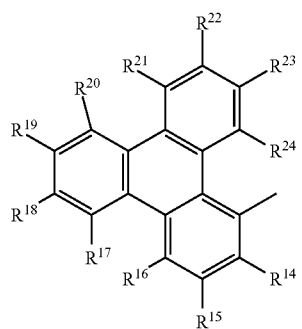
(A-10)

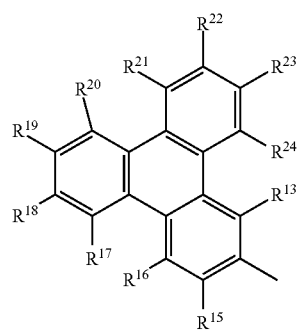
(A-11)
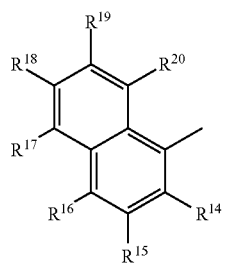
(A-12)
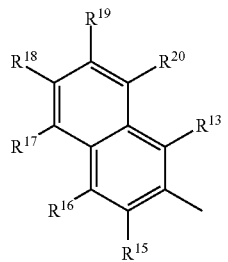
(A-13)
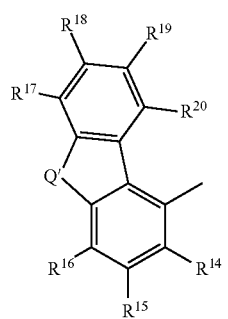
(A-14)
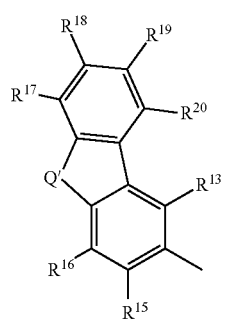
(A-15)
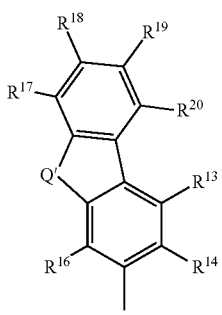
(A-16)
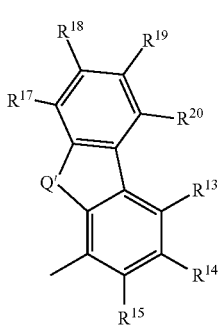
(A-17)
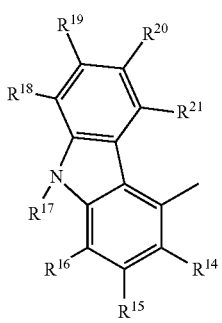
(A-18)
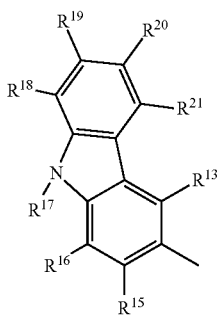
(A-19)
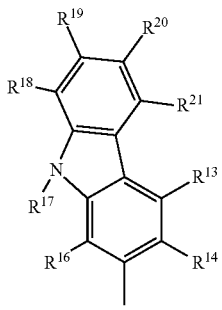
(A-20)

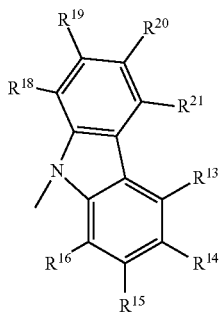
(A-21)

In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

Alternatively, in General Formula (G1), Q represents O or S, $R^3$ represents a first group having a substituted or unsubstituted condensed aromatic ring or condensed heteroaromatic ring having 3 to 30 carbon atoms, and R', $R^2$, and $R^4$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, $R^3$ represents a first group having a substituted or unsubstituted hole-transport skeleton having 3 to 30 carbon atoms in a ring, and $R^1$, $R^2$, and $R^4$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, $R^3$ represents a first group having any one of a fluorene skeleton, a phenanthrene skeleton, a triphenylene skeleton, a naphthalene skeleton, a dibenzothiophene skeleton, a dibenzofuran skeleton, and a carbazole skeleton, and $R^1$, $R^2$, and $R^4$ to $R^{12}$ each independently represent any one of hydrogen, a halogeno group, a hydroxy group, an amino group, a nitro group, and a group having 1 to 50 carbon atoms.

In each of the above structures, $R^3$ preferably has 3 to 100 carbon atoms in total.

Alternatively, in General Formula (G1), Q represents O or S, $R^3$ represents a first group to which any one of the structures represented by General Formulae (A-1) to (A-21) below is bonded through a substituted or unsubstituted arylene group having 6 to 24 carbon atoms in a ring or a substituted or unsubstituted heteroarylene group having 3 to 24 carbon atoms in a ring, and $R^1$, $R^2$, and $R^4$ to $R^{12}$ each independently represent any one of hydrogen, a halogeno group, a hydroxy group, an amino group, a nitro group, and a group having 1 to 50 carbon atoms.

Alternatively, in General Formula (G1), Q represents O or S, $R^3$ represents a first group represented by any one of General Formulae (A-1) to (A-21) below, and $R^1$, $R^2$, and $R^4$ to $R^{12}$ each independently represent any one of hydrogen, a halogeno group, a hydroxy group, an amino group, a nitro group, and a group having 1 to 50 carbon atoms.

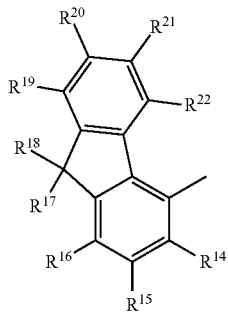
(A-1)

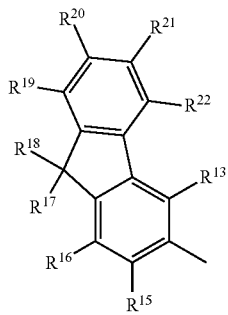
(A-2)

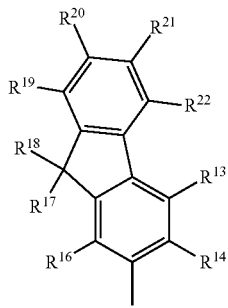
(A-3)

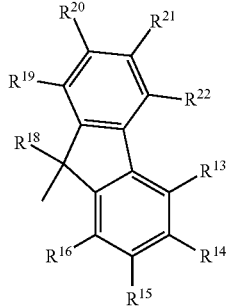
(A-4)

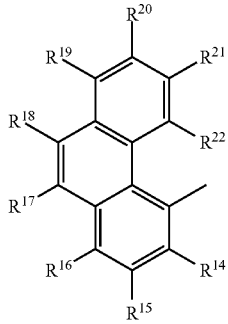
(A-5)

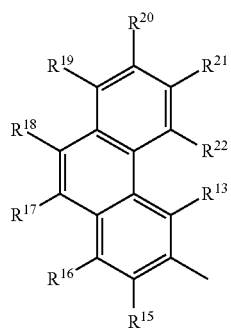 (A-6)
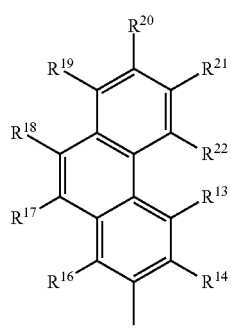 (A-7)
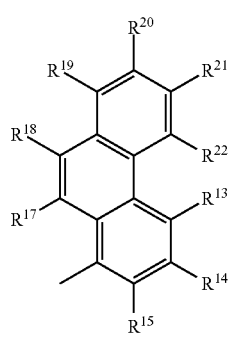 (A-8)
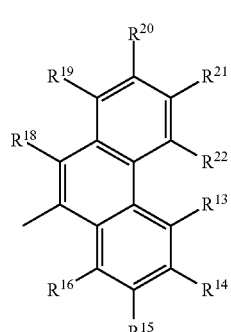 (A-9)
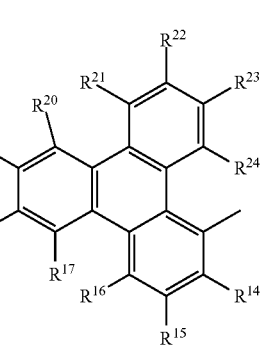 (A-10)
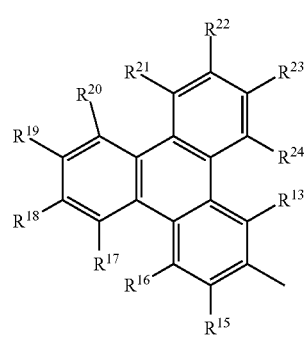 (A-11)
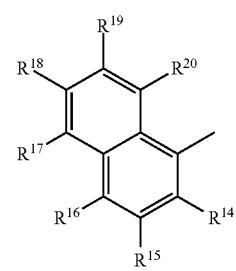 (A-12)
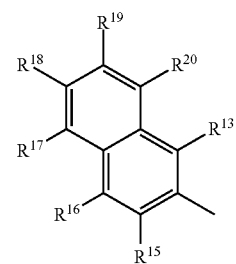 (A-13)
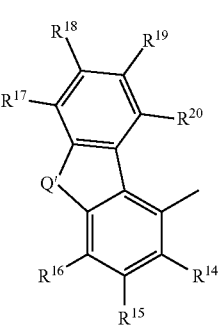 (A-14)
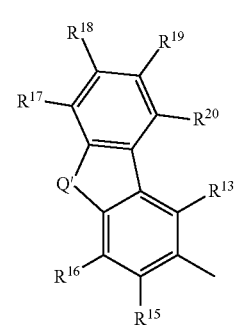 (A-15)

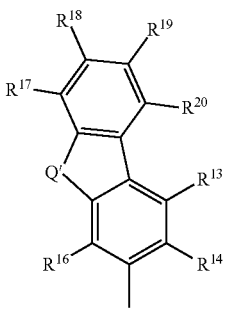 (A-16)

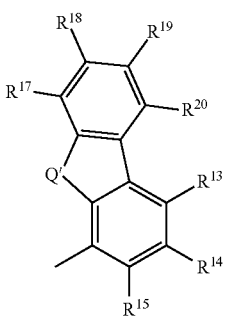 (A-17)

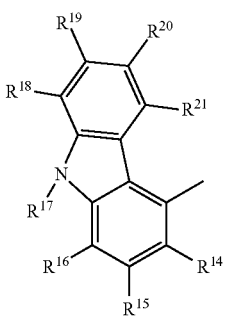 (A-18)

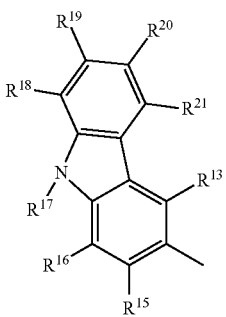 (A-19)

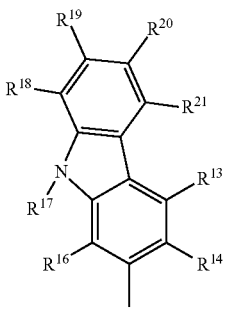 (A-20)

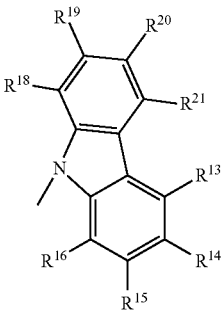 (A-21)

In General Formulae (A-1) to (A-21), Q' represents O or S, and $R^{13}$ to $R^{24}$ each independently represent any one of hydrogen, an alkyl group having 1 to 6 carbon atoms, a substituted or unsubstituted cycloalkyl group having 5 to 7 carbon atoms in a ring, a substituted or unsubstituted phenyl group, and a substituted or unsubstituted carbazolyl group.

Note that in each of the above structures, the group having 1 to 50 carbon atoms is preferably any one of an alkyloxy group, an aryloxy group, an amino group to which an alkyl group is bonded, an amino group to which an aryl group is bonded, a cyano group, a carboxyl group, an alkyloxycarbonyl group, an aryloxycarbonyl group, a silyl group to which an alkyl group is bonded, a silyl group to which an aryl group is bonded, an alkyl group, a cycloalkyl group, a heteroaryl group, and an aryl group. Specific examples of these groups include a methoxy group, an ethoxy group, a propoxy group, a tert-butoxy group, a phenoxy group, a 4-methylphenoxy group, a 3,5-dimethylphenoxy group, a 1-naphthoxy group, a 2-naphthoxy group, a methylamino group, an ethylamino group, a dimethylamino group, a diethylamino group, a methylethylamino group, a phenylmethylamino group, a phenylamino group, a diphenylamino group, a 1-naphthylamino group, a 2-naphthylamino group, an N-1-naphthyl-N-phenylamino group, an N-2-naphthyl-N-phenylamino group, a bis(biphenyl-4-yl)amino group, an N,N-bis(p-terphenyl)amino group, a methoxycarbonyl group, an ethoxycarbonyl group, a phenoxycarbonyl group, a trimethylsilyl group, a triphenylsilyl group, a methyl group, an ethyl group, a propyl group, an isopropyl group, a butyl group, an isobutyl group, a tert-butyl group, an n-hexyl group, a benzyl group, a cyclopropyl group, a cyclobutyl group, a cyclopentyl group, a cyclohexyl group, a phenyl group, a 1-naphthyl group, a 2-naphthyl group, a 2-biphenyl group, a 3-biphenyl group, a 4-biphenyl group, a phenanthrenyl group, a triphenylenyl group, a 9,9-dimethylfluorenyl group, a pyridyl group, a quinolyl group, a 9-carbazolyl group, a 9-phenyl-2-carbazolyl group, a 9-phenyl-3-carbazolyl group, a dibenzofuranyl group, and a dibenzothiophenyl group. Furthermore, groups having less than or equal to 25 carbon atoms, that is, 1 to 25 carbon atoms, such as a spirofluorenyl group and a N,N-bis(p-biphenylyl)amino group are preferable in terms of a sublimation property.

Note that in the organic compound of one embodiment of the present invention, hydrogen in the skeleton may be deuterium.

Note that in each of the above structures, substitution in General Formula (G1) and General Formulae (A-1) to (A-21) is preferably substitution by a substituent such as an alkyl group having 1 to 6 carbon atoms, e.g., a methyl group, an ethyl group, an n-propyl group, an isopropyl group, a sec-butyl group, a tert-butyl group, an n-pentyl group, and an n-hexyl group, or substitution by a substituent such as an aryl group having 6 to 12 carbon atoms, e.g., a phenyl group, an o-tolyl group, an m-tolyl group, a p-tolyl group, a 1-naphthyl group, a 2-naphthyl group, a 2-biphenyl group, a 3-biphenyl group, and a 4-biphenyl group. These substituents may be bonded to each other to form a ring. For example, in the case where the arylene group is a 2,7-fluorenylene group having two phenyl groups as substituents at the 9-position, the phenyl groups may be bonded to each other to form a spiro-9,9'-bifluorene-2,7-diyl group.

In each of the above structures, specific examples of the condensed aromatic ring or condensed heteroaromatic ring having 3 to 30 carbon atoms, which is represented by $R^1$ to $R^{12}$ in General Formula (G1), include a quinoline ring, an isoquinoline ring, a quinazoline ring, a quinoxaline ring, a naphthalene ring, a benzothiophene ring, a benzofuran ring, an indole ring, a fluorene ring, a phenanthrene ring, a triphenylene ring, a dibenzothiophene ring, a benzonaphthothiophene ring, a dibenzofuran ring, a benzonaphthofuran ring, a carbazole ring, a benzocarbazole ring, and a dibenzocarbazole ring.

In each of the above structures, specific examples of the hole-transport skeleton having 3 to 30 carbon atoms in a ring, which is represented by $R^1$ to $R^{12}$ in General Formula (G1), include a naphthalene ring, a benzothiophene ring, a benzofuran ring, an indole ring, a fluorene ring, a phenanthrene ring, a triphenylene ring, a dibenzothiophene ring, a benzonaphthothiophene ring, a dibenzofuran ring, a benzonaphthofuran ring, a carbazole ring, a benzocarbazole ring, and a dibenzocarbazole ring.

In each of the above structures, specific examples of the arylene group having 6 to 24 carbon atoms in a ring, which is represented by $R^1$ to $R^{12}$ in General Formula (G1), include a phenylene group, a naphthalenediyl group, a biphenyldiyl group, a terphenyldiyl group, a fluorenediyl group, a phenanthrenediyl group, and a triphenylenediyl group.

In each of the above structures, specific examples of the heteroarylene group having 3 to 24 carbon atoms in a ring, which is represented by $R^1$ to $R^{12}$ in General Formula (G1), include a pyridinediyl group, a pyrazinediyl group, a pyrimidinediyl group, a triazinediyl group, a triazolediyl group, an oxadiazolediyl group, a thiadiazolediyl group, an oxazolediyl group, a thiazolediyl group, a thiophenediyl group, a pyrrolediyl group, a furandiyl group, a selenophenediyl group, a benzothiophenediyl group, a benzopyrrolediyl group, a benzofurandiyl group, a quinolinediyl group, an isoquinolinediyl group, a dibenzothiophenediyl group, a carbazolediyl group, and a dibenzofurandiyl group.

In each of the above structures, specific examples of the alkyl group having 1 to 6 carbon atoms, which is represented by $R^{13}$ to $R^{24}$ in General Formulae (A-1) to (A-21), include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

In each of the above structures, specific examples of the cycloalkyl group having 5 to 7 carbon atoms in a ring, which is represented by $R^{13}$ to $R^{24}$ in General Formulae (A-1) to (A-21), include a cyclopentyl group, a cyclohexyl group, and a cycloheptyl group.

Next, specific structural formulas of the aforementioned organic compounds of embodiments of the present invention are shown below.

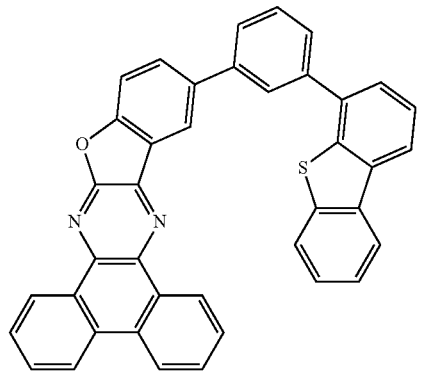

(100)

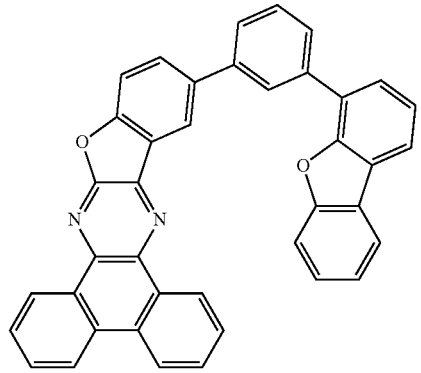

(101)

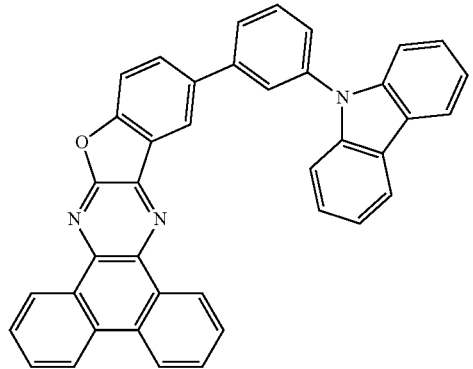

(102)

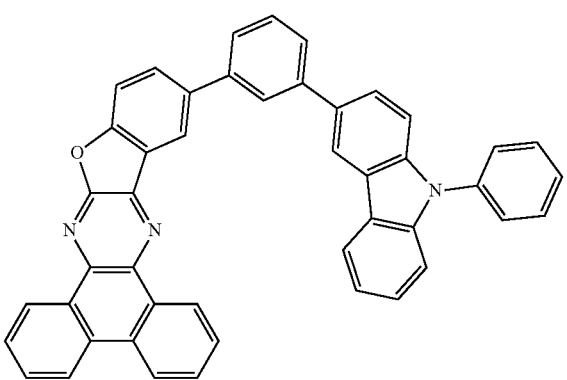

(103)

(104)
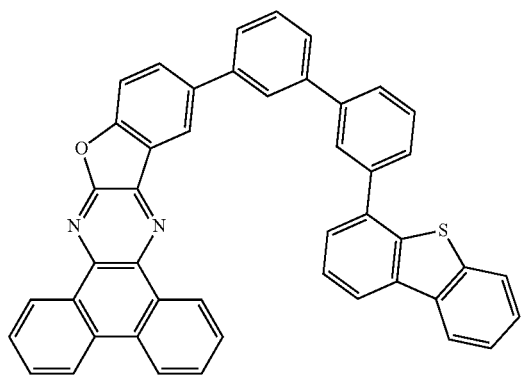
(105)
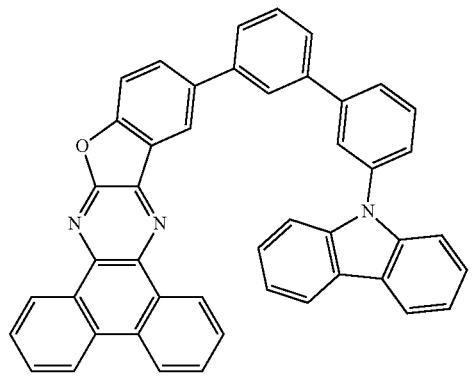
(106)
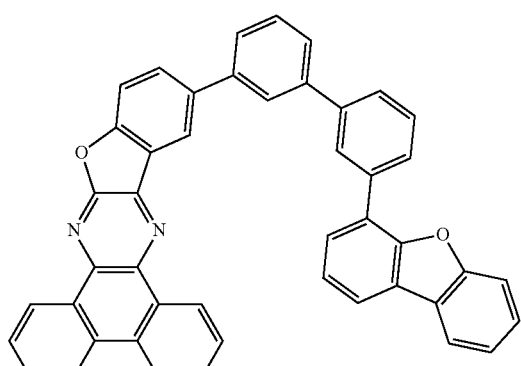
(107)
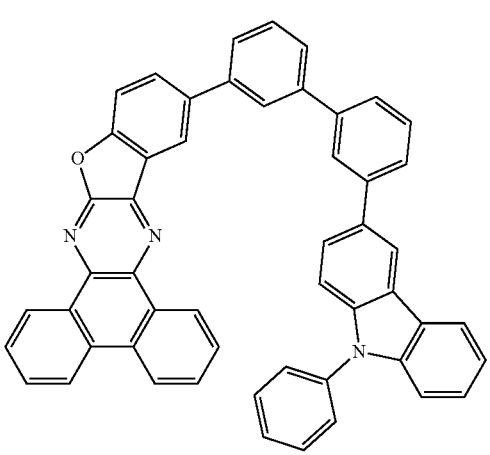
(108)
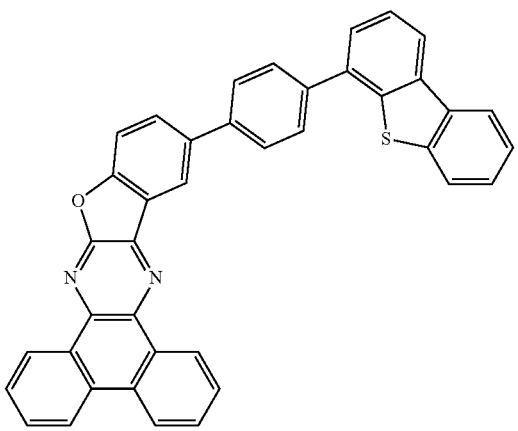
(109)
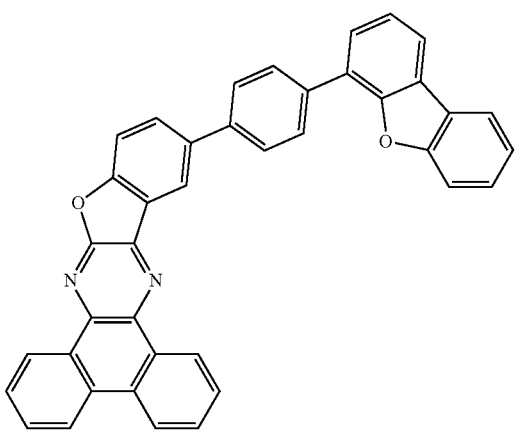
(110)
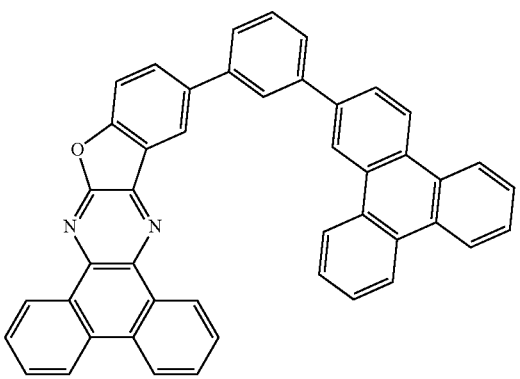

(111)
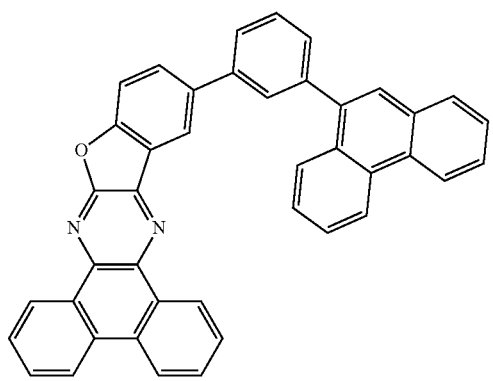
(112)
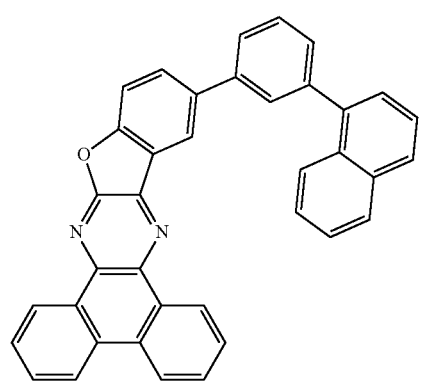
(113)
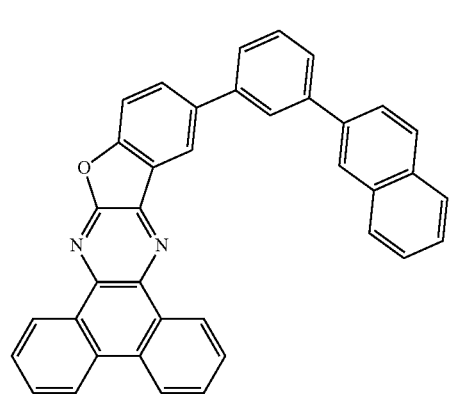
(114)
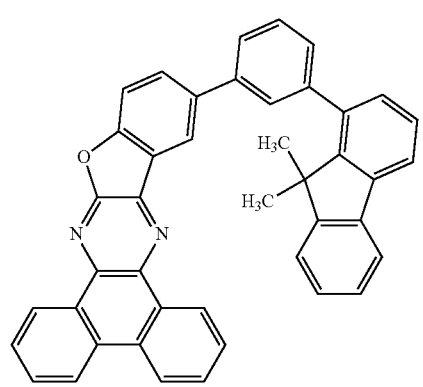
(115)
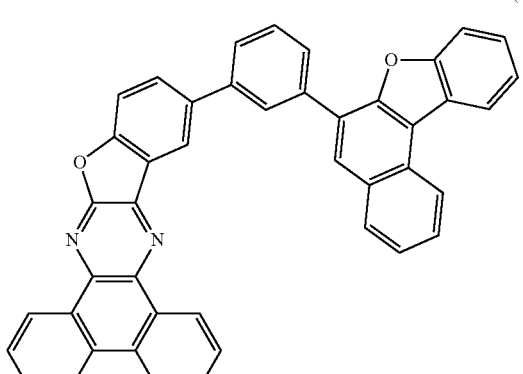
(116)
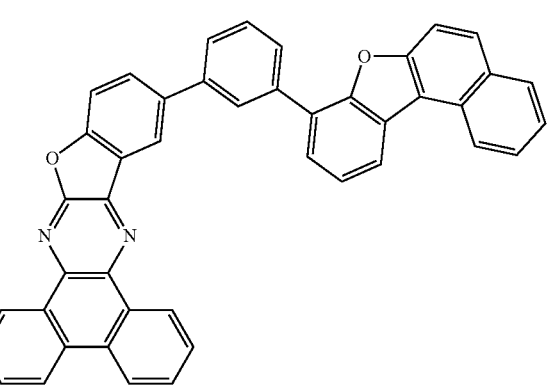
(117)
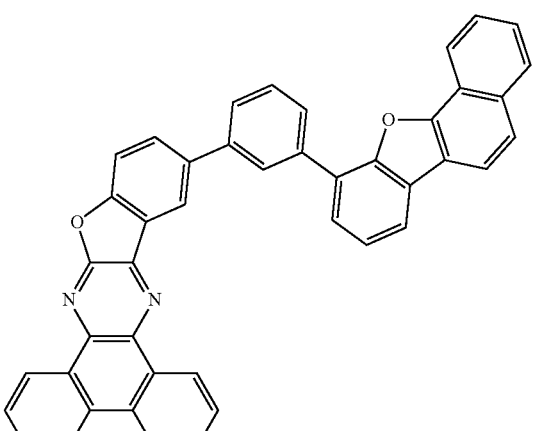
(118)
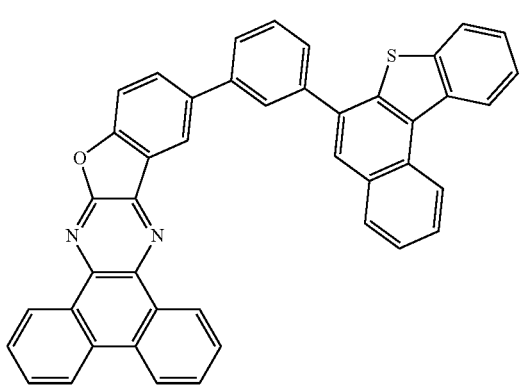

(119)
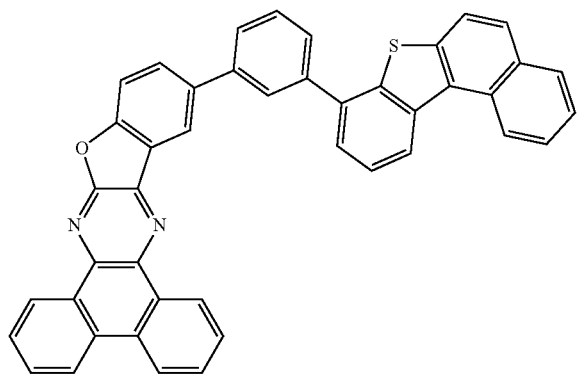
(120)
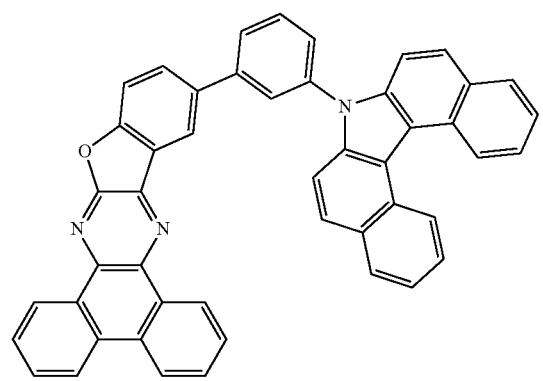
(121)
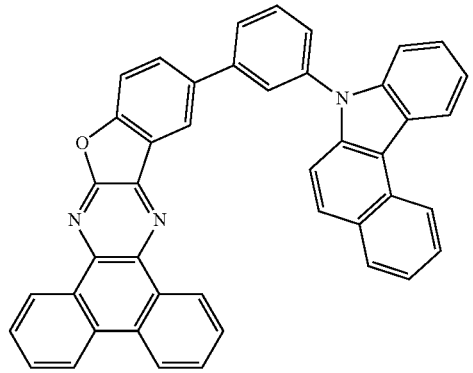
(122)
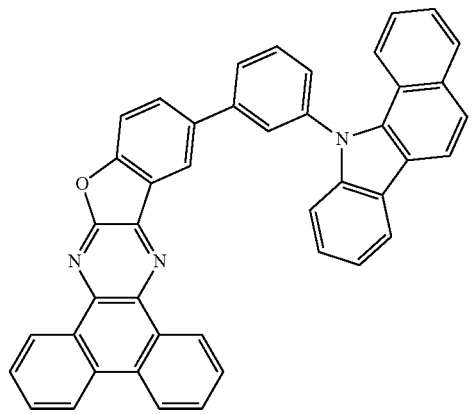
(123)
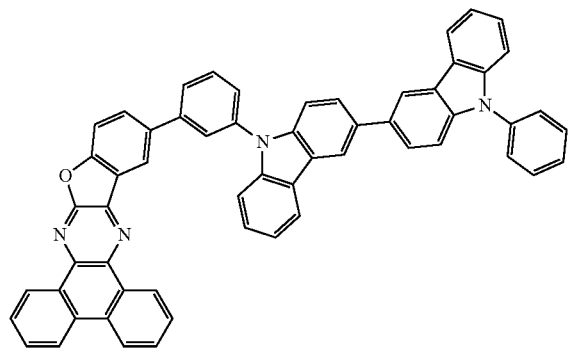
(124)
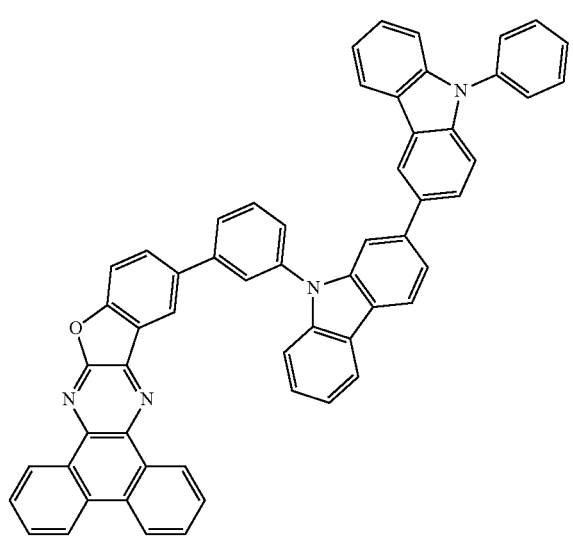
(125)
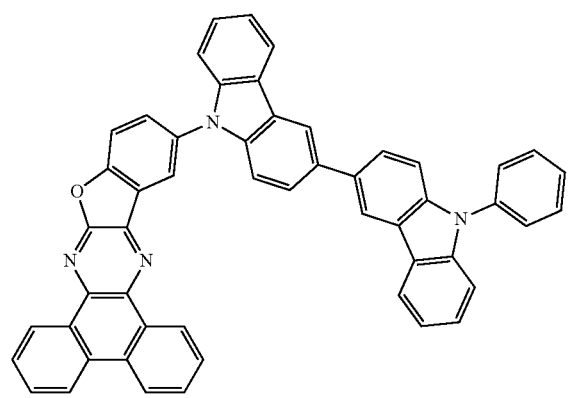

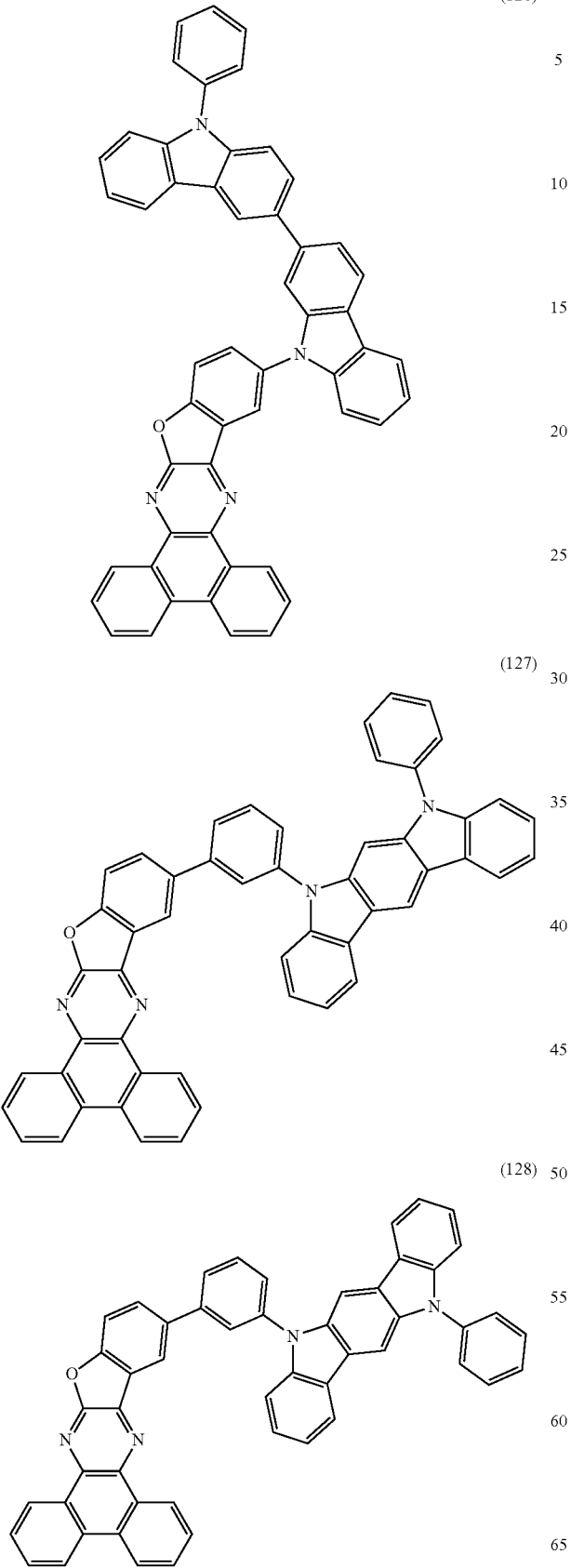
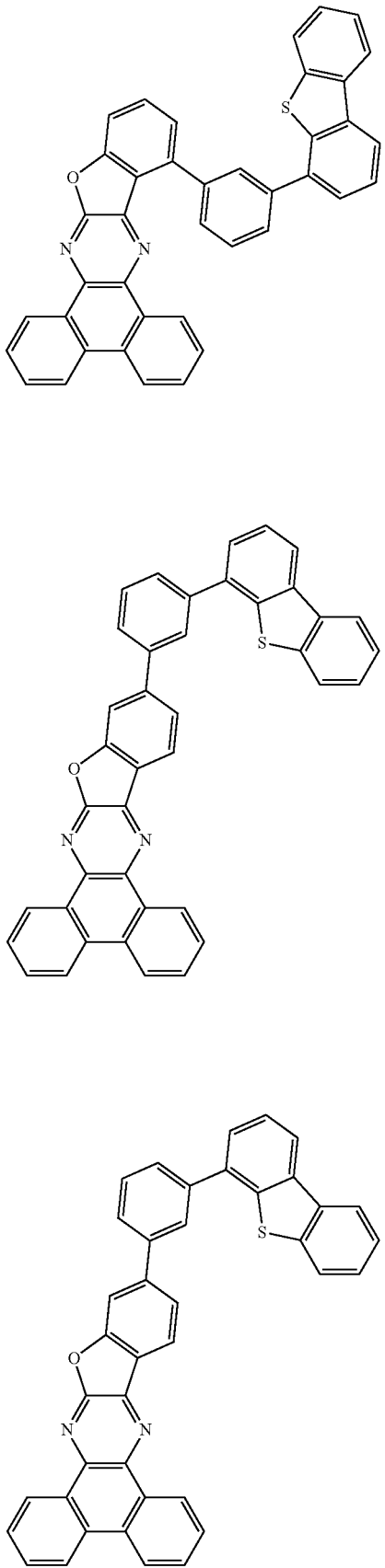

-continued
(132)
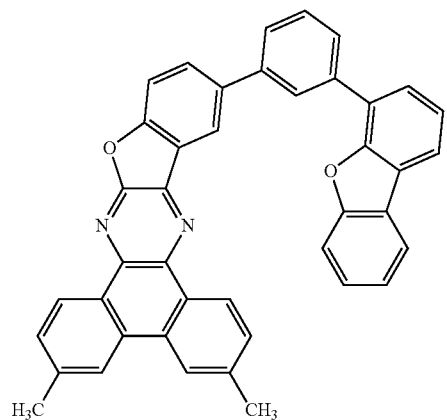
(133)
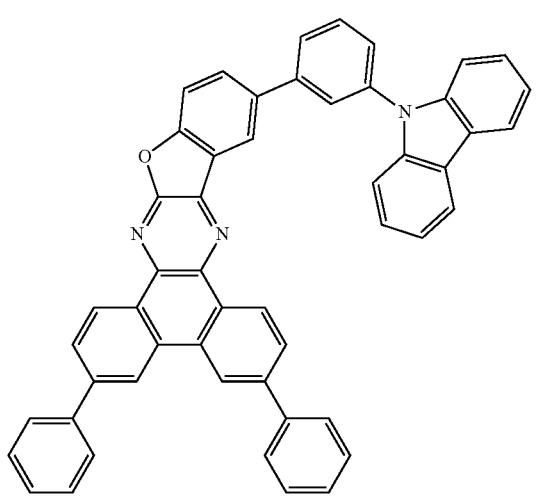
(134)
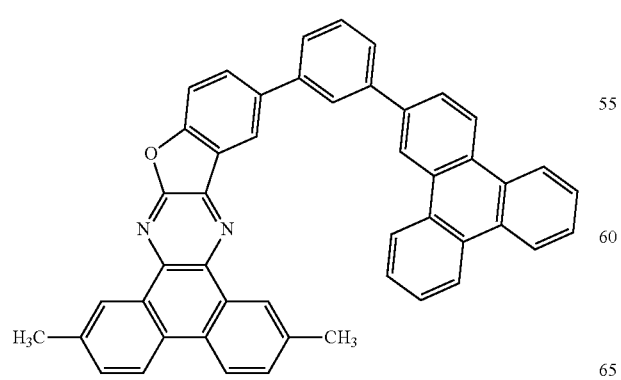
-continued
(135)
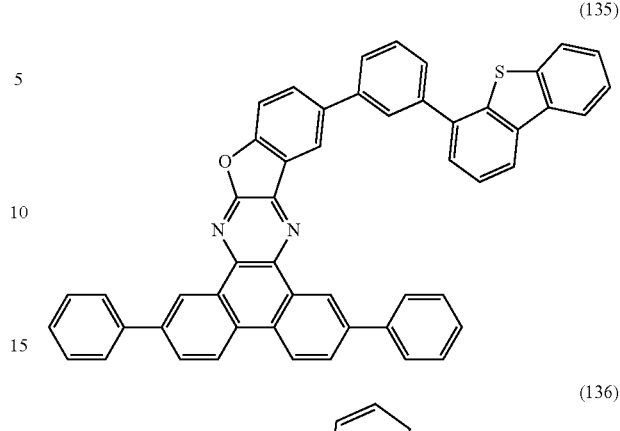
(136)
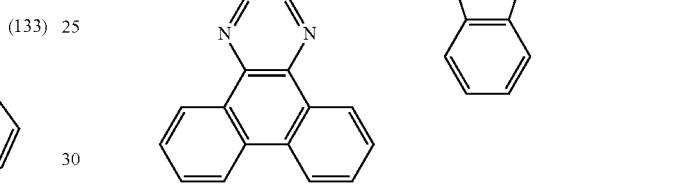
(137)
(138)
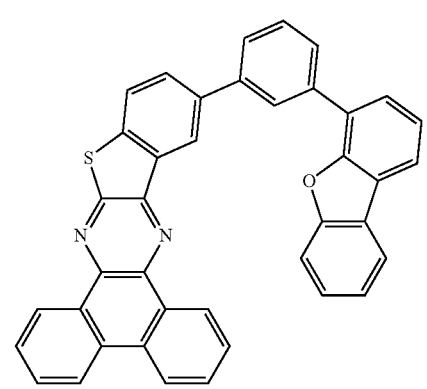

51
-continued
(139)
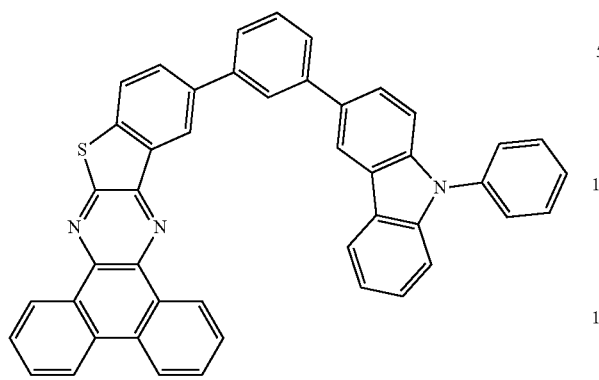
(140)
(141)
(142)
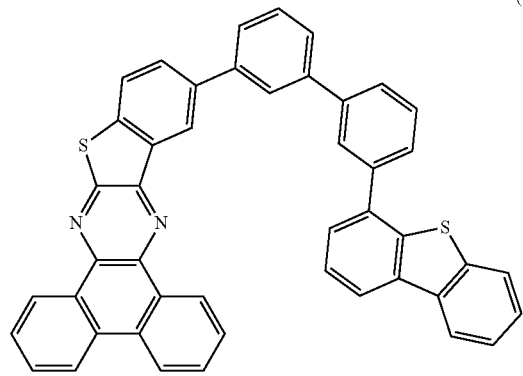
52
-continued
(143)
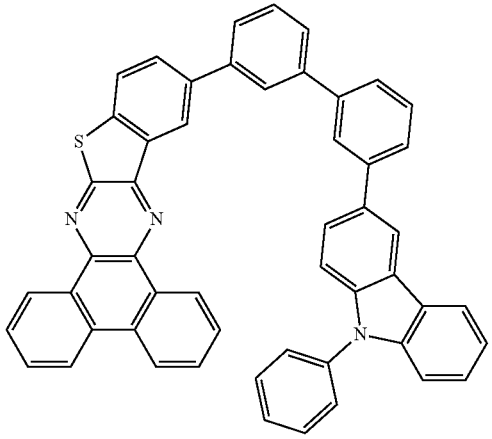
(144)
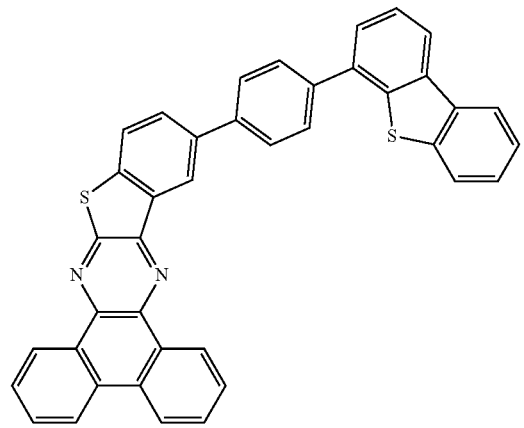
(145)
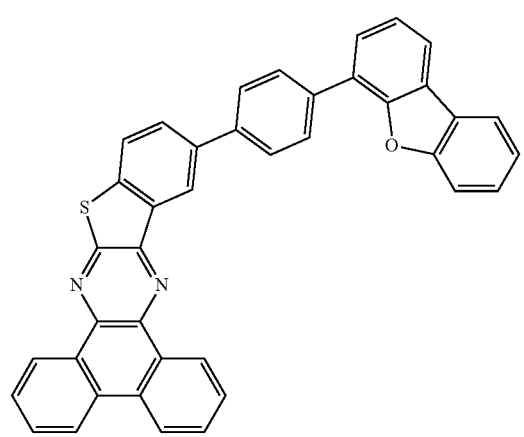

(146)
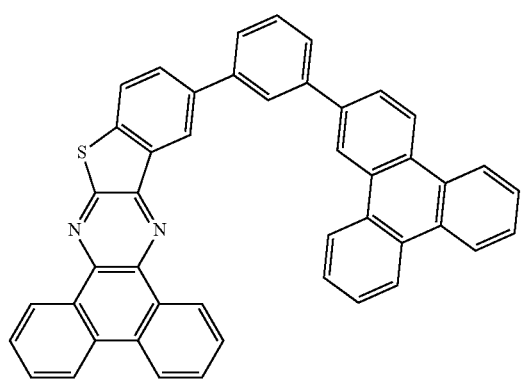
(147)
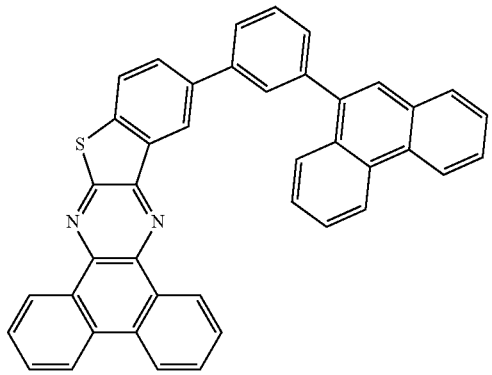
(148)
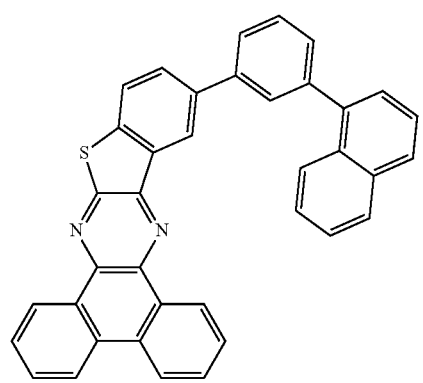
(149)
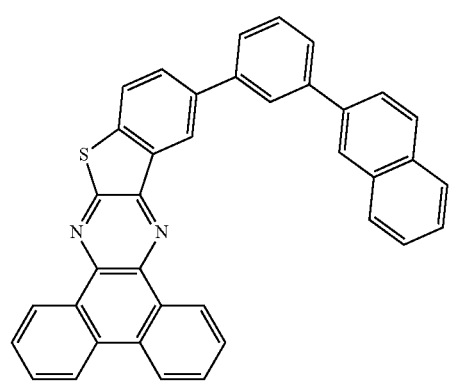
(150)
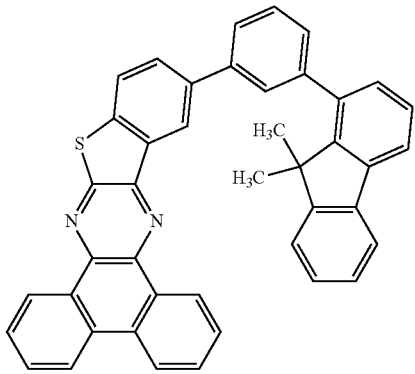
(151)
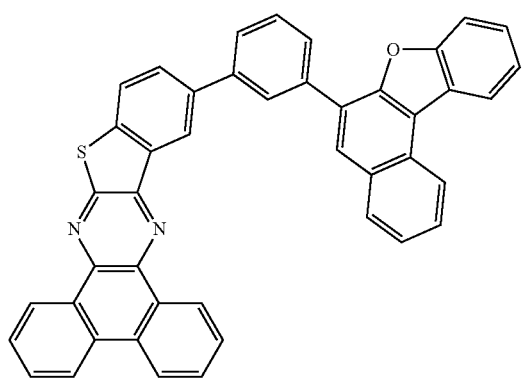
(152)
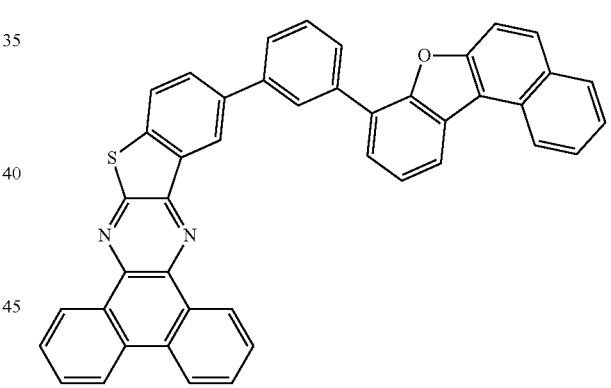
(153)
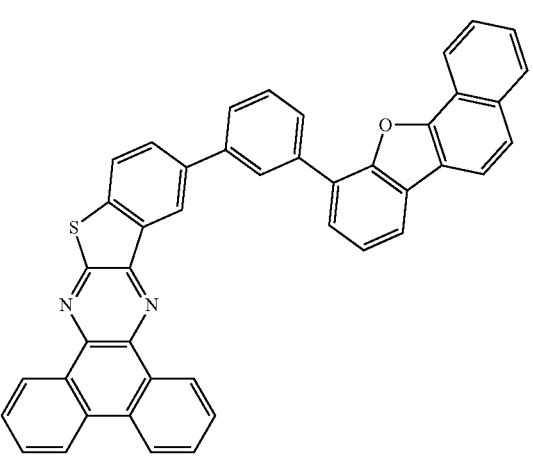

(154)
(155)
(156)
(157)
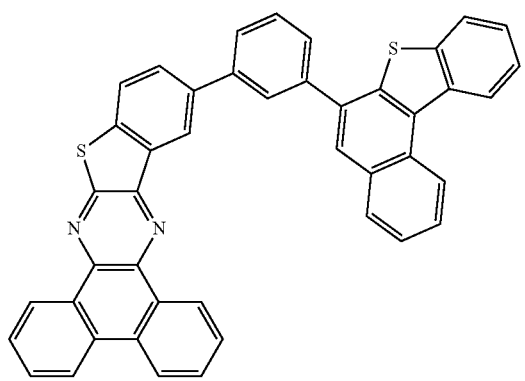
(158)
(159)
(160)
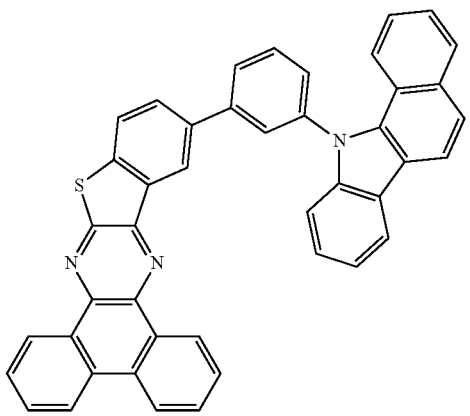
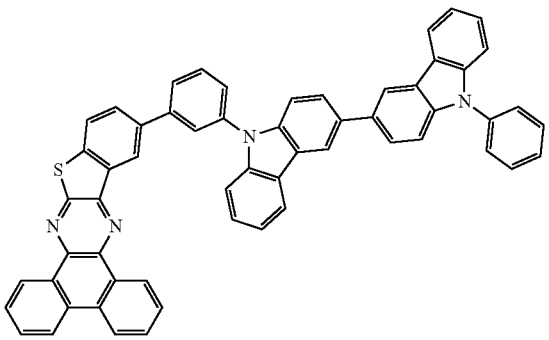
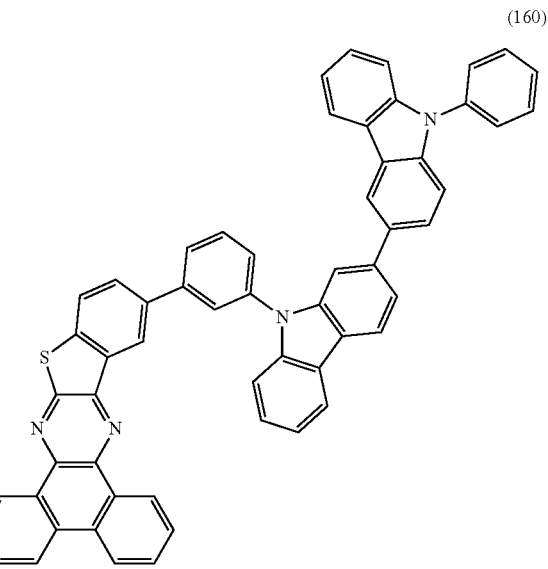

(161)
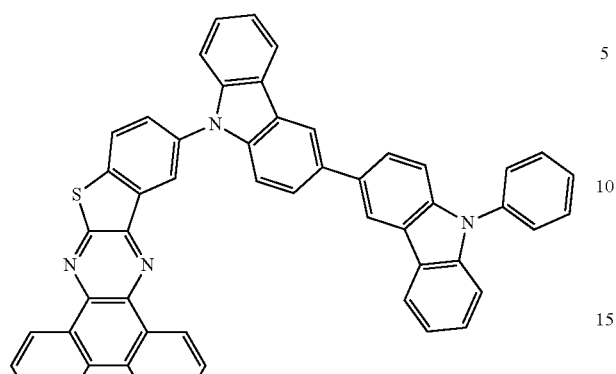
(162)
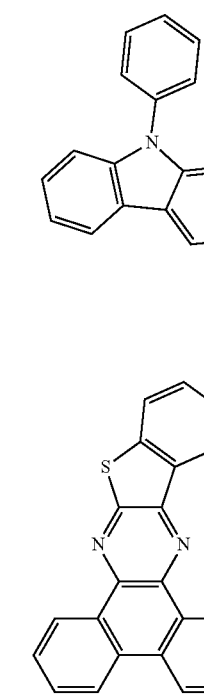
(163)
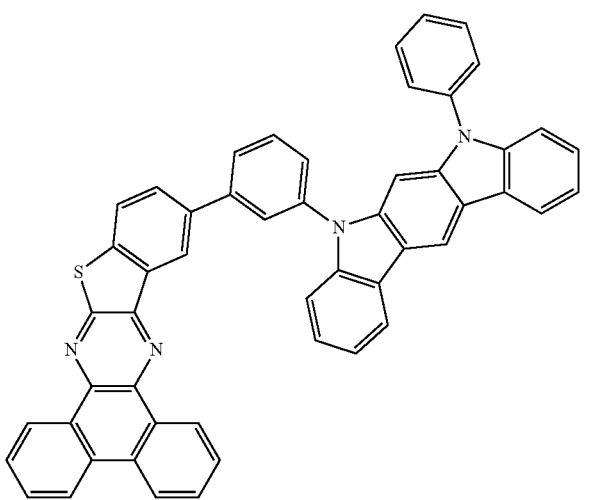
(164)
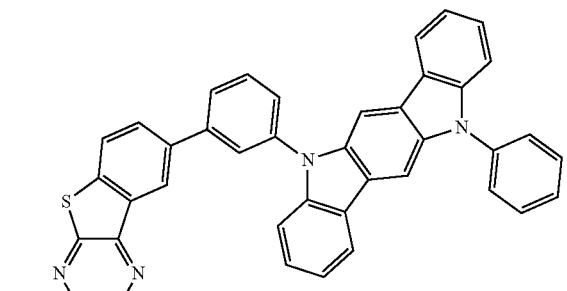
(165)
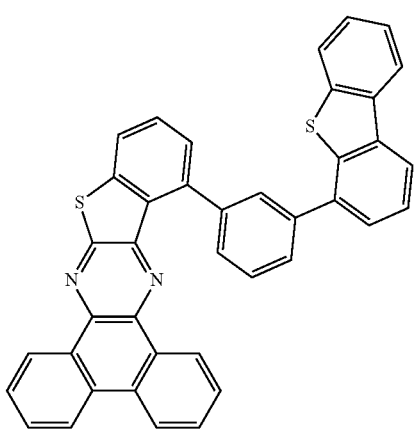
(166)
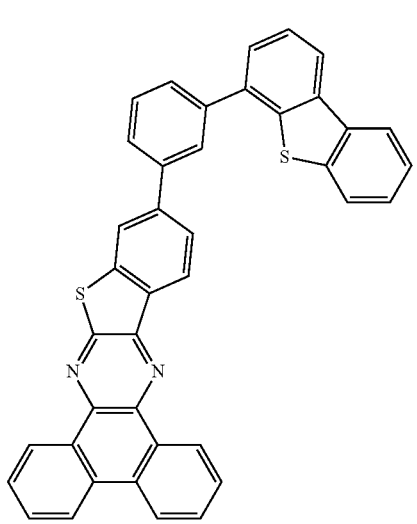

(167)
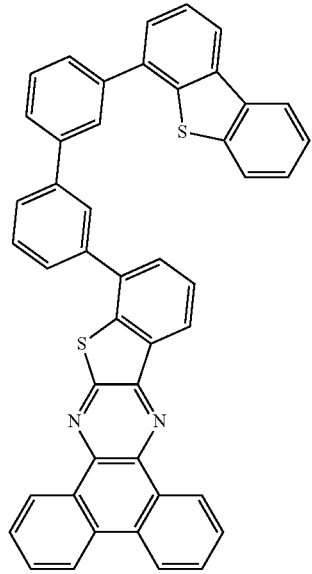
(168)
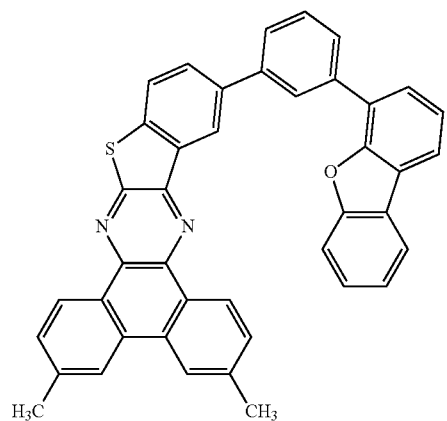
(169)
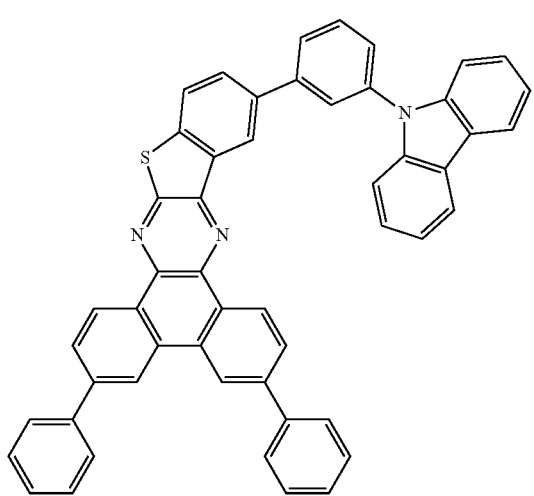
(170)
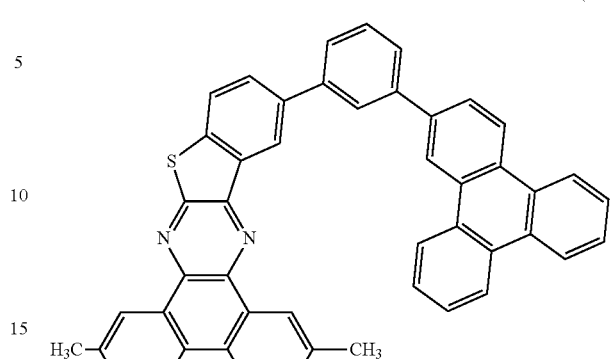
(171)
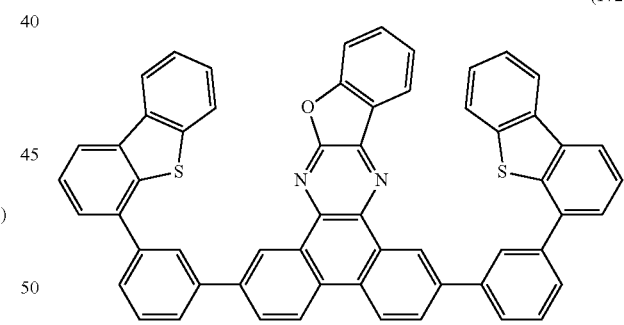
(172)
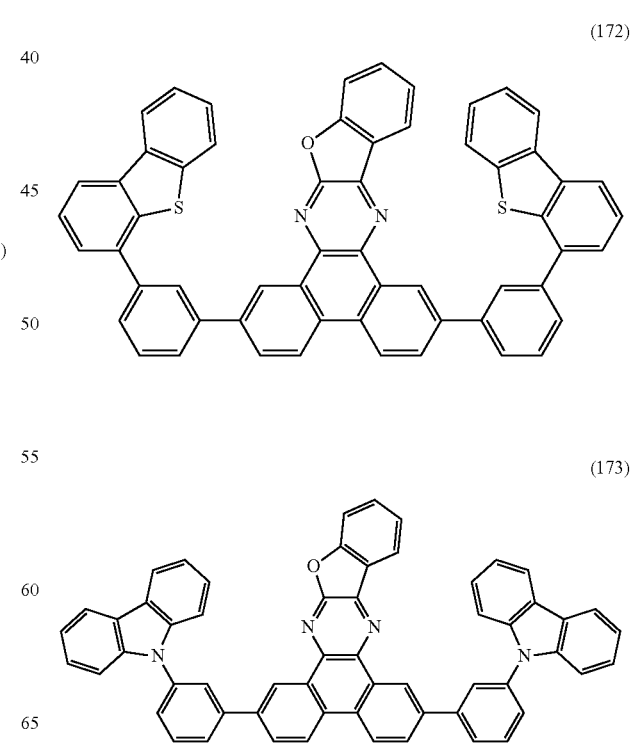
(173)
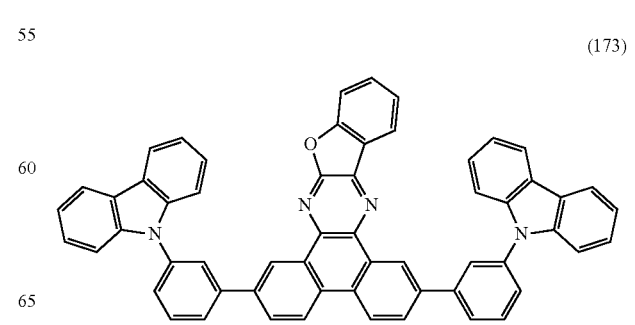

-continued

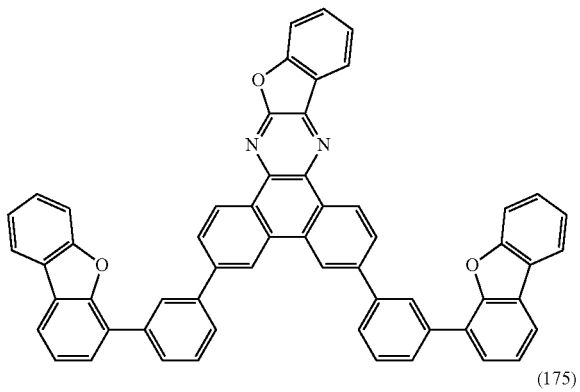

(174)

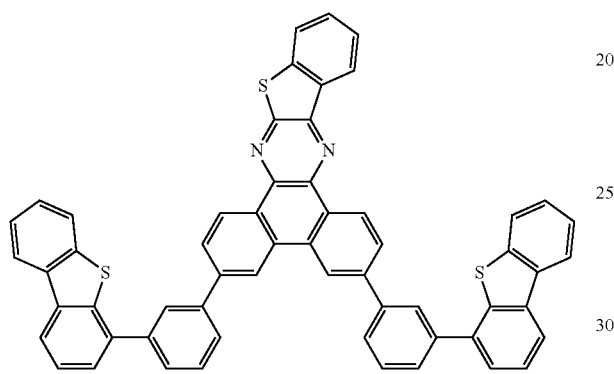

(175)

Note that the organic compounds represented by Structural Formulae (100) to (175) are examples of the organic compound represented by General Formula (G1). The organic compound of one embodiment of the present invention is not limited thereto.

Next, an example of a method for synthesizing the organic compound of one embodiment of the present invention represented by General Formula (G1) will be described.

First, an example of a method for synthesizing a dibenzobenzofuroquinoxaline derivative or a dibenzobenzothienoquinoxaline derivative which is the organic compound represented by General Formula (G1) below will be described.

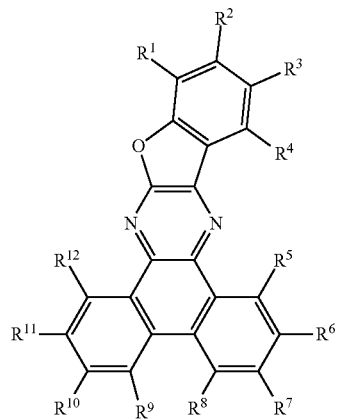

(G1)

In General Formula (G1), Q represents O or S, $R^1$ to $R^{12}$ each independently represent hydrogen or a substituent, and at least one of $R^1$ to $R^{12}$ represents a substituted or unsubstituted condensed aromatic ring or condensed heteroaromatic ring having 3 to 30 carbon atoms.

<<Method for Synthesizing Halogen Compound Represented by General Formula (G0)>>

First, a method for synthesizing a halogen compound (General Formula (G0)) that is used for synthesis of the dibenzobenzofuroquinoxaline derivative or the dibenzobenzothienoquinoxaline derivative, which is represented by General Formula (G1), will be described.

The halogen compound represented by General Formula (G0) below can be easily synthesized by the synthesis method below, for example. Here, a first synthesis method and a second synthesis method will be described.

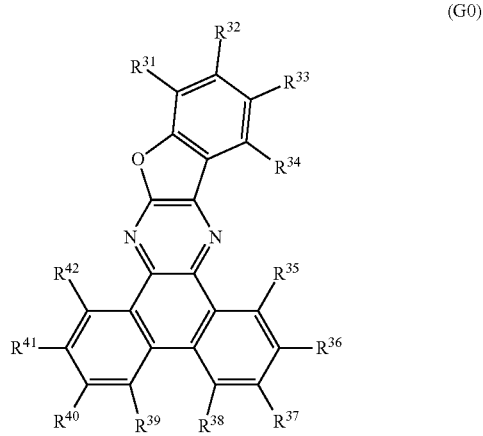

(G0)

In General Formula (G0), Q represents O or S, $R^{31}$ to $R^{42}$ each independently represent hydrogen or a substituent, and at least one of $R^{31}$ to $R^{42}$ represents halogen.

<First Synthesis Method>

The halogen compound represented by General Formula (G0) can be obtained by reacting a halogenated dibenzoquinoxaline derivative (A1) having a phenyl group to which a hydroxy group or a sulfanyl group is bonded, with a base (A2) such as potassium carbonate, as shown in Synthesis Scheme (A-1) below.

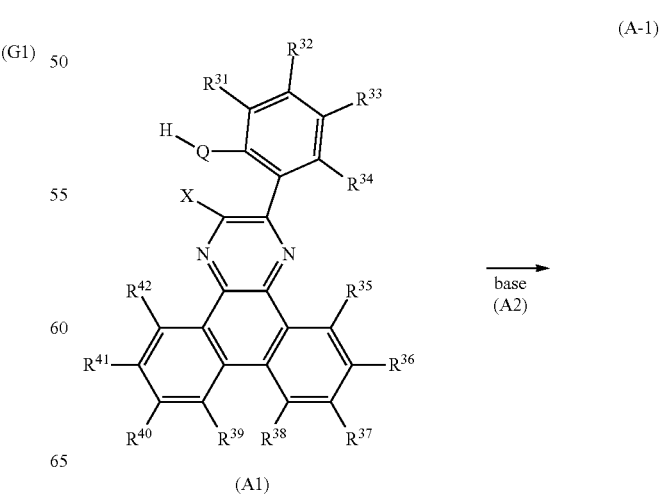

(A-1)

(A1)

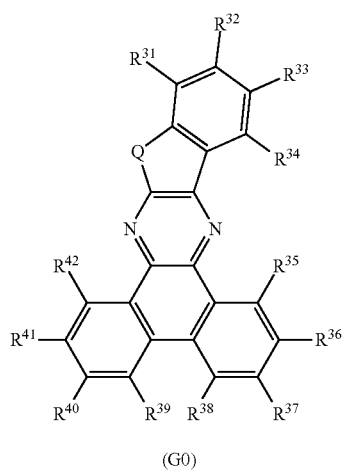

(G0)

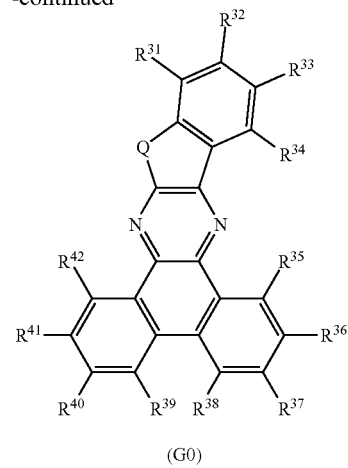

(G0)

Note that in Synthesis Scheme (A-1), Q represents O or S, X represents halogen, $R^{31}$ to $R^{42}$ each independently represent hydrogen or a substituent, and at least one of $R^{31}$ to $R^{42}$ represents halogen.

<Second Synthesis Method>

The halogen compound represented by General Formula (G0) can also be obtained by reacting a phenyl group to which a methyloxy group or a methylsulfanyl group is bonded, a dibenzoquinoxaline derivative (A1') having an amino group, and tert-butyl nitrite with one another as shown in Synthesis Scheme (A-1') below.

Note that in Synthesis Scheme (A-1'), Q represents O or S, $R^3$ to $R^{42}$ each independently represent hydrogen or a substituent, and at least one of $R^3$ to $R^{42}$ represents halogen.

<<Method for Synthesizing Organic Compound Represented by General Formula (G1)>>

Next, a method for synthesizing the dibenzobenzofuroquinoxaline derivatives or the dibenzobenzothienoquinoxaline derivatives, which are represented by General Formula (G1), will be described.

The dibenzobenzofuroquinoxaline derivatives or the dibenzobenzothienoquinoxaline derivatives, which are represented by General Formula (G1), can be obtained by coupling the halogen compound (G0) obtained by the above scheme (A-1) or (A-1') and a boronic acid compound (B1), as shown in Synthesis Scheme (A-2) below.

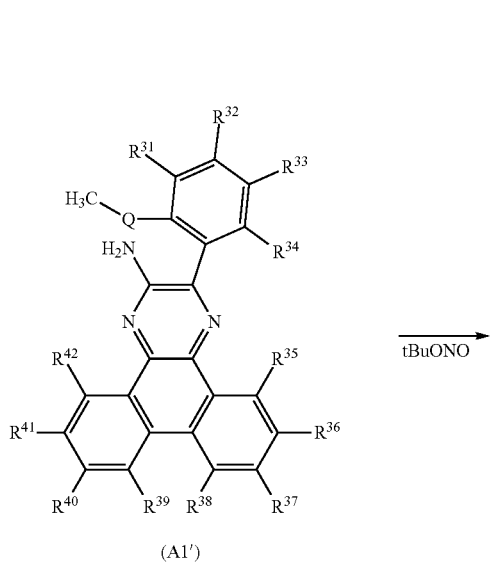

(A1')

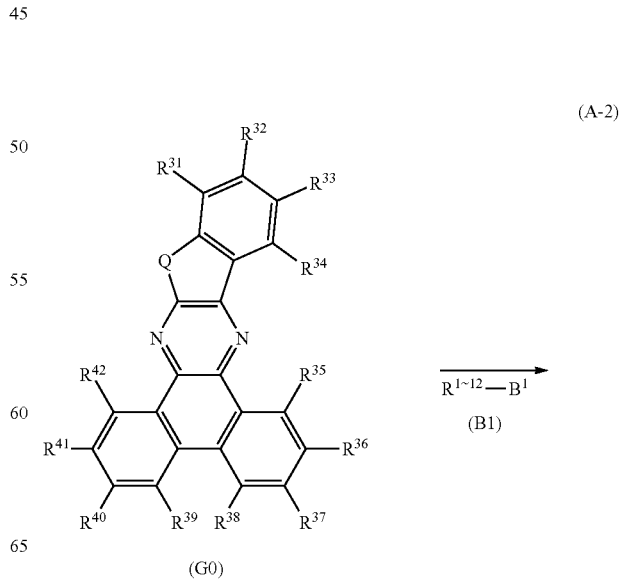

(A-2)

(G0)

-continued

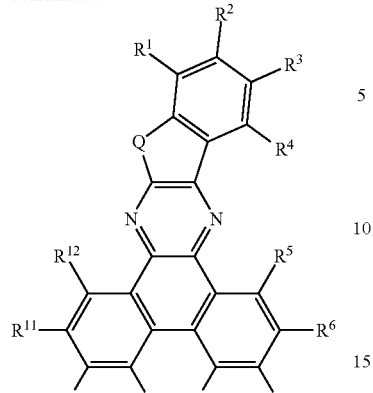

(G1)

Note that in Synthesis Scheme (A-2), Q represents O or S, $R^1$ to $R^{12}$ and $R^{31}$ to $R^{42}$ each independently represent hydrogen or a substituent, and at least one of $R^1$ to $R^{12}$ has a substituted or unsubstituted condensed aromatic ring or condensed heteroaromatic ring having 3 to 30 carbon atoms. $B^1$ represents a boronic acid, a boronic ester, a cyclic-triolborate salt, or the like.

Since various kinds of compounds are commercially available as the compounds (A1) and (A1') above or as the compounds (A1) and (A1') can be synthesized, many kinds of organic compounds can be synthesized as the dibenzo-benzofuroquinoxaline derivative or the dibenzobenzothienoquinoxaline derivative of one embodiment of the present invention, which is represented by General Formula (G1). Thus, the organic compound of one embodiment of the present invention is rich in variety.

Specific structural formulae of the above compound (G0) are shown below.

(200)

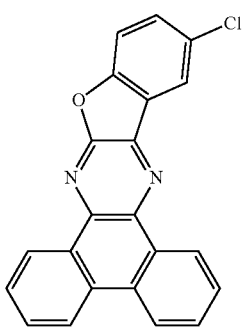

(201)

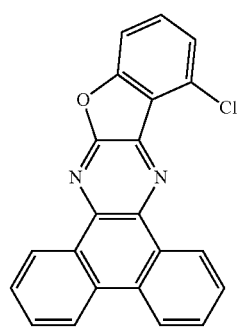

(202)

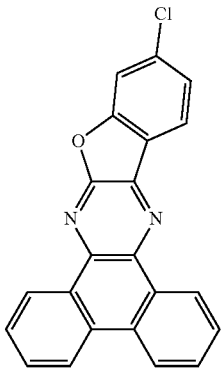

(203)

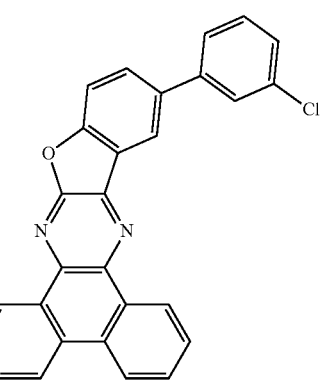

(204)

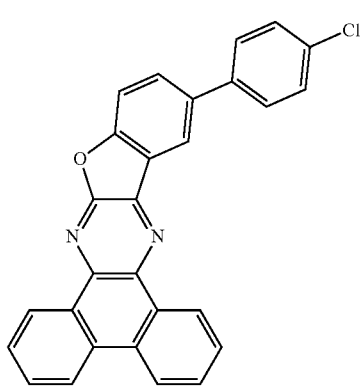

(205)

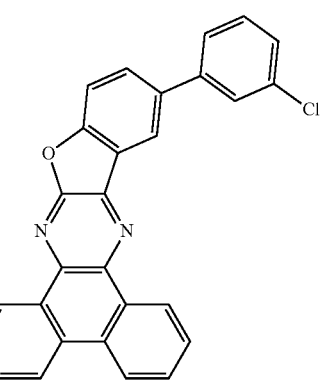

(206) 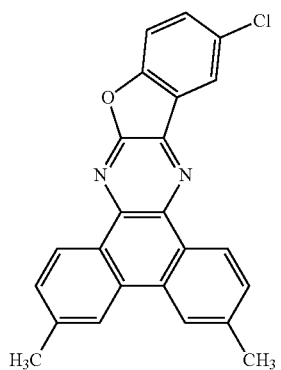
(207) 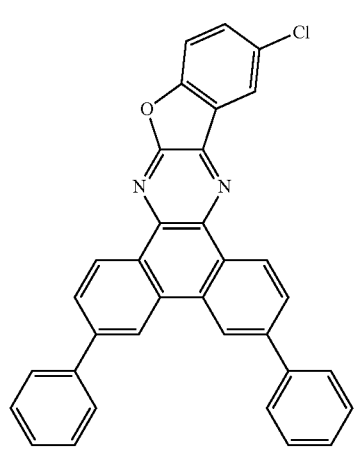
(208) 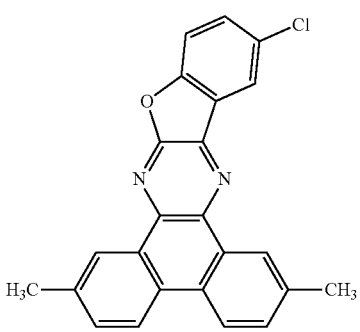
(209) 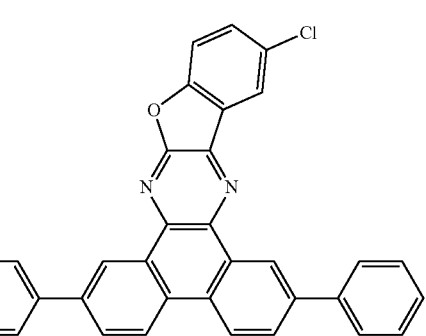
(210) 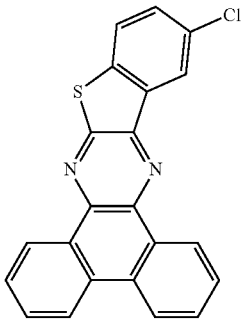
(211) 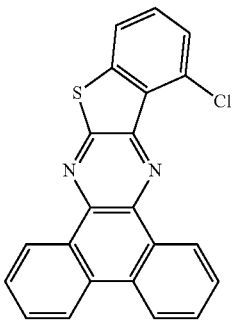
(212) 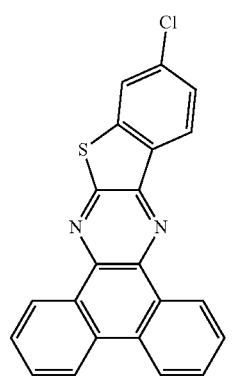
(213) 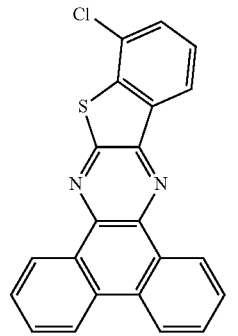

(214) 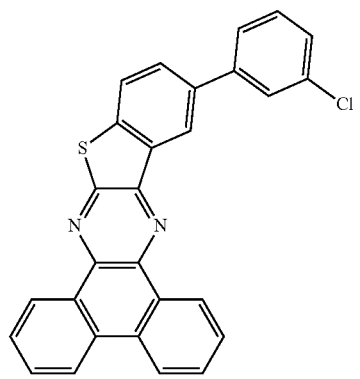
(215) 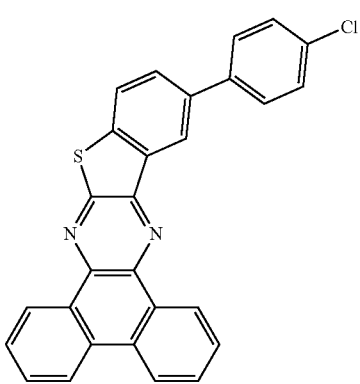
(216) 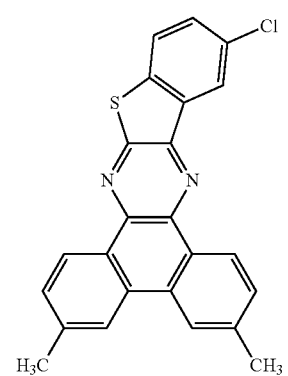
(217) 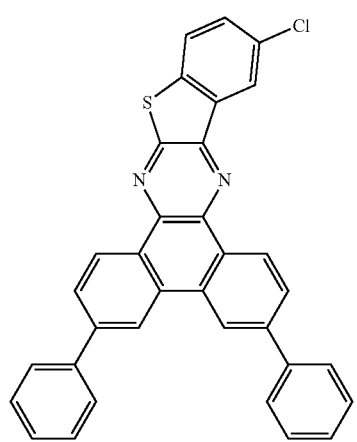
(218) 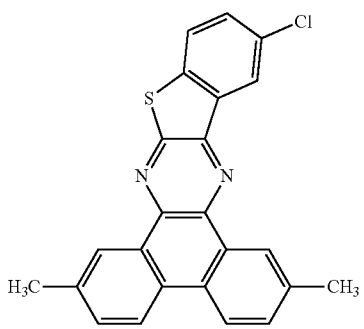
(219)
(220)
(221) 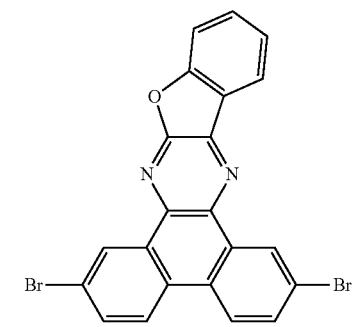

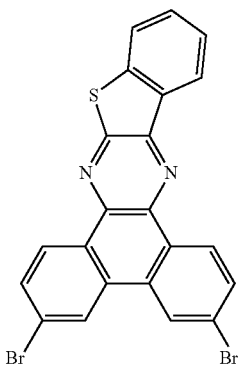

(222)

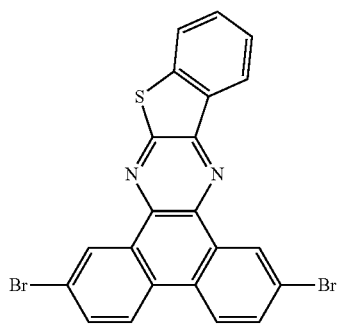

(223)

The organic compounds represented by Structural Formulae (200) to (223) are examples of the halogen compound represented by General Formula (G0). The organic compound of one embodiment of the present invention is not limited thereto.

Described above is an example of the method for synthesizing the dibenzobenzofuroquinoxaline derivative or the dibenzobenzothienoquinoxaline derivative, which is the organic compound of one embodiment of the present invention. The present invention is not limited to this example and any other synthesis method may be employed.

Note that the organic compound described in this embodiment can be used in combination with any of the structures described in the other embodiments as appropriate.

Note that the above organic compounds of embodiments of the present invention each have an electron-transport property and a hole-transport property and thus can be used as a host material in a light-emitting layer or can be used in an electron-transport layer or a hole-transport layer. The organic compounds of embodiments of the present invention can each keep a relatively high T1 level and thus is preferably used as a host material in combination with a substance that emits phosphorescence (phosphorescent material). In addition, the above organic compounds emit fluorescence and can thus be used as light-emitting substances of light-emitting elements. Accordingly, light-emitting elements containing these organic compounds are also included as embodiments of the present invention.

The organic compounds of embodiments of the present invention each have a low LUMO level and thus are preferable as the compound that easily accepts electrons. Thus, the organic compounds are preferably used as a host material in an electron-transport layer or a light-emitting layer, in which case the drive voltage of the light-emitting element can be reduced.

Note that when a combination of the organic compound of one embodiment of the present invention and an organic compound that has a high HOMO level (specifically, greater than or equal to −5.7 eV) and easily accepts holes is used, an exciplex can be formed and excitation energy can be efficiently transferred from the exciplex to a light-emitting substance; consequently, the efficiency and reliability of a phosphorescent light-emitting element can be increased and the drive voltage of the phosphorescent light-emitting element can be reduced. For specific examples of organic compounds (a hole-transport material and an electron-transport material) which are used in combination with the organic compound of one embodiment of the present invention, any of the materials described in Embodiment 2 can be used as appropriate.

With the use of the organic compound of one embodiment of the present invention, a light-emitting element, a light-emitting device, an electronic device, or a lighting device having high emission efficiency can be fabricated. Furthermore, a light-emitting element, a light-emitting device, an electronic device, or a lighting device with low power consumption can be fabricated.

In Embodiment 1, one embodiment of the present invention has been described. Other embodiments of the present invention will be described in the other embodiments. Note that one embodiment of the present invention is not limited thereto. In other words, various embodiments of the invention are described in this embodiment and the other embodiments, and one embodiment of the present invention is not limited to a particular embodiment. For example, although the example in which one embodiment of the present invention is applied to a light-emitting element is described, one embodiment of the present invention is not limited thereto. Depending on circumstances or conditions, one embodiment of the present invention may be applied to objects other than a light-emitting element. Furthermore, depending on circumstances or conditions, one embodiment of the present invention need not be applied to a light-emitting element.

The structure described in this embodiment can be used in combination with any of the structures described in the other embodiments, as appropriate.

Embodiment 2

In this embodiment, light-emitting elements of embodiments of the present invention will be described. For the light-emitting element described in this embodiment, the organic compound of one embodiment of the present invention can be used.

<<Basic Structure of Light-Emitting Element>>

FIG. 1A illustrates a light-emitting element including, between a pair of electrodes, an EL layer. Specifically, an EL layer 103 including a light-emitting layer is provided between a first electrode 101 and a second electrode 102.

Figure 1B:
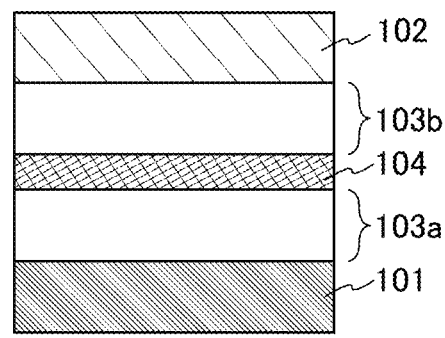

FIG. 1B illustrates a light-emitting element that has a stacked-layer structure (tandem structure) in which a plurality of EL layers (two EL layers 103a and 103b in FIG. 1B) are provided between a pair of electrodes and a charge-generation layer 104 is provided between the EL layers. With the use of such a tandem light-emitting element, a light-emitting device which can be driven at low voltage with low power consumption can be obtained.

The charge-generation layer 104 has a function of injecting electrons into one of the EL layers (103a or 103b) and injecting holes into the other of the EL layers (103b or 103a) when voltage is applied between the first electrode 101 and the second electrode 102. Thus, in FIG. 1B, when voltage is applied such that the potential of the first electrode 101 becomes higher than that of the second electrode 102, the charge-generation layer 104 injects electrons into the EL layer 103a and injects holes into the EL layer 103b.

In terms of light extraction efficiency, the charge-generation layer 104 preferably has a property of transmitting visible light (specifically, the charge-generation layer 104 has a visible light transmittance of 40% or more). The charge-generation layer 104 functions even when having lower conductivity than the first electrode 101 or the second electrode 102.

Figure 1C:
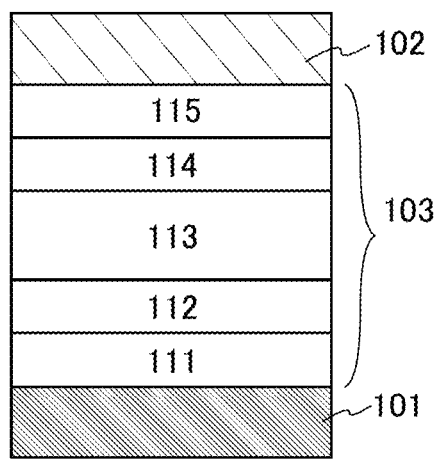

FIG. 1C illustrates a stacked-layer structure of the EL layer 103. In FIG. 1C, in the case where the first electrode 101 functions as an anode, the EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1B, the layers in each EL layer are sequentially stacked from the anode side as described above and illustrated in FIG. 1D. When the first electrode 101 is a cathode and the second electrode 102 is an anode, the stacking order is reversed.

Figure 1D:
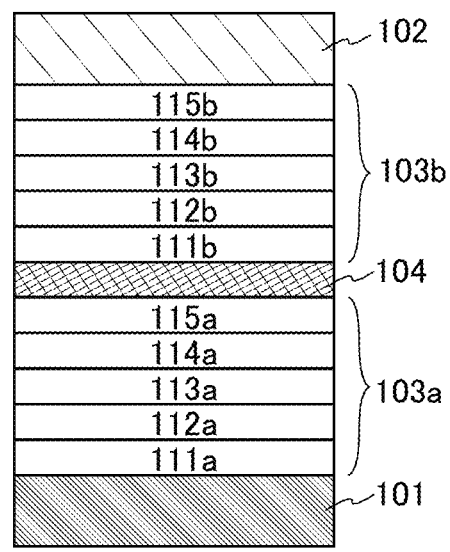
Figure 1E:
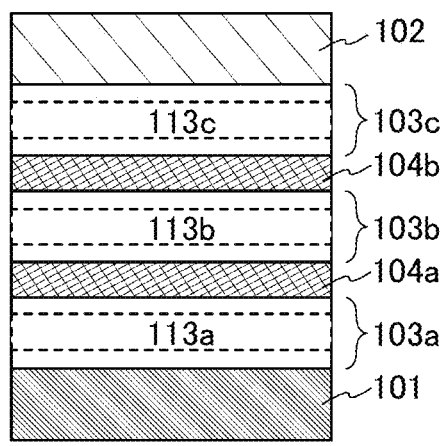

In the case where a plurality of EL layers are stacked, three EL layers (103a, 103b, and 103c) may be stacked and separated by charge-generation layers (104a and 104b) as illustrated in FIG. 1E. Note that the number of stacked layers is not limited to two or three and may be four or more. The light-emitting layers (113, 113a, 113b, and 113c) included in the EL layers (103, 103a, 103b, and 103c) each contain an appropriate combination of a light-emitting substance and a plurality of substances, so that fluorescence or phosphorescence of a desired emission color can be obtained. In the case where a plurality of light-emitting layers 113 (113a, 113b, and 113c) are provided, the light-emitting layers may have respective emission colors. In that case, the light-emitting substance and other substances are different between the stacked light-emitting layers. For example, the light-emitting layer 113a can emit blue light, the light-emitting layer 113b can emit red light, green light, or yellow light, and the light-emitting layer 113c can emit blue light. For another example, the light-emitting layer 113a can emit red light, the light-emitting layer 113b can emit blue light, green light, or yellow light, and the light-emitting layer 113c can emit red light. Note that another combination of emission colors can be employed as appropriate in consideration of luminance and color characteristics of the emission.

In the light-emitting element of one embodiment of the present invention, light emitted from the EL layers (103, 103a, and 103b) can be resonated between the electrodes so that the obtained light emission is intensified. For example, in FIG. 1C, the light-emitting element can have a micro optical resonator (microcavity) structure when the first electrode 101 is a reflective electrode and the second electrode 102 is a transflective electrode, in which case light emission obtained from the EL layer 103 can be intensified.

Note that when the first electrode 101 of the light-emitting element is a reflective electrode having a stacked structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

In the case where the light-emitting element in FIG. 1C has a microcavity structure, light (monochromatic light) with different wavelengths can be extracted even when the same EL layer is used. Thus, separate coloring for obtaining different emission colors (e.g., R, G, and B) is not necessary. Therefore, high resolution can be achieved. Note that a combination with coloring layers (color filters) is also possible. Furthermore, the emission intensity of light with a specific wavelength in the front direction can be increased, whereby power consumption can be reduced.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, preferably higher than or equal to 40% and lower than or equal to 70%. These electrodes preferably have a resistivity of $1\times10^{-2}$ $\Omega$cm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ $\Omega$cm or less.

<<Specific Structure and Fabrication Method of Light-Emitting Element>>

Next, specific structures and fabrication methods of light-emitting elements of embodiments of the present invention will be described. Note that portions denoted by the same reference numeral in FIGS. 1A to 1D can be described in the same way.

<First Electrode and Second Electrode>

As materials used for the first electrode 101 and the second electrode 102, any of the following materials can be used in an appropriate combination as long as the functions of the electrodes in the element structure described above can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

When the light-emitting element includes the EL layer 103 having a stacked-layer structure as in FIG. 1C and the first electrode 101 serving as an anode, the hole-injection layer 111 and the hole-transport layer 112 of the EL layer 103 are sequentially stacked over the first electrode 101 by a vacuum evaporation method. When a plurality of EL layers (103a and 103b) each having a stacked-layer structure are stacked with the charge-generation layer 104 therebetween as in FIG. 1D and the first electrode 101 is an anode, a hole-injection layer 111a and a hole-transport layer 112a of the EL layer 103a are sequentially stacked over the first electrode 101 by a vacuum evaporation method. After the EL layer 103a and the charge-generation layer 104 are sequentially stacked, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) inject holes from the first electrode 101 serving as an anode and the charge-generation layer (104) to the EL layers (103, 103a, and 103b) and each contain a material with a high hole-injection property.

As examples of the material with a high hole-injection property, transition metal oxides such as a molybdenum oxide, a vanadium oxide, a ruthenium oxide, a tungsten oxide, and a manganese oxide can be given. It is also possible to use any of phthalocyanine-based compounds such as phthalocyanine (abbreviation: $H_2Pc$) and copper phthalocyanine (abbreviation: CuPc).

Other examples include aromatic amine compounds, which are low molecular compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples include high molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), can be used.

Alternatively, as the material with a high hole-injection property, a composite material containing a hole-transport material and an acceptor material (an electron-accepting material) can be used. In that case, the acceptor material extracts electrons from the hole-transport material, so that holes are generated in the hole-injection layers (111, 111a, and 111b) and the holes are injected into the light-emitting layers (113, 113a, 113b, and 113c) through the hole-transport layers (112, 112a, and 112b). Note that each of the hole-injection layers (111, 111a, and 111b) may be formed to have a single-layer structure using a composite material containing a hole-transport material and an acceptor material (electron-accepting material), or a stacked-layer structure of a layer including a hole-transport material and a layer including an acceptor material (electron-accepting material).

The hole-transport layers (112, 112a, and 112b) transport the holes, which are injected from the first electrode 101 and the charge-generation layer 104 by the hole-injection layers (111, 111a, and 111b), to the light-emitting layers (113, 113a, 113b, and 113c). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 111a, and 111b) include an oxide of a metal belonging to any of Groups 4 to 8 of the periodic table. Specific examples include molybdenum oxide, vanadium oxide, niobium oxide, tantalum oxide, chromium oxide, tungsten oxide, manganese oxide, and rhenium oxide. Among these oxides, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), and the like can be used. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred. Specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

The hole-transport materials used for the hole-injection layers (111, 111a, and 111b) and the hole-transport layers (112, 112a, and 112b) preferably have a hole mobility of greater than or equal to $1 \times 10^{-6}$ cm$^2$/Vs. Note that other substances may be used as long as the substances have a hole-transport property higher than an electron-transport property.

As the hole-transport materials, materials each having a high hole-transport property, such as a π-electron rich heteroaromatic compound (e.g., a compound having a carbazole skeleton and a compound having a furan skeleton) and a compound having an aromatic amine skeleton, are preferable.

Specific examples of the hole-transport materials include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[M-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N'-triphenyl-N,N,N'-tris(9-phenylcarbazol-3-yl)benzene-1,3,5-tri amine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples include compounds each having an aromatic amine skeleton, such as 3-[4-(1-naphthyl)-phenyl]-9-phenyl-9H-carbazole (abbreviation: PCPN), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N,N'-diphenyl-p-phenylenedi amine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B), compounds each having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(4-diphenyl aminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA), compounds each having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), and compounds each having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

High molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b). Note that the hole-transport layers (112, 112a, and 112b) may each be formed of a plurality of layers. That is, for example, the hole-transport layers may each have a stacked-layer structure of a first hole-transport layer and a second hole-transport layer.

In the light-emitting element in FIG. 1D, the light-emitting layer 113a is formed over the hole-transport layer 112a of the EL layer 103a by a vacuum evaporation method. After the EL layer 103a and the charge-generation layer 104 are formed, the light-emitting layer 113b is formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a, 113b, and 113c) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

The light-emitting layers (113, 113a, 113b, and 113c) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

The light-emitting substance that can be used for the light-emitting layers (113, 113a, 113b, and 113c) is not particularly limited, and a light-emitting substance that converts singlet excitation energy into light emission in the visible light range or a light-emitting substance that converts triplet excitation energy into light emission in the visible light range can be used. The organic compound of one embodiment of the present invention emits fluorescence and thus can be used as the light-emitting substance that converts singlet excitation energy into light emission in the visible light range. Other examples of the above light-emitting substances are given below.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is selected appropriately according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: Firpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)) can be given.

As examples of a phosphorescent material which emits green or yellow light and whose emission spectrum has a peak wavelength at greater than or equal to 495 nm and less than or equal to 590 nm, the following substances can be given.

For example, organometallic complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN³]phenyl-κC}iridium(III) (abbreviation: [Ir(dmppm-dmp)₂(acac)]), and (acetylacetonato)bis(4,6-diphenylpyrimidinato)iridium(III) (abbreviation: [Ir(dppm)₂(acac)]); organometallic complexes having a pyrazine skeleton, such as (acetylacetonato)bis(3,5-dimethyl-2-phenylpyrazinato)iridium(III) (abbreviation: [Ir(mppr-Me)₂(acac)]) and (acetylacetonato)bis(5-isopropyl-3-methyl-2-phenylpyrazinato)iridium(III) (abbreviation: [Ir(mppr-iPr)₂(acac)]); organometallic complexes having a pyridine skeleton, such as tris(2-phenylpyridinato-N,C²')iridium(III) (abbreviation: [Ir(ppy)₃]), bis(2-phenylpyridinato-N,C²')iridium(III) acetylacetonate (abbreviation: [Ir(ppy)₂(acac)]), bis(benzo[h]quinolinato)iridium(III) acetylacetonate (abbreviation: [Ir(bzq)₂(acac)]), tris(benzo[h]quinolinato)iridium(III) (abbreviation: [Ir(bzq)₃]), tris(2-phenylquinolinato-N,C²')iridium(III) (abbreviation: [Ir(pq)₃]), and bis(2-phenylquinolinato-N,C²')iridium(III) acetylacetonate (abbreviation: [Ir(pq)₂(acac)]); organometallic complexes such as bis(2,4-diphenyl-1,3-oxazolato-N,C²')iridium(III) acetylacetonate (abbreviation: [Ir(dpo)₂(acac)]), bis {2-[4'-(perfluorophenyl)phenyl]pyridinato-N,C²'}iridium(III) acetylacetonate (abbreviation: [Ir(p-PF-ph)₂(acac)]), and bis(2-phenylbenzothiazolato-N,C²')iridium(III) acetylacetonate (abbreviation: [Ir(bt)₂(acac)]); and a rare earth metal complex such as tris(acetylacetonato)(monophenanthroline)terbium(III) (abbreviation: [Tb(acac)₃(Phen)]) can be given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), and (dipivaloylmethanato)bis[4,6-di(naphthalen-1-yl)pyrimidinato]iridium(III) (abbreviation: [Ir(d1npm)₂(dpm)]); organometallic complexes having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), and (acetylacetonato)bis[2,3-bis(4-fluorophenyl)quinoxalinato]iridium(III) (abbreviation: [Ir(Fdpq)₂(acac)]); organometallic complexes having a pyridine skeleton, such as tris(1-phenylisoquinolinato-N,C²')iridium(III) (abbreviation: [Ir(pi q)₃]) and bis(1-phenylisoquinolinato-N,C²')iridium(III) acetylacetonate (abbreviation: [Ir(piq)₂(acac)]); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)₃(Phen)]) and tris[1-(2-thenoyl)-3,3,3-trifluoroacetonato](monophenanthroline)europium(III) (abbreviation: [Eu(TTA)₃(Phen)]) can be given.

As the organic compounds (the host material and the assist material) used in the light-emitting layers (113, 113a, 113b, and 113c), one or more kinds of substances having a larger energy gap than the light-emitting substance (the guest material) are used. Note that any of the hole-transport materials listed above and the electron-transport materials given below can be used as the organic compounds (the host material and the assist material). Since the organic compound of one embodiment of the present invention has a low LUMO level, the use of the organic compound as a host material and an assist material can lower the drive voltage. The relatively high T1 level described above is also a characteristic needed for the organic compound. Owing to the low LUMO level, the organic compound can be used in combination with any of a variety of materials, as one of organic compounds that form an exciplex. By giving other materials as examples, the characteristics required for the organic compounds (the host material and the assist material) will be described in detail.

When the light-emitting substance is a fluorescent material, it is preferable to use, as the host material, an organic compound that has a high energy level in a singlet excited state and has a low energy level in a triplet excited state. Note that, in addition to the hole-transport materials and the electron-transport materials described in this embodiment, a bipolar material can be used as the host material, and a substance satisfying the above conditions is preferred. For example, an anthracene derivative and a tetracene derivative are also preferred.

Thus, examples of the host material used in combination with a fluorescent substance include 9-phenyl-3-[4-(10-phenyl-9-anthryl)phenyl]-9H-carbazole (abbreviation: PCzPA), PCPN, CzPA, 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is selected as the host material. Note that, in addition to the hole-transport materials and the electron-transport materials described in this embodiment, a bipolar material can be used as the host material, and a substance satisfying the above conditions is preferred. For example, condensed polycyclic aromatic compounds such as an anthracene derivative, a phenanthrene derivative, a pyrene derivative, a chrysene derivative, and a dibenzo[g,p]chrysene derivative are also preferred.

Thus, examples of the host material used in combination with a phosphorescent substance include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, 9-(4-{4'-[N-phenyl-N—(N-phenyl-3-carbazolyl)]amino}phenyl)phenyl-10-phenylanthracene (abbreviation: PCAPBA), N-(9,10-diphenyl-2-anthryl)-N, 9-diphenyl-9H-carbazol-3-amine (abbreviation: 2PCAPA), 6,12-dimethoxy-5,11-diphenylchrysene, N,N,N',N',N'',N''',N'''-octaphenyldibenzo[g,p]chrysene-2,7,10,15-tetraamine (abbreviation: DBC1), CzPA, 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3).

In the case where a plurality of organic compounds are used for the light-emitting layers (113, 113a, 113b, and 113c), compounds that form an exciplex are preferably used in combination with a phosphorescent substance. With such a structure, light emission can be obtained by exciplex-triplet energy transfer (ExTET), which is energy transfer from an exciplex to a light-emitting substance. In that case, any of various organic compounds can be combined appropriately to be used; to form an exciplex efficiently, it is particularly preferable to combine a compound that easily accepts holes (hole-transport material) and a compound that easily accepts electrons (electron-transport material).

The TADF material can up-convert a triplet excited state into a singlet excited state (i.e., reverse intersystem crossing is possible) using a little thermal energy and efficiently emit light (fluorescence) from the singlet excited state. The TADF is efficiently obtained under the condition where the energy difference between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $1 \times 10^{-6}$ seconds or longer, preferably $1 \times 10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Other examples of the TADF material include heterocyclic compounds each having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), and 10-phenyl-10H,10'H-spiro[acridin-9,9'-anthracen]-10'-one (abbreviation: ACRSA). Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be used in combination with another organic compound.

With the appropriate use of the above materials, the light-emitting layers (113, 113a, 113b, and 113c) can be formed. Furthermore, when used in combination with a low molecular material or a high molecular material, the above materials can be used to form the light-emitting layers (113, 113a, 113b, and 113c).

In the light-emitting element in FIG. 1D, the electron-transport layer 114a is formed over the light-emitting layer 113a of the EL layer 103a. After the EL layer 103a and the charge-generation layer 104 are formed, the electron-transport layer 114b is formed over the light-emitting layer 113b of the EL layer 103b.

<Electron-Transport Layer>

The electron-transport layers (114, 114a, and 114b) transport the electrons, which are injected from the second electrode 102 by the electron-injection layers (115, 115a, and 115b), to the light-emitting layers (113, 113a, 113b, and 113c). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1 \times 10^{-6}$ cm$^2$/Vs. Note that other substances may also be used as long as the substances have an electron-transport property higher than a hole-transport property. The organic compound of one embodiment of the present invention satisfies such requirements. Furthermore, the low LUMO level of the organic compound helps lower the drive voltage; thus, the organic compound is preferably used for the electron-transport layers. Other examples of materials that can be used for the electron-transport layers are given below.

As the electron-transport material, any of the following materials having a high electron-transport property can be used: a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, and a π-electron deficient heteroaromatic compound such as a nitrogen-containing heteroaromatic compound.

Specific examples of the electron-transport material include metal complexes having a quinoline skeleton or a benzoquinoline skeleton, such as tris(8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), bis[2-(2-benzothiazolyl)phenolato]zinc(II) (abbreviation: ZnBTZ), and bis[2-(2-hydroxyphenyl)benzothiazolato]zinc(II) (abbreviation: Zn(BTZ)$_2$).

Other than the metal complexes, it is possible to use oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazol e (abbreviation: CO11); triazole derivatives such as 3-(4'-tert-butylphenyl)-4-phenyl-5-(4''-biphenyl)-1,2,4-triazole (abbreviation: TAZ) and 3-(4-tert-butylphenyl)-4-(4-ethylphenyl)-5-(4-biphenylyl)-1,2,4-triazole (abbreviation: p-EtTAZ); imidazole derivatives (including benzimidazole derivatives) such as 2,2',2''-(1,3, 5-benzenetriyl)tris(1-phenyl-1H-benzimidazole) (abbreviation: TPBI) and 2-[3-(dibenzothiophen-4-yl)phenyl]-1-phenyl-1H-benzimidazole (abbreviation: mDBTBIm-II); an oxazole derivative such as 4,4'-bis(5-methylbenzoxazol-2-yl)stilbene (abbreviation: BzOS); phenanthroline derivatives such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); quinoxaline derivatives and dibenzoquinoxaline derivatives, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II); pyridine derivatives such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB); pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); and triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn) and 9-[3-(4,6-diphenyl-1,3,5-triazin-2-yl)phenyl]-9'-phenyl-2,3'-bi-9H-carbazole (abbreviation: mPCCzPTzn-02).

Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, and may be a stack of two or more layers each containing any of the above substances.

Next, in the light-emitting element in FIG. 1D, the electron-injection layer 115a is formed over the electron-transport layer 114a of the EL layer 103a by a vacuum evaporation method. Subsequently, the EL layer 103a and the charge-generation layer 104 are formed, the components up to the electron-transport layer 114b of the EL layer 103b are formed, and then the electron-injection layer 115b is formed thereover by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride ($CaF_2$), or lithium oxide ($LiO_x$). A rare earth metal compound like erbium fluoride ($ErF_3$) can also be used. Electride may also be used for the electron-injection layers (115, 115a, and 115b). Examples of the electride include a substance in which electrons are added at high concentration to calcium oxide-aluminum oxide. Any of the substances used for the electron-transport layers (114, 114a, and 114b), which are given above, can also be used.

A composite material in which an organic compound and an electron donor (donor) are mixed may also be used for the electron-injection layers (115, 115a, and 115b). Such a composite material has a high electron-injection property and a high electron-transport property because electrons are generated in the organic compound by the electron donor. The organic compound here is preferably a material excellent in transporting the generated electrons; specifically, for example, the electron-transport materials used for the electron-transport layers (114, 114a, and 114b), such as a metal complex or a heteroaromatic compound, can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Still alternatively, an organic compound such as tetrathiafulvalene (abbreviation: TTF) can be used.

In the case where light emitted from the light-emitting layer 113b is amplified in the light-emitting element in FIG. 1D, the optical path length between the second electrode 102 and the light-emitting layer 113b is preferably less than one fourth of the wavelength λ of light emitted from the light-emitting layer 113b. In that case, the optical path length can be adjusted by changing the thickness of the electron-transport layer 114b or the electron-injection layer 115b.

<Charge-Generation Layer>

In the light-emitting element in FIG. 1D, the charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: $F_4$-TCNQ), chloranil, and the like. In addition, oxides of metals that belong to Group 4 to Group 8 of the periodic table can be given. Specific examples are vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

<Substrate>

The light-emitting element described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111*a*, and 111*b*), the hole-transport layers (112, 112*a*, and 112*b*), the light-emitting layers (113, 113*a*, 113*b*, and 113*c*), the electron-transport layers (114, 114*a*, and 114*b*), the electron-injection layers (115, 115*a*, and 115*b*)) included in the EL layers and the charge-generation layers (104, 104*a*, and 104*b*) in the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nanoimprint lithography), or the like.

Note that materials that can be used for the functional layers (the hole-injection layers (111, 111*a*, and 111*b*), the hole-transport layers (112, 112*a*, and 112*b*), the light-emitting layers (113, 113*a*, 113*b*, and 113*c*), the electron-transport layers (114, 114*a*, and 114*b*), and the electron-injection layers (115, 115*a*, and 115*b*)) that are included in the EL layers (103, 103*a*, and 103*b*) and the charge-generation layers (104, 104*a*, and 104*b*) of the light-emitting element described in this embodiment are not limited to the above materials, and other materials can be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

The structures described in this embodiment can be combined with any of the structures described in the other embodiments, as appropriate.

Embodiment 3

Figure 2A:
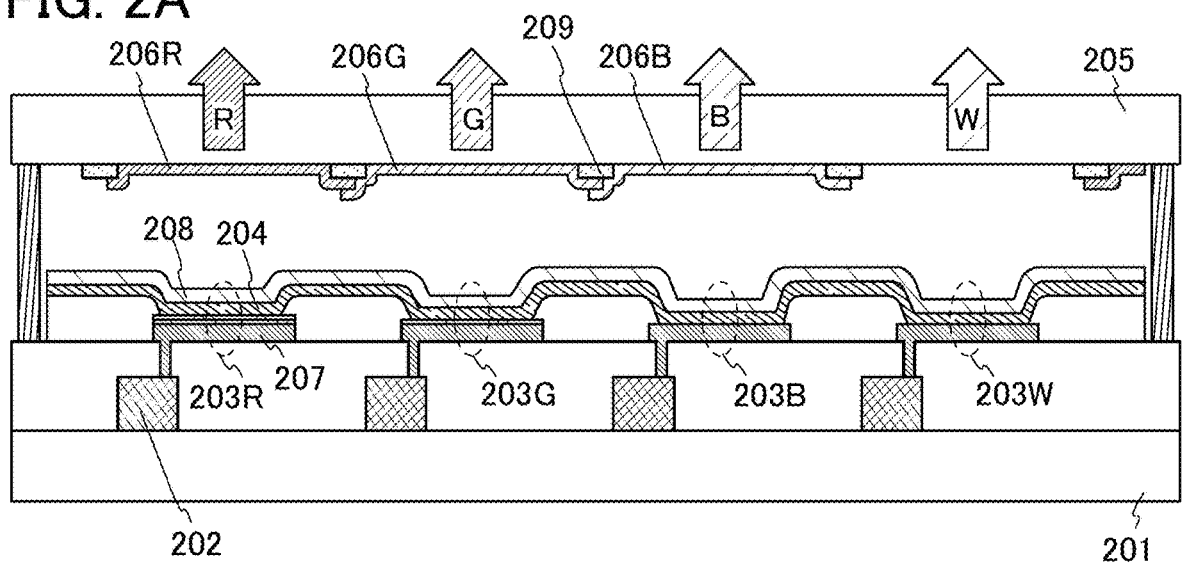
FIGS. 2A to 2C illustrate light-emitting devices.

In this embodiment, a light-emitting device of one embodiment of the present invention will be described. Note that a light-emitting device illustrated in FIG. 2A is an active-matrix light-emitting device in which transistors (FETs) 202 over a first substrate 201 are electrically connected to light-emitting elements (203R, 203G, 203B, and 203W). The light-emitting elements (203R, 203G, 203B, and 203W) include a common EL layer 204 and each have a microcavity structure in which the optical path length between electrodes is adjusted according to the emission color of the light-emitting element. The light-emitting device is a top-emission light-emitting device in which light is emitted from the EL layer 204 through color filters (206R, 206G, and 206B) formed on a second substrate 205.

The light-emitting device illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
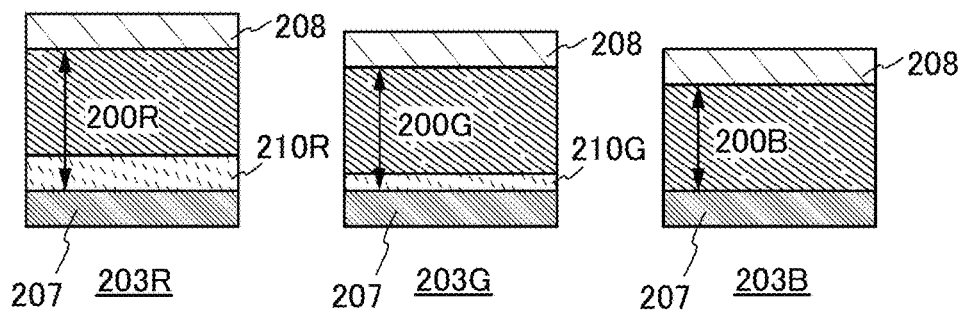

In the case where the light-emitting element 203R functions as a red light-emitting element, the light-emitting element 203G functions as a green light-emitting element, the light-emitting element 203B functions as a blue light-emitting element, and the light-emitting element 203W functions as a white light-emitting element in FIG. 2A, for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2B. Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting element 203R, whereby red light emission can be obtained from the light-emitting element 203R. Furthermore, the color filter 206G that transmits only light in the green wavelength range is provided in a position overlapping with the light-emitting element 203G, whereby green light emission can be obtained from the light-emitting element 203G. Moreover, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
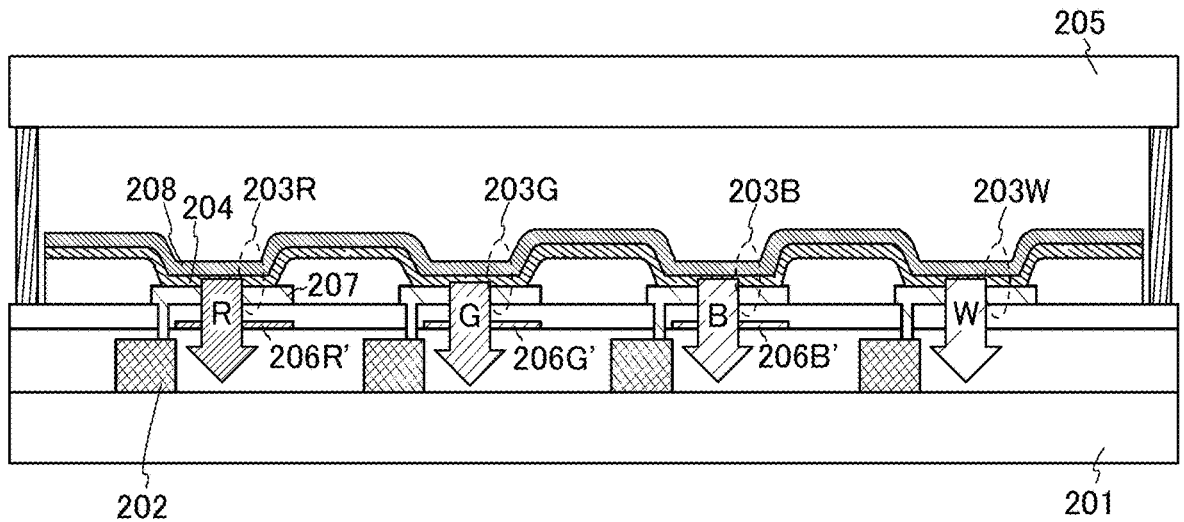

Although the light-emitting device in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting device, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B) are provided closer to the first substrate 201 than the light-emitting elements (203R, 203G, and 203B) are.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected according to the emission color of the light-emitting element.

With the above structure, a light-emitting device including light-emitting elements that exhibit a plurality of emission colors can be fabricated.

Note that the structures described in this embodiment can be combined with any of the structures described in the other embodiments, as appropriate.

Embodiment 4

In this embodiment, a light-emitting device of one embodiment of the present invention will be described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is one embodiment of the present invention. Note that any of the light-emitting elements described in the other embodiments can be used in the light-emitting device described in this embodiment.

In this embodiment, an active-matrix light-emitting device will be described with reference to FIGS. 3A and 3B.

Figure 3A:
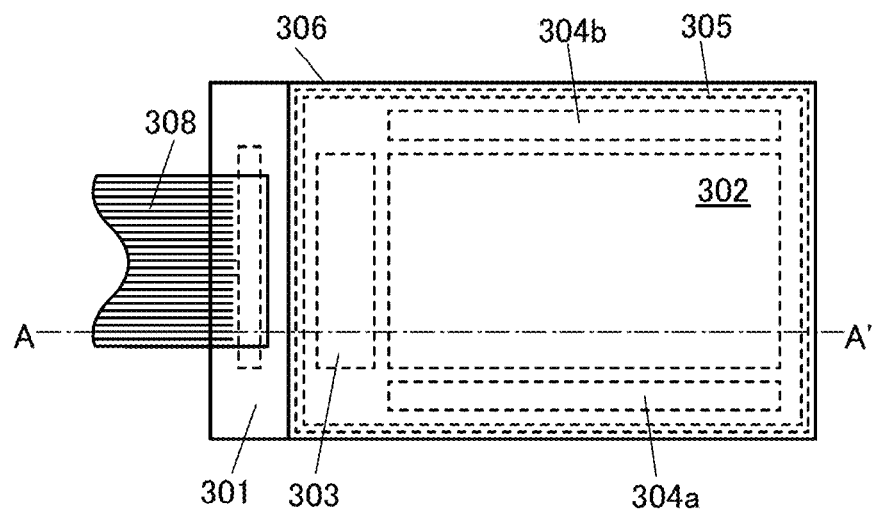
FIGS. 3A and 3B illustrate a light-emitting device.
Figure 3B:
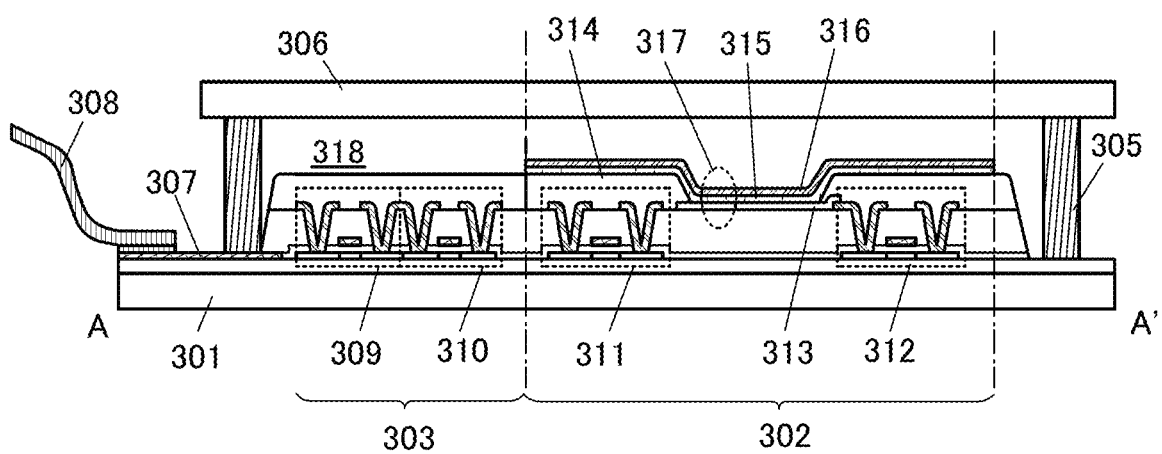

FIG. 3A is a top view illustrating a light-emitting device 21, and FIG. 3B is a cross-sectional view taken along chain line A-A' in FIG. 3A. The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting element 317 described in this embodiment. Although not illustrated, the second electrode 316 is electrically connected to the FPC 308 that is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, an acrylic resin, or the like can be used. In the case where glass frit is used for the sealant, the first substrate 301 and the second substrate 306 are preferably glass substrates in terms of adhesion.

Accordingly, the active-matrix light-emitting device can be obtained.

In the case where the active-matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments, as appropriate.

Embodiment 5

In this embodiment, examples of a variety of electronic devices and an automobile manufactured using the light-emitting element of one embodiment of the present invention or a light-emitting device including the light-emitting element of one embodiment of the present invention will be described. Note that the light-emitting device can be used mainly in a display portion of the electronic device described in this embodiment.

Figure 4A:
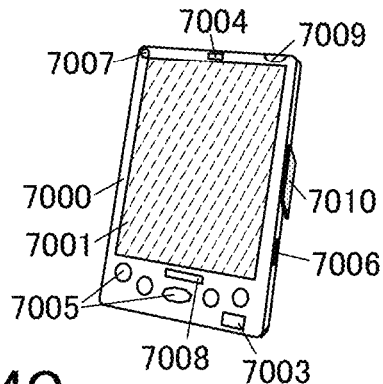
FIGS. 4A to 4G illustrate electronic devices.
Figure 4B:
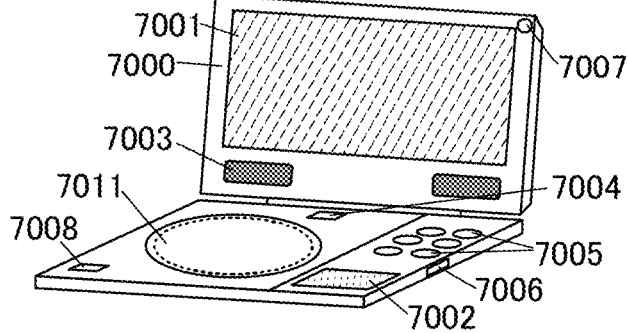
Figure 4C:
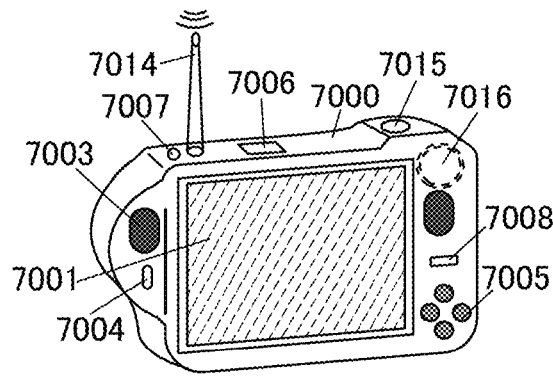

Electronic devices illustrated in FIGS. 4A to 4C can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4A illustrates a mobile computer that can include a switch 7009, an infrared port 7010, and the like in addition to the above components.

FIG. 4B illustrates a portable image reproducing device (e.g., a DVD player) that is provided with a recording medium and can include a second display portion 7002, a recording medium reading portion 7011, and the like in addition to the above components.

FIG. 4C illustrates a digital camera that has a television reception function and can include an antenna 7014, a shutter button 7015, an image receiving portion 7016, and the like in addition to the above components.

Figure 4D:
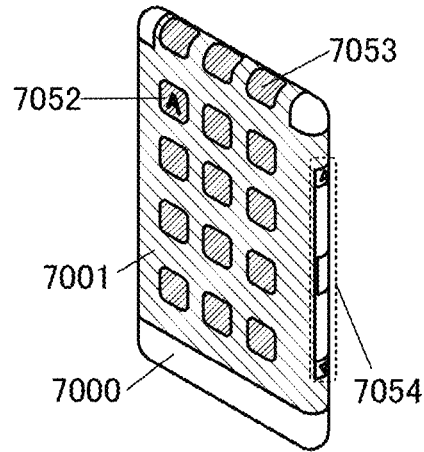

FIG. 4D illustrates a portable information terminal. The portable information terminal has a function of displaying information on three or more surfaces of the display portion 7001. Here, information 7052, information 7053, and information 7054 are displayed on different surfaces. For example, a user of the portable information terminal can check the information 7053 displayed such that it can be seen from above the portable information terminal, with the portable information terminal put in a breast pocket of his/her clothes. Thus, the user can see the display without taking out the portable information terminal from the pocket and decide whether to answer the call, for example.

Figure 4E:
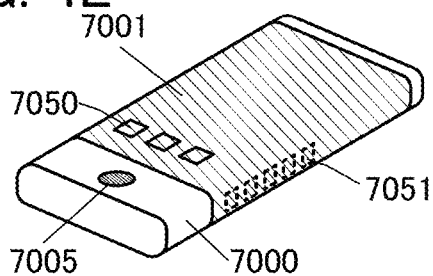

FIG. 4E illustrates a portable information terminal (e.g., a smartphone) and can include the display portion 7001, the operation keys 7005, and the like in the housing 7000. Note that the portable information terminal may include a speaker, a connection terminal, a sensor, or the like. The portable information terminal can display text and image data on its plurality of surfaces. Here, three icons 7050 are displayed. Furthermore, information 7051 indicated by dashed rectangles can be displayed on another surface of the display portion 7001. Examples of the information 7051 include notification of reception of an e-mail, an SNS message, or an incoming call, the title and sender of an e-mail, an SNS message, or the like, the date, the time, remaining battery, and the reception strength of an antenna. The icon 7050 or the like may be displayed at the position where the information 7051 is displayed.

Figure 4F:
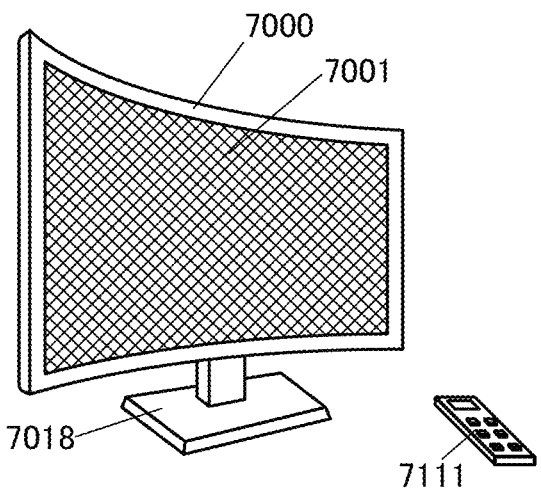

FIG. 4F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 4A to 4F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, the electronic device including a plurality of display portions can have a function of displaying image data mainly on one display portion while displaying text data mainly on another display portion, a function of displaying a three-dimensional image by displaying images on a plurality of display portions with a parallax taken into account, or the like. Furthermore, the electronic device including an image receiving portion can have a function of shooting a still image, a function of shooting a moving image, a function of automatically or manually correcting a taken image, a function of storing a shot image in a recording medium (an external recording medium or a recording medium incorporated in the camera), a function of displaying a shot image on the display portion, or the like. Note that functions that can be provided for the electronic devices illustrated in FIGS. 4A to 4F are not limited to those described above, and the electronic devices can have a variety of functions.

Figure 4G:
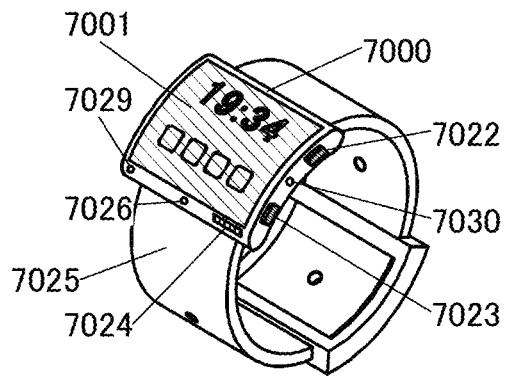

FIG. 4G illustrates a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and images can be displayed on the curved display surface. Furthermore, mutual communication between the portable information terminal and, for example, a headset capable of wireless communication can be performed, and thus hands-free calling is possible with the portable information terminal. Note that the connection terminal 7024 allows mutual data transmission with another information terminal and charging. Wireless power feeding can also be employed for the charging operation.

The display portion 7001 mounted in the housing 7000 serving as a bezel includes a non-rectangular display region. The display portion 7001 can display an icon 7027 indicating time, another icon 7028, and the like. The display portion 7001 may be a touch panel (input/output device) including a touch sensor (input device).

The smart watch illustrated in FIG. 4G can have a variety of functions, such as a function of displaying a variety of information (e.g., a still image, a moving image, and a text image) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting device of one embodiment of the present invention and the display device including the light-emitting element of one embodiment of the present invention can be used in the display portion of each electronic device described in this embodiment, so that a long lifetime electronic device can be obtained.

Figure 5A:
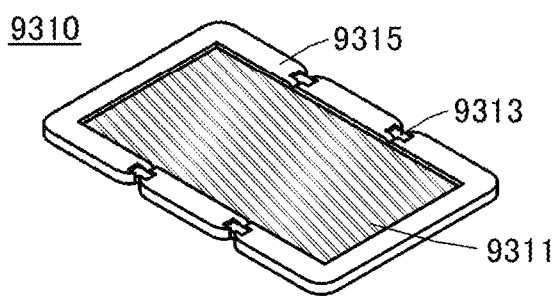
FIGS. 5A to 5C illustrate an electronic device.
Figure 5B:
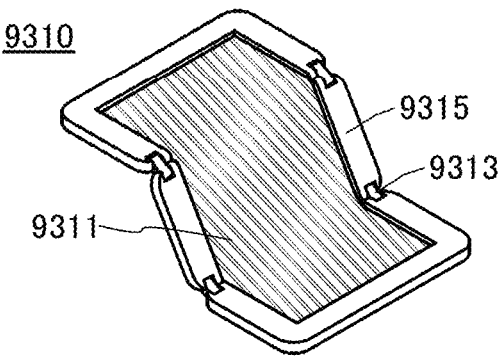
Figure 5C:
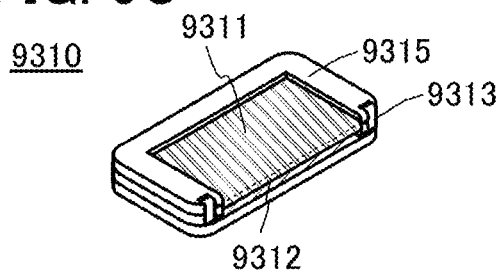

Another electronic device including the light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, a long lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
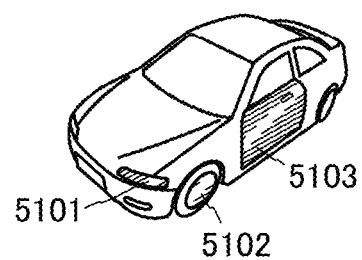
FIGS. 6A and 6B illustrate an automobile.
Figure 6B:
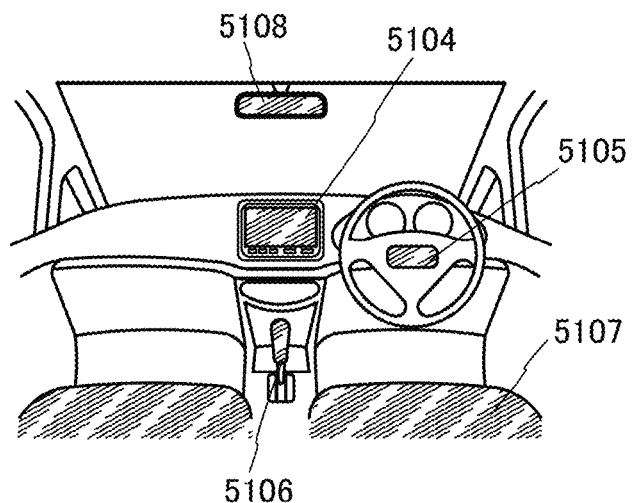

FIGS. 6A and 6B illustrate an automobile including the light-emitting device. The light-emitting device can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

In the above manner, the electronic devices and automobiles can be obtained using the light-emitting device or the display device of one embodiment of the present invention. In that case, a long lifetime electronic device can be obtained. Note that the light-emitting device or the display device can be used for electronic devices and automobiles in a variety of fields without being limited to those described in this embodiment.

Note that the structures described in this embodiment can be combined with any of the structures described in the other embodiments, as appropriate.

Embodiment 6

In this embodiment, the structure of a lighting device fabricated using the light-emitting device of one embodiment of the present invention or the light-emitting element which is part of the light-emitting device will be described with reference to FIGS. 7A and 7B.

Figure 7A:
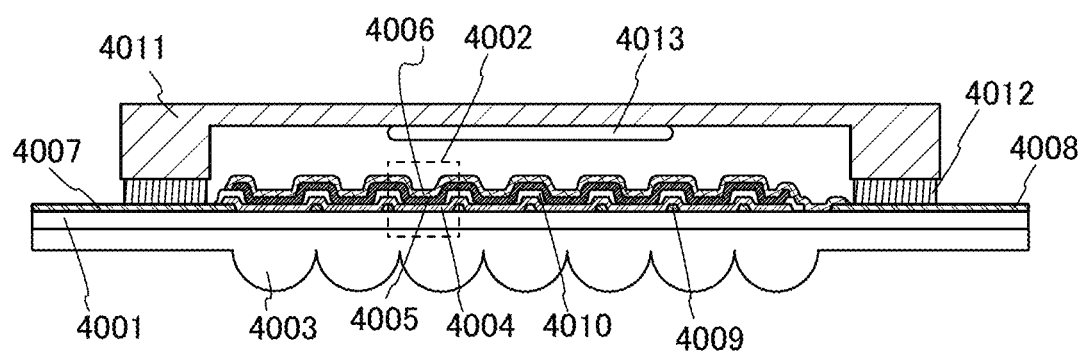
FIGS. 7A and 7B illustrate lighting devices.
Figure 7B:
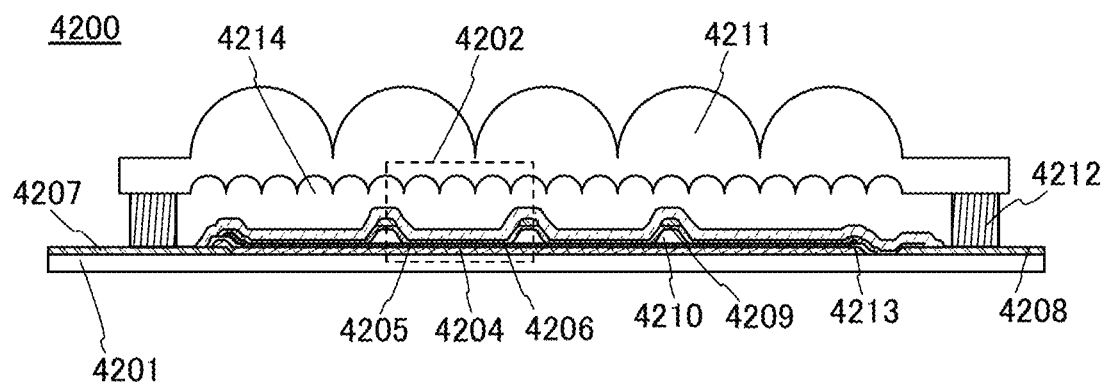
Figure 8:
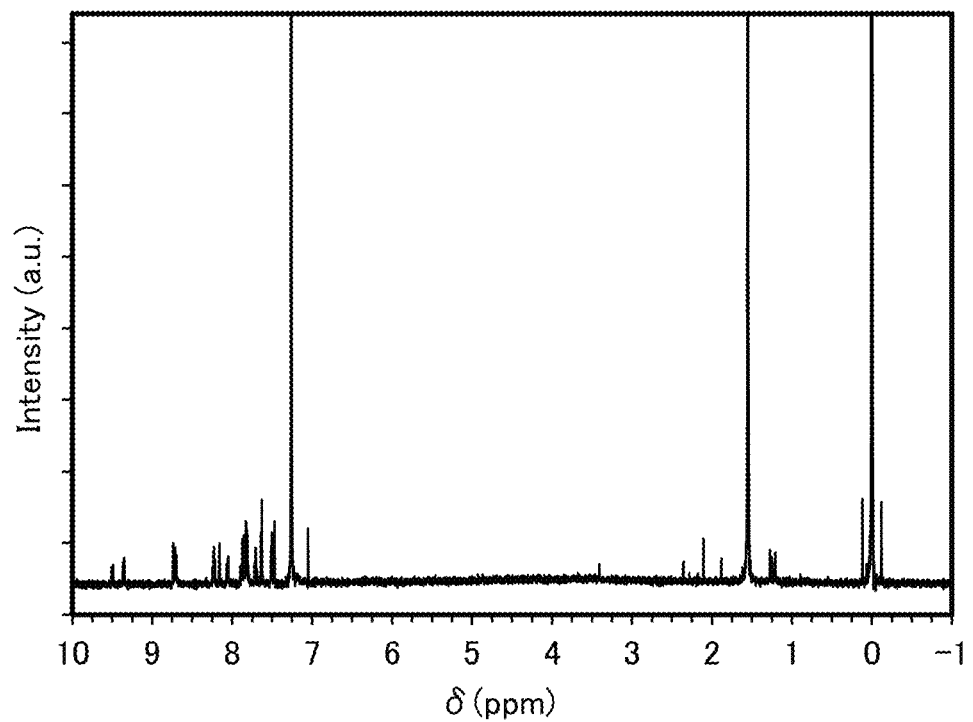
FIG. 8 shows a $^1$H-NMR chart of an organic compound represented by Structural Formula (100).

FIGS. 7A and 7B are examples of cross-sectional views of lighting devices. FIG. 7A illustrates a bottom-emission lighting device in which light is extracted from the substrate side, and FIG. 7B illustrates a top-emission lighting device in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

A lighting device 4200 illustrated in FIG. 7B includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7B, whereby the extraction efficiency of light emitted from the light-emitting element 4202 can be increased.

Examples of such lighting devices include a ceiling light as an indoor lighting. Examples of the ceiling light include a direct-mount light and an embedded light. Such lighting devices are fabricated using the light-emitting device and a housing or a cover in combination.

For another example, such lighting devices can be used for a foot light that lights a floor so that safety on the floor can be improved. A foot light can be effectively used in a bedroom, on a staircase, or on a passage, for example. In that case, the size or shape of the foot light can be changed in accordance with the area or structure of a room. The foot light can be a stationary lighting device fabricated using the light-emitting device and a support in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, when the light-emitting device of one embodiment of the present invention or the light-emitting element which is part of the light-emitting device is used as part of furniture in a room, a lighting device that functions as the furniture can be obtained.

As described above, a variety of lighting devices that include the light-emitting device can be obtained. Note that these lighting devices are also embodiments of the present invention.

Note that the structures described in this embodiment can be used in combination with any of the structures described in the other embodiments, as appropriate.

Example 1

Synthesis Example 1

This example will describe a method for synthesizing 13-[3-(dibenzothiophen-4-yl)phenyl]dibenzo[f,h][1]benzofuro[2,3-b]quinoxaline (abbreviation: 13mDBtPBfdbq), the organic compound of one embodiment of the present invention represented by Structural Formula (100) in Embodiment 1. The structure of 13mDBtPBfdbq is shown below.

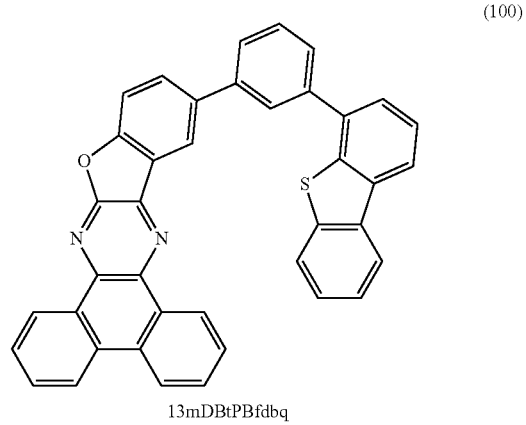

(100)

13mDBtPBfdbq

Step 1: Synthesis of 1,4-dihydrophenanthro[9,10-b]pyrazine-2,3-dione 5.97 g of phenanthrene-9,10-diamine hydrochloride, 16.51 g of sodium hydrogencarbonate, and 230 mL of diethyl oxalate were put into a three-neck flask equipped with a reflux pipe, and the air in the flask was replaced with nitrogen. After that, the mixture was stirred at 130° C. for 23 hours to cause a reaction. After a predetermined time, 1 L of water was added to the reaction solution, and the mixture was stirred at room temperature for 30 minutes. The resulting mixture was suction-filtered and washed with ethanol, so that 3.91 g of a target pyrazine derivative (ocher powder) was obtained in a yield of 61%. A synthesis scheme of Step 1 is shown in (a-1) below.

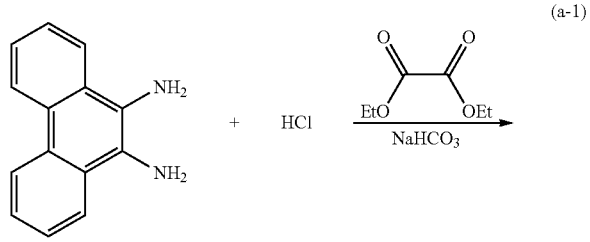

(a-1)

Step 2: Synthesis of 2,3-dichlorodibenzo[f,h]quinoxaline

Next, 3.91 g of 1,4-dihydrophenanthro[9,10-b]pyrazine-2,3-dione obtained in Step 1 and 60 mL of dehydrated DMF were put into a three-neck flask equipped with a reflux pipe, and the air in the flask was replaced with nitrogen. After the flask was cooled with ice, 5.4 mL of phosphoryl chloride was added, and the mixture was stirred at 100° C. for 7.5 hours. After a predetermined time, the resulting mixture was added to 130 mL of a 1M sodium hydroxide aqueous solution, and suction filtration was performed. The resulting solid was washed with water and ethanol and dissolved in toluene, and the mixture was filtered through Celite. The obtained filtrate was concentrated to give 1.00 g of a target quinoxaline derivative (yellowish white powder) in a yield of 22%. A synthesis scheme of Step 2 is shown in (a-2) below.

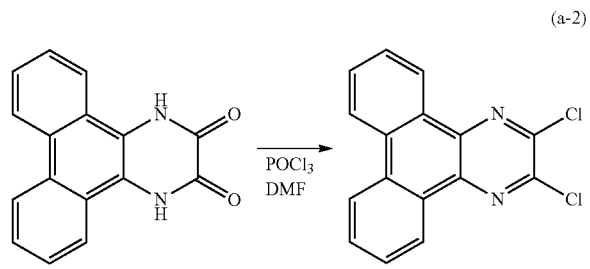

(a-2)

Step 3: Synthesis of 2-chloro-3-(5-chloro-2-methoxyphenyl)quinoxaline

Next, 1.85 g of 2,3-dichlorodibenzo[f,h]quinoxaline obtained in Step 2, 1.16 g of 5-chloro-2-methoxyphenylboronic acid, 0.66 g of sodium carbonate, 27 mL of ethylene glycol dimethyl ether (abbreviation: DME), and 27 mL of water were put into a three-neck flask equipped with a reflux pipe, and the air in the flask was replaced with nitrogen. The mixture was degassed by being stirred under reduced pressure, and then 0.48 g of tetrakis(triphenylphosphine)palladium(0) (abbreviation: Pd(PPh$_3$)$_4$) was added thereto. Stirring was performed at 100° C. for 20.5 hours to cause a reaction. After a predetermined time, water was added to the reaction solution, the solid obtained by suction filtration was dissolved in dichloromethane and filtered, and the filtrate was concentrated. The resulting solid was purified by silica gel column chromatography using a developing solvent in which the ratio of toluene to hexane was 1:2, so that 1.86 g of a target quinoxaline derivative (white powder) was obtained in a yield of 74%. A synthesis scheme of Step 3 is shown in (a-3) below.

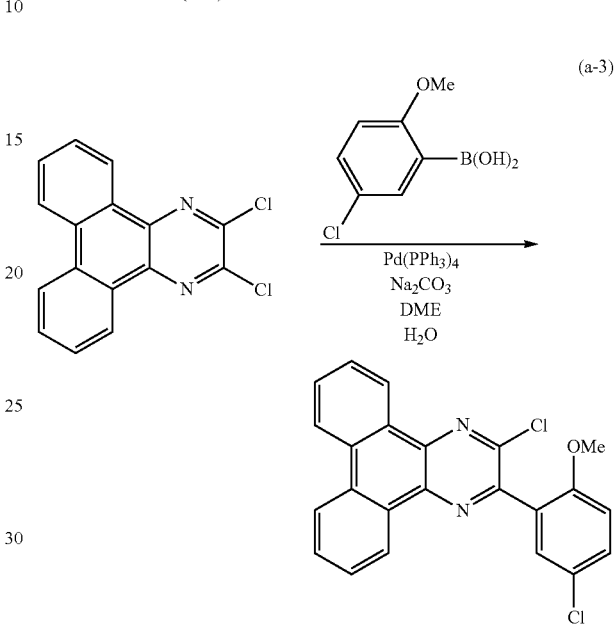

(a-3)

Step 4: Synthesis of 2-chloro-3-(5-chloro-2-hydroxyphenyl)quinoxaline

Next, 2.56 g of 2-chloro-3-(5-chloro-2-methoxyphenyl)quinoxaline obtained in Step 3 and 70 mL of dehydrated dichloromethane were put into a three-neck flask, and the air in the flask was replaced with nitrogen. After the flask was cooled down to −20° C., 13 mL of boron tribromide (1M dichloromethane solution) was dripped, and the resulting mixture was stirred at room temperature for 16 hours. After a predetermined time, water was added, and extraction was performed with dichloromethane. The resulting solid obtained by the extraction was purified by silica gel column chromatography using dichloromethane as a developing solvent, so that 2.12 g of a target quinoxaline derivative (yellow powder) was obtained in a yield of 84%. A synthesis scheme of Step 4 is shown in (a-4) below.

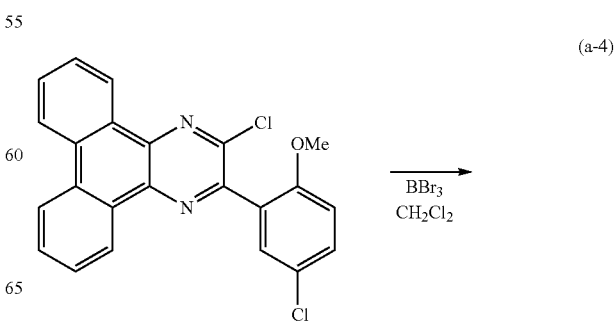

(a-4)

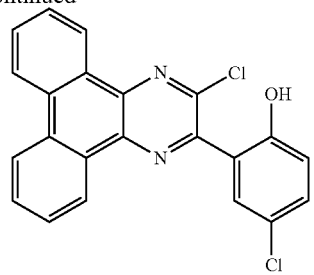

Step 5: Synthesis of 13-chlorodibenzo[f,h][1]benzofuro[2,3-b]quinoxaline

Then, 2.12 g of 2-chloro-3-(5-chloro-2-hydroxyphenyl)quinoxaline obtained in Step 4 and 27 mL of dehydrated N-methyl-2-pyrrolidone (abbreviation: NMP) were put into a three-neck flask equipped with a reflux pipe, and the air in the flask was replaced with nitrogen. After that, 1.51 g of potassium carbonate was added to the mixture, and the resulting mixture was stirred at 120° C. for 8 hours. After a predetermined time, water was added, and the resulting mixture was suction-filtered. The resulting solid was washed with ethanol, so that 1.56 g of a target quinoxaline derivative (pale yellow powder) was obtained in a yield of 84%. The synthesis scheme of Step 5 is shown in (a-5) below.

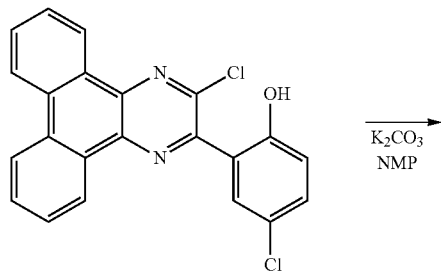

(a-5)

Step 6: Synthesis of 13-[3-(dibenzothiophen-4-yl)phenyl]dibenzo[f,h][1]benzofuro[2,3-b]quinoxaline (Abbreviation: 13mDBtPBfdbq)

Then, 0.78 g of 13-chlorodibenzo[f,h][1]benzofuro[2,3-b]quinoxaline obtained in Step 5, 1.10 g of (dibenzothiophen-4-yl)phenyl-3-boronic acid, 1.26 g of cesium fluoride, and 44 mL of mesitylene were put into a three-neck flask equipped with a reflux pipe, and the air in the flask was replaced with nitrogen. This mixture was degassed by being stirred under reduced pressure, 0.075 g of tris(dibenzylideneacetone)dipalladium(0) (abbreviation: Pd$_2$(dba)$_3$) and 0.059 g of 2'-(dicyclohexylphosphino)acetophenone ethylene ketal were added, and the resulting mixture was stirred at 120° C. for 17.5 hours. After a predetermined time, the obtained mixture to which ethanol was added was suction-filtered and was washed with water and ethanol. The resulting solid was dissolved in toluene, the mixture was filtered through a filter aid in which Celite, alumina, and Celite were stacked in this order, and the filtrate was concentrated and dried and then was recrystallized with toluene, so that 0.71 g of a target substance (yellowish white powder) was obtained in a yield of 56%. By a train sublimation method, 0.70 g of the obtained yellowish white powder was purified. In the purification by sublimation, the solid was heated at 330° C. under a pressure of 2.7 Pa with an argon gas flow rate of 10.5 mL/min. After the purification by sublimation, 0.56 g of a target yellowish white solid was obtained in a yield of 80%. A synthesis scheme of Step 6 is shown in (a-6) below.

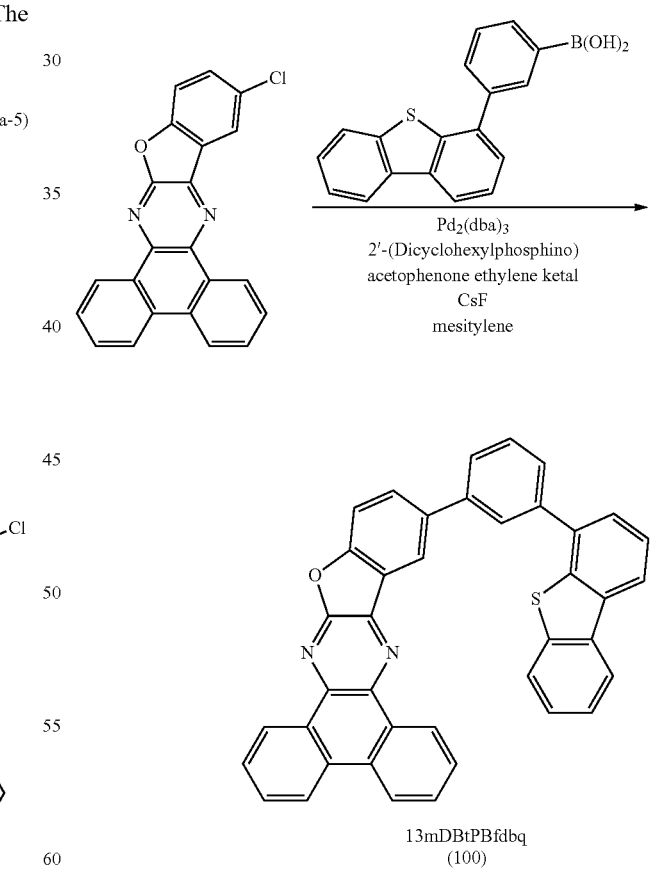

(a-6)

Analysis results by nuclear magnetic resonance spectroscopy ($^1$H-NMR) of the yellowish white solid obtained in Step 6 are shown below. A $^1$H-NMR chart is shown in FIG.

8. The results reveal that 13mDBtPBfdbq, the organic compound of one embodiment of the present invention represented by Structural Formula (100), was obtained in this example.

$^1$H-NMR δ (CDCl$_3$): 7.49-7.51 (m, 2H), 7.63-7.64 (m, 2H), 7.71 (t, 1H), 7.80-7.89 (m, 8H), 8.06 (d, 1H), 8.16 (s, 1H), 8.22-8.25 (m, 2H), 8.70-8.74 (m, 3H), 9.36 (d, 1H), 9.49-9.51 (m, 1H).

Then, the ultraviolet-visible absorption spectra (hereinafter, simply referred to as "absorption spectra") and emission spectra of 13mDBtPBfdbq in a toluene solution and a solid thin film of 13mDBtPBfdbq were measured.

Figure 9A:
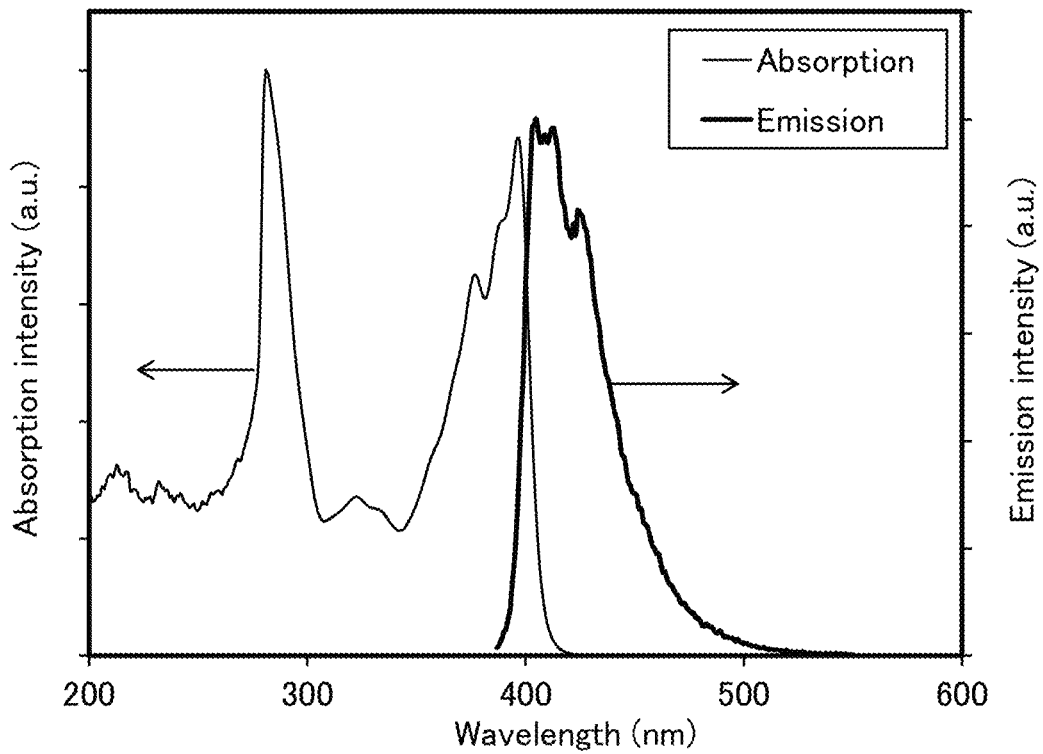
FIGS. 9A and 9B each show an ultraviolet-visible absorption spectrum and an emission spectrum of the organic compound represented by Structural Formula (100).

The absorption spectrum of 13mDBtPBfdbq in the toluene solution was measured using a UV-visible spectrophotometer (V550 type, manufactured by JASCO Corporation). The emission spectrum of 13mDBtPBfdbq in the toluene solution was measured with a fluorescence spectrophotometer (F S920, manufactured by Hamamatsu Photonics K.K.). FIG. 9A shows the obtained absorption and emission spectra of 13mDBtPBfdbq in the toluene solution. The horizontal axis represents wavelength and the vertical axes represent absorption intensity and emission intensity.

FIG. 9A shows that 13mDBtPBfdbq in the toluene solution has absorption peaks at around 281 nm and 397 nm, and an emission wavelength peak at around 405 nm (the excitation wavelength: 372 nm).

Figure 9B:
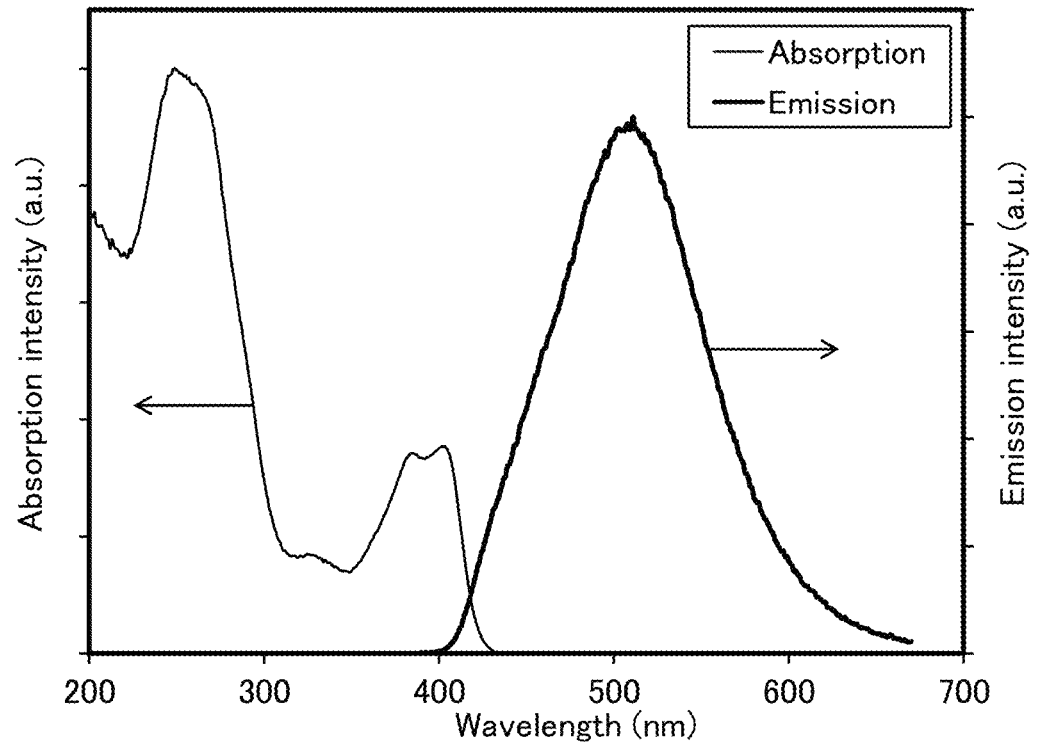

The solid thin film of 13mDBtPBfdbq was formed on a quartz substrate by a vacuum evaporation method and the absorption spectrum thereof was measured with a UV-visible spectrophotometer (U-4100, manufactured by Hitachi High-Technologies Corporation). The emission spectrum of the same solid thin film of 13mDBtPBfdbq was measured with a fluorescence spectrophotometer (FS920, manufactured by Hamamatsu Photonics K.K.). The obtained absorption and emission spectra of the solid thin film of 13mDBtPBfdbq are shown in FIG. 9B. The horizontal axis represents wavelength and the vertical axes represent absorption intensity and emission intensity.

FIG. 9B shows that the solid thin film of 13mDBtPBfdbq has absorption peaks at around 383 nm and 403 nm and an emission wavelength peak at around 511 nm (the excitation wavelength: 380 nm).

Differential scanning calorimetry was also performed on 13mDBtPBfdbq. For the calorimetry, a differential scanning calorimeter (Pyris 1, PerkinElmer Japan Co., Ltd.) was used. One cycle in the calorimetry was as follows: the temperature was increased from −10° C. to 350° C. at a rate of 40° C./min, kept at 350° C. for 1 minute, and decreased from 350° C. to −10° C. at a rate of 100° C./min. In this example, measurement of three cycles was performed. From the result at the rising temperature in the second cycle, it was found that the glass transition temperature ($T_g$) was 141° C. This indicates that 13mDBtPBfdbq synthesized in this example has significantly high heat resistance.

Example 2

Figure 10:
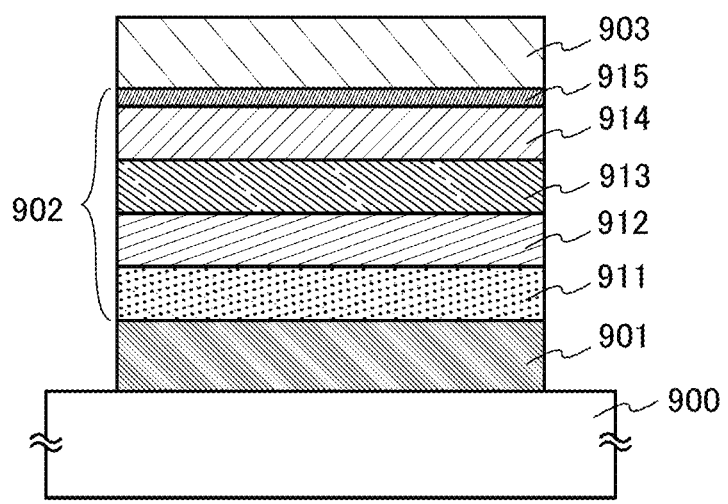
FIG. 10 illustrates a light-emitting element.
Figure 11:
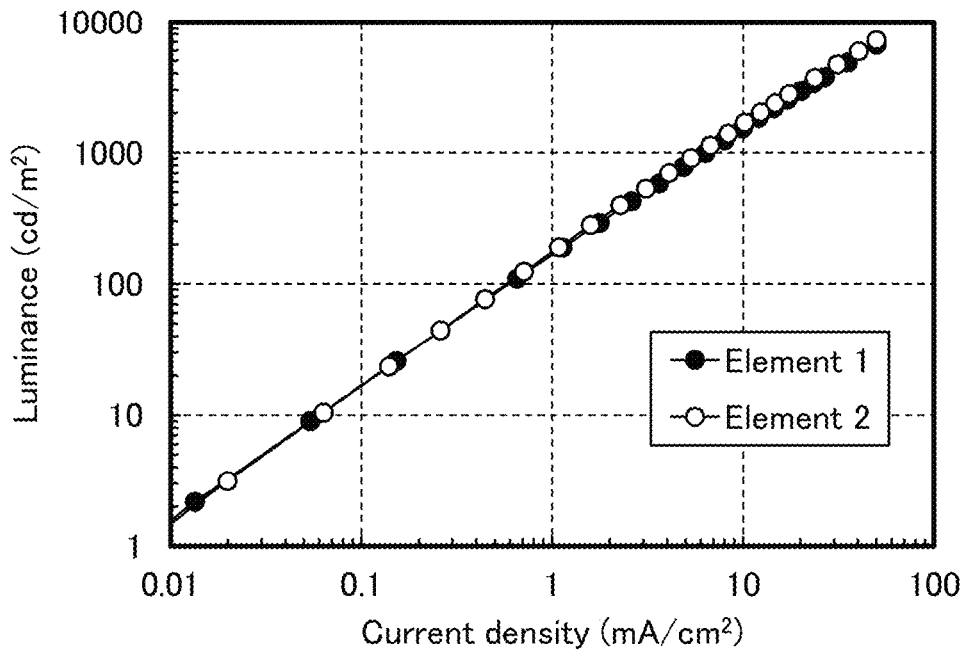
FIG. 11 shows the current density-luminance characteristics of Light-emitting Element 1 and Comparative Light-emitting Element 2.
Figure 12:
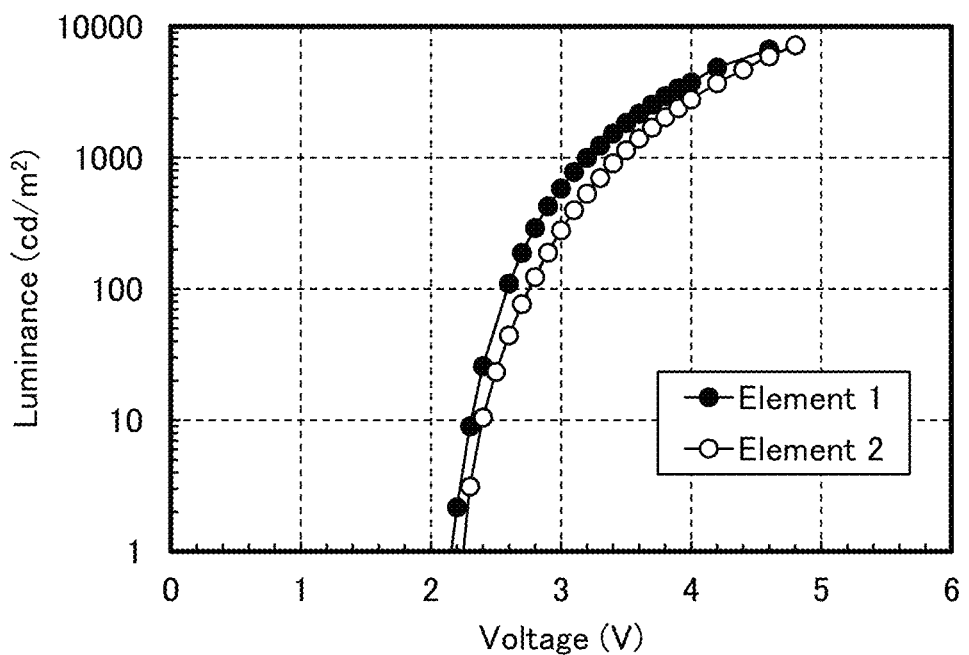
FIG. 12 shows the voltage-luminance characteristics of Light-emitting Element 1 and Comparative Light-emitting Element 2.
Figure 13:
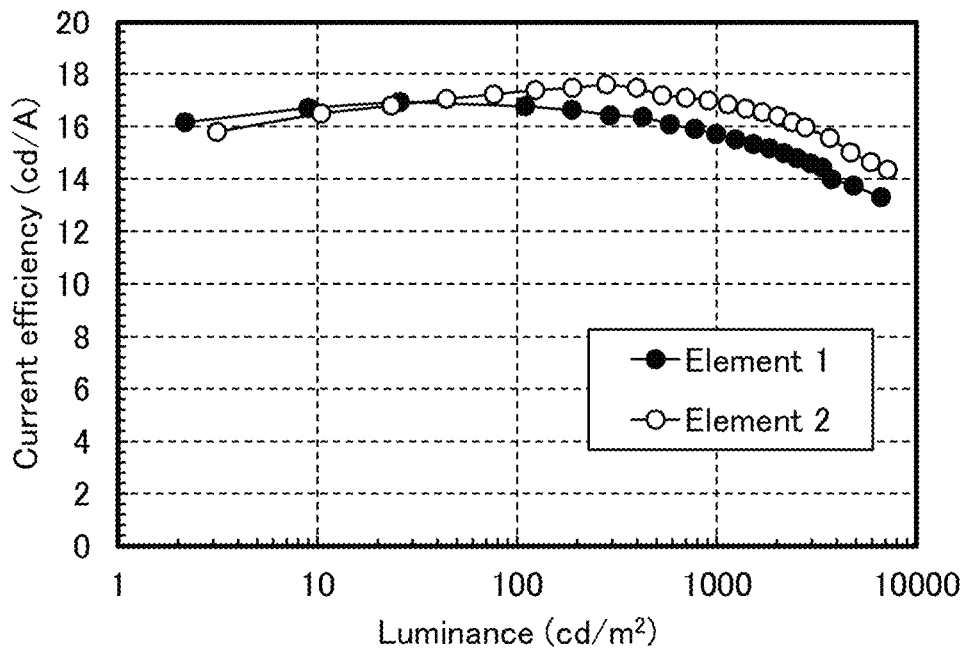
FIG. 13 shows the luminance-current efficiency characteristics of Light-emitting Element 1 and Comparative Light-emitting Element 2.
Figure 14:
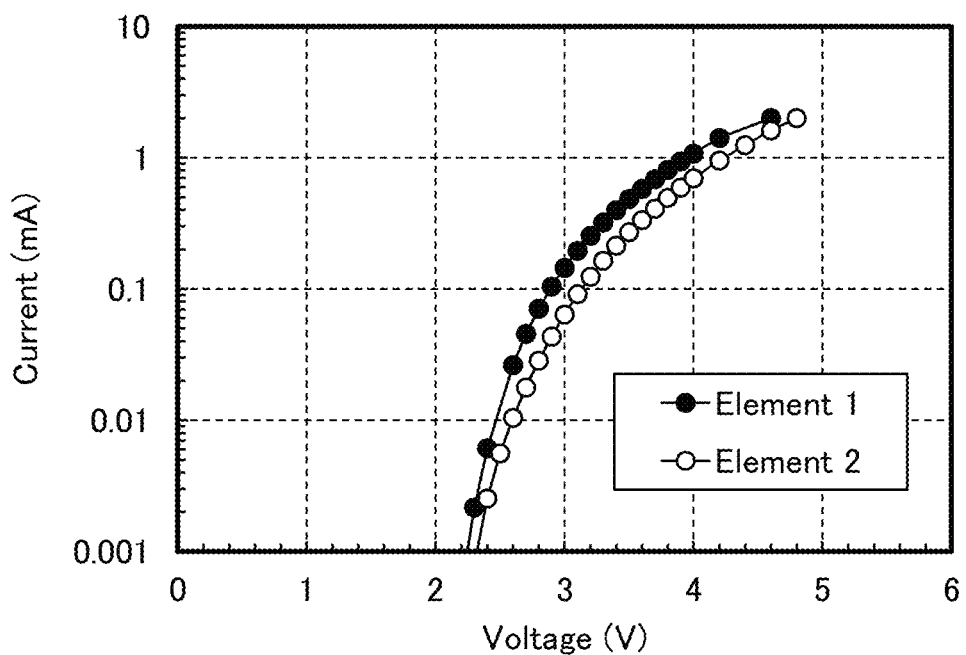
FIG. 14 shows the voltage-current characteristics of Light-emitting Element 1 and Comparative Light-emitting Element 2.

This example will describe element structures, fabrication methods, and characteristics of Light-emitting Element 1 (light-emitting element of one embodiment of the present invention) and Comparative Light-emitting Element 2. Light-emitting Element 1 uses for a light-emitting layer 13-[3-(dibenzothiophen-4-yl)phenyl]dibenzo[f,h][1]benzofuro[2,3-b]quinoxaline (abbreviation: 13mDBtPBfdbq) (Structural Formula (100)) described in Example 1. Comparative Light-emitting Element 2 uses for a light-emitting layer 2-[3-(3'-dibenzothiophen-4-yl)biphenyl]dibenzo[f,h]quinoxaline (abbreviation: 2mDBTBPDBq-II) (Structural Formula (200)). Note that FIG. 10 illustrates an element structure of the light-emitting elements used in this example, and Table 1 shows specific structures. The chemical formulae of materials used in this example are shown below.

TABLE 1

| | First electrode 901 | Hole-injection layer 911 | Hole-transport layer 912 | Light-emitting layer 913 | Electron-transport layer 914 | Electron-injection layer 915 | Second electrode 903 |
| --- | --- | --- | --- | --- | --- | --- | --- |
| Light-emitting Element 1 | ITSO (70 nm) | DBT3P-II:MoOx (2:1, 70 nm) | PCBBiLB P (20 nm) | * | mPCCzPTzn-02 (30 nm) | NBphen (15 nm) | LiF (1 nm) | Al (200 nm) |
| Comparative Light-emitting Element 2 | ITSO (70 nm) | DBT3P-II:MoOx (2:1, 70 nm) | PCBBiLB P (20 nm) | ** | mPCCzPTzn-02 (30 nm) | NBphen (15 nm) | LiF (1 nm) | Al (200 nm) |

* 13mDBtPBfdbq:PCBBiF:[Ir(dmpqn)$_2$(acac)] (0.75:0.25:0.1, 40 nm)
** 2mDBTBPDBq-II:PCBBiF:[Ir(dmpqn)$_2$(acac)] (0.75:0.25:0.1, 40 nm)

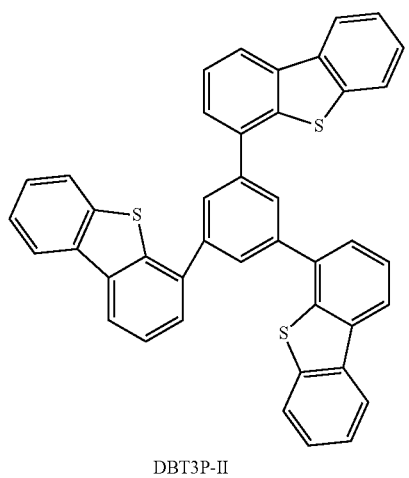

DBT3P-II

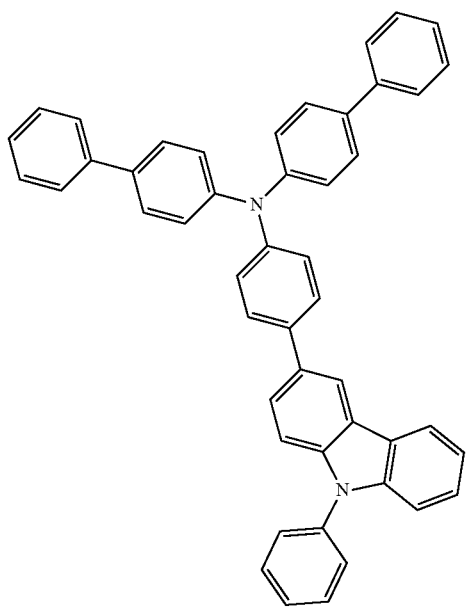
PCBBi1BP
(100)
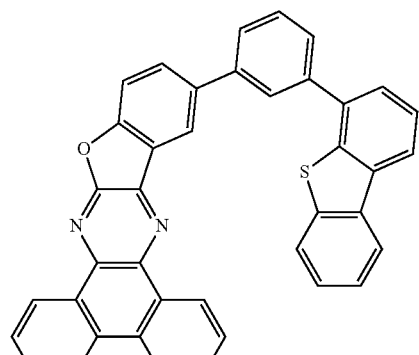
13mDBtPBfdbq
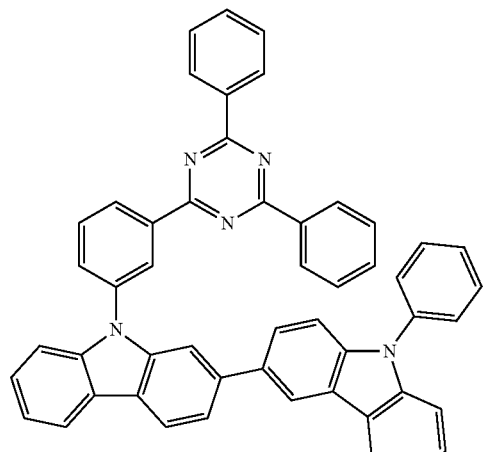
mPCCzPTzn-02
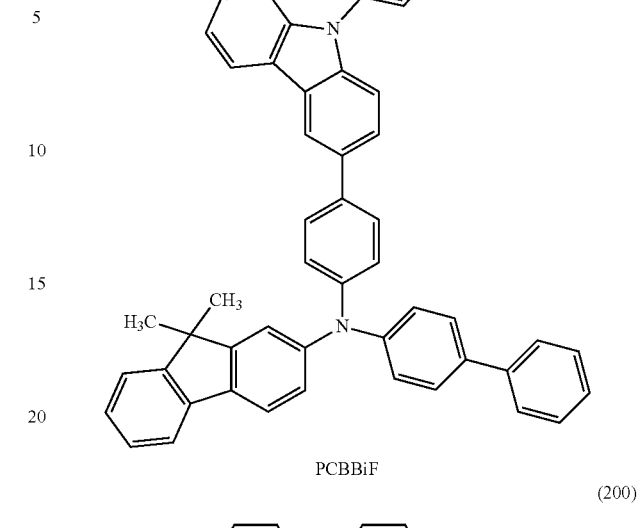
PCBBiF
(200)
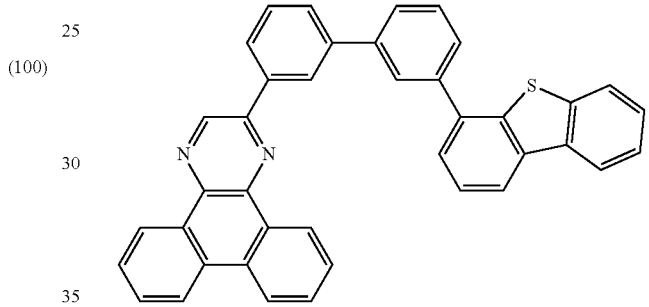
2mDBTBPDBq-II
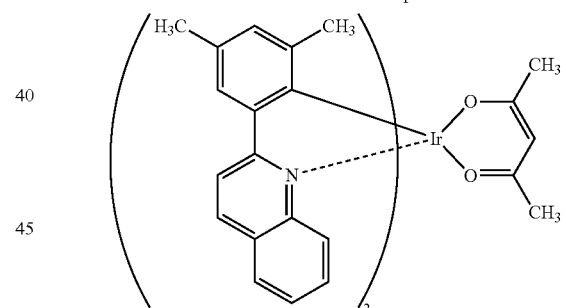
[Ir(dmpqn)$_2$(acac)]
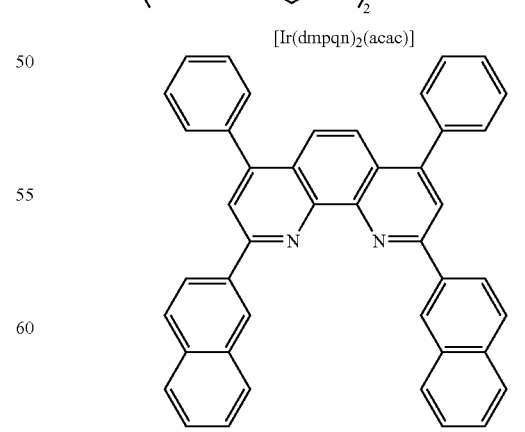
NBphen <<Fabrication of Light-Emitting Elements>>

In each of the light-emitting elements described in this example, as illustrated in FIG. 10, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $1×10^{-4}$ Pa, the hole-injection layer 911 was formed to a thickness of 70 nm by co-evaporation of 4,4',4''-(benzene-1,3,5-triyl)tri(dibenzothiophene) (abbreviation: DBT3P-II) and molybdenum oxide to have a mass ratio of 4,4',4''-(benzene-1,3,5-triyl)tri(dibenzothiophene) to molybdenum oxide of 2:1.

Then, the hole-transport layer 912 was formed over the hole-injection layer 911. The hole-transport layer 912 was formed to a thickness of 20 nm by evaporation of 4,4'-diphenyl-4''-(9-phenyl-9H-carbazol-3-yl)triphenylamine (abbreviation: PCBBi1BP).

Next, the light-emitting layer 913 was formed over the hole-transport layer 912.

The light-emitting layer 913 in Light-emitting Element 1 was formed to a thickness of a thickness of 40 nm by co-evaporation of the organic compound 13mDBtPBfdbq of one embodiment of the present invention as a host material, PCBBiF as an assist material, and bis[4,6-dimethyl-2-(2-quinolinyl-κN)phenyl-κC](2,4-pentanedionato-κ$^2$O,O')iridium(III) (abbreviation: [Ir(dmpqn)$_2$(acac)]) as a guest material (phosphorescent material) to have a weight ratio of 13mDBtPBfdbq to PCBBiF and [Ir(dmpqn)$_2$(acac)] of 0.75:0.25:0.1.

The light-emitting layer 913 in Comparative Light-emitting Element 2 was formed to a thickness of 40 nm by co-evaporation of 2mDBTBPDBq-II as a host material, PCBBiF as an assist material, and [Ir(dmpqn)$_2$(acac)] as a guest material (phosphorescent material) to have a weight ratio of 2mDBTBPDBq-II to PCBBiF and [Ir(dmpqn)$_2$(acac)] of 0.75:0.25:0.1.

Next, the electron-transport layer 914 was formed over the light-emitting layer 913. The electron-transport layer 914 was formed in the following manner: 9-[3-(4,6-diphenyl-1,3,5-triazin-2-yl)phenyl]-9'-phenyl-2,3'-bi-9H-carbazole (abbreviation: mPCCzPTzn-02) and 2,9-bis(naphthalen-2-yl)-4,7-diphenyl-1,10-phenanthroline (abbreviation: NBphen) were sequentially deposited by evaporation to thicknesses of 30 nm and 15 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 200 nm by evaporation of aluminum. In this example, the second electrode 903 functions as a cathode.

Through the above steps, the light-emitting elements each including an EL layer between a pair of electrodes were formed over the substrate 900. The hole-injection layer 911, the hole-transport layer 912, the light-emitting layer 913, the electron-transport layer 914, and the electron-injection layer 915 described above are functional layers forming the EL layer of one embodiment of the present invention. Furthermore, in all the evaporation steps in the above fabrication method, evaporation was performed by a resistance-heating method.

Each of the light-emitting elements fabricated as described above was sealed using another substrate (not illustrated) in such a manner that the substrate (not illustrated) with an ultraviolet curable sealant was fixed to the substrate 900 in a glove box containing a nitrogen atmosphere, and the substrates were bonded to each other with the sealant attached to the periphery of the light-emitting element formed over the substrate 900. At the time of the sealing, the sealant was irradiated with 365-nm ultraviolet light at 6 J/cm$^2$ to be solidified, and the sealant was heated at 80° C. for 1 hour to be stabilized.

<<Operation Characteristics of Light-Emitting Elements>>

Operation characteristics of the fabricated light-emitting elements were measured. Note that the measurement was performed at room temperature (in an atmosphere kept at 25° C.). FIGS. 11 to 14 show the measurement results.

Table 2 lists the initial values of main characteristics of the light-emitting elements at around 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting Element 1 | 3.2 | 0.25 | 6.3 | (0.68, 0.32) | 1000 | 16 | 15 | 19 |
| Comparative Light-emitting Element 2 | 3.4 | 0.21 | 5.3 | (0.68, 0.32) | 910 | 17 | 16 | 19 |

The above results show that Light-emitting Element 1 fabricated in this example has excellent current-voltage characteristics compared with Comparative Light-emitting Element 2. This is presumably because 13mDBtPBfdbq of one embodiment of the present invention used in the light-emitting layer of Light-emitting Element 1 has a deep LUMO level due to a structure where an oxygen-containing five-membered ring is fused. According to the cyclic voltammetry (CV) measurement results of reduction potentials, the LUMO level of 2mDBTBPDBq-II was −2.94 eV, while the LUMO level of 13mDBtPBfdbq was −3.17 eV.

Figure 15:
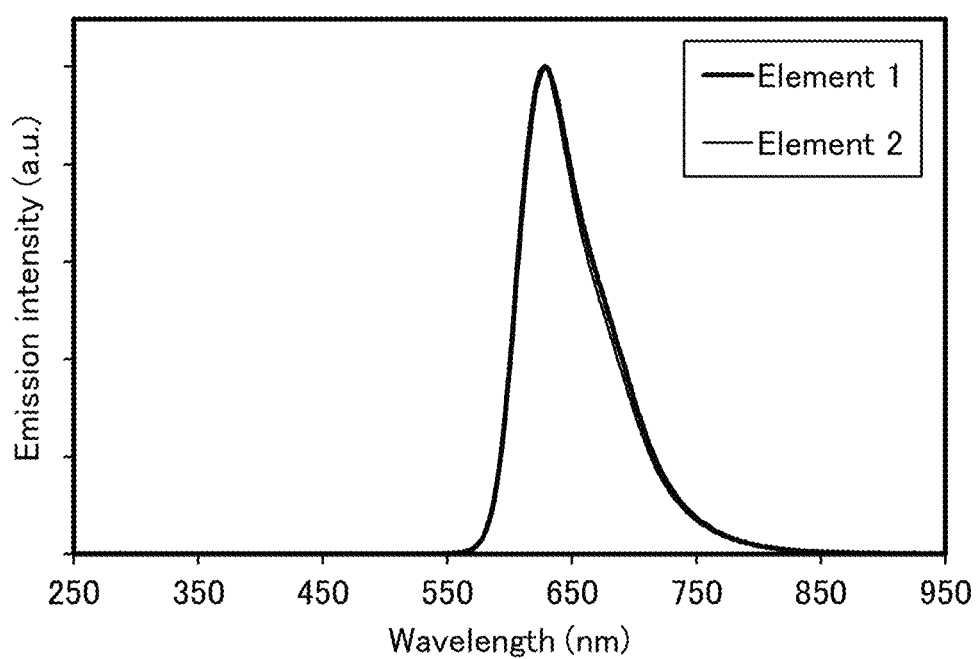
FIG. 15 shows the emission spectra of Light-emitting Element 1 and Comparative Light-emitting Element 2.

FIG. 15 shows emission spectra in the case where current with a density of 2.5 mA/cm² was supplied to Light-emitting Element 1 and Comparative Light-emitting Element 2. As shown in FIG. 15, the emission spectrum of each of Light-emitting Element 1 and Comparative Light-emitting Element 2 has a peak at around 628 nm probably derived from light emission of the organometallic complex [Ir(dmpqn)$_2$(acac)] contained in the light-emitting layer 913.

Figure 16:
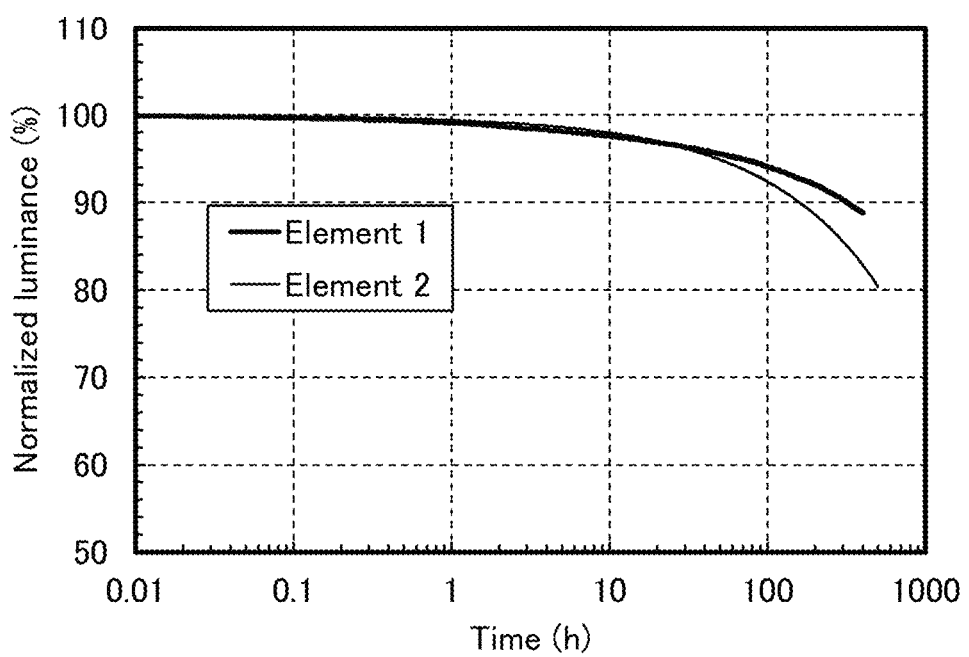
FIG. 16 shows the reliability of Light-emitting Element 1 and Comparative Light-emitting Element 2.

Next, reliability tests were performed on Light-emitting Element 1 and Comparative Light-emitting Element 2. FIG. 16 shows results of the reliability tests. In FIG. 16, the vertical axis represents normalized luminance (%) with an initial luminance of 100%, and the horizontal axis represents driving time (h) of the elements.

In the reliability tests, the light-emitting elements were driven at a current density of 75 mA/cm².

The results of the reliability tests show that Light-emitting Element 1 has higher reliability than Comparative Light-emitting Element 2. This is probably due to the use of the organic compound 13mDBtPBfdbq (Structural Formula (100)) of one embodiment of the present invention in the light-emitting layer of Light-emitting Element 1. Since 13mDBtPBfdbq has a structure where an oxygen-containing five-membered ring is fused to the 2- and 3-positions of a dibenzoquinoxaline skeleton as described in Embodiment 1, unlike in 2mDBTBPDBq-II (Structural Formula: 200), steric repulsion between a substituted phenylene group at the 2-position of the dibenzoquinoxaline skeleton and hydrogen at the 3-position does not make the substituted phenylene group twist, resulting in improvements in robustness and stability of molecules. The excellent current-voltage characteristics of Light-emitting Element 1 compared with Comparative Light-emitting Element 2, which are shown in Table 2, suggest that Light-emitting Element 1 has a narrow carrier recombination region in the light-emitting layer and an element structure that easily causes local deterioration. The reason why Light-emitting Element 1 has high reliability as shown in FIG. 16 is that the organic compound of one embodiment of the present invention has a negligible steric hindrance and is highly robust and stable. That is, the organic compound of one embodiment of the present invention is a material overcoming the tradeoff between a low drive voltage and high reliability, which is often caused in a light-emitting element.

Furthermore, the organic compound 13mDBtPBfdbq of one embodiment of the present invention has not only the aforementioned molecular structure to increase reliability but also an oxygen-containing five-membered ring-fused structure to minimize a decrease in the T1 level, which is caused by a fused polycyclic molecular structure. Specifically, the T1 levels of 2mDBTBPDBq-II and 13mDBtPBfdbq were estimated assuming that they correspond to peaks on the short wavelength side of the phosphorescence spectra observed at a temperature of liquid nitrogen (77 K); the T1 level of 2mDBTBPDBq-II was 515 nm and the T1 level of 13mDBtPBfdbq was 538 nm. Thus, a shift in the long wavelength side of the Ti level was only approximately 20 nm. Therefore, the use of the organic compound 13mDBtPBfdbq (Structural Formula (100)) of one embodiment of the present invention in the EL layer of a light-emitting element is effective in terms of maintaining the T1 level to a certain degree as well as increasing the reliability of the light-emitting element.

Example 3

Synthesis Example 2

This example will describe a method for synthesizing 13-[3-(dibenzofuran-4-yl)phenyl]dibenzo[f,h][1]benzofuro[2,3-b]quinoxaline (abbreviation: 13mDBfPBfdbq), the organic compound of one embodiment of the present invention represented by Structural Formula (101) in Embodiment 1. The structure of 13mDBfPBfdbq is shown below.

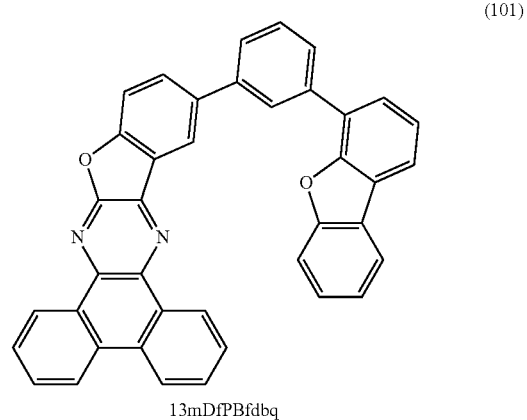 [SMILES: c1cc(-c2ccc3oc4nc5c6ccccc6c6ccccc6c5nc4c3c2)cc(-c2cccc3c2oc2ccccc23)c1]

<Synthesis of 13mDBfPBfdbq>

13mDBfPBfdbq described in this example is synthesized by the method shown in Synthesis Scheme (b-1) below as in the synthesis method of 13mDBtPBfdbq described in Example 1.

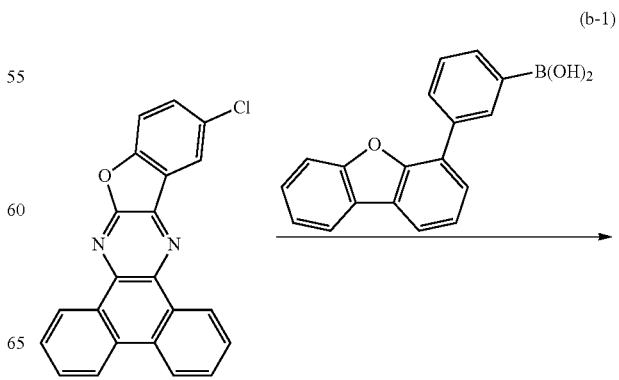

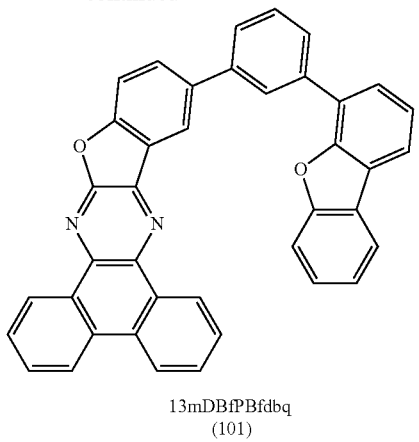

13mDBfPBfdbq
(101)

Thus, the organic compound 13mDBfPBfdbq of one embodiment of the present invention can be obtained.

Example 4

Synthesis Example 3

This example will describe a method for synthesizing 13-[3-(9H-carbazol-9-yl)phenyl]dibenzo[f,h][1]benzofuro[2,3-b]quinoxaline (abbreviation: 13mCzPBfdbq), the organic compound of one embodiment of the present invention represented by Structural Formula (102) in Embodiment 1. The structure of 13mCzPBfdbq is shown below.

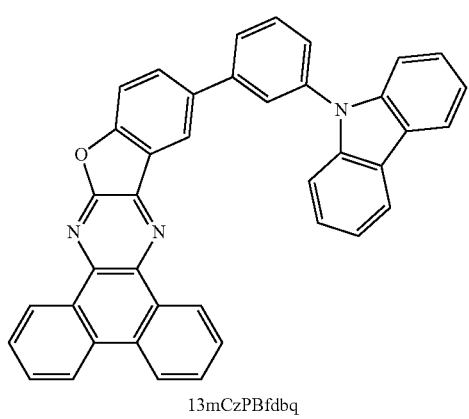

13mCzPBfdbq
(102)

<Synthesis of 13mCzPBfdbq>

13mCzPBfdbq in this example is synthesized by the method shown in Synthesis Scheme (c-1) below as in the synthesis method of 13mDBtPBfdbq described in Example 1.

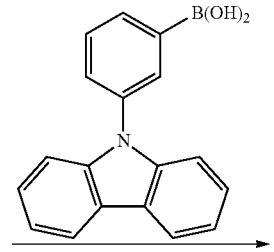

(c-1)

13mCzPBfdbq
(102)

Thus, the organic compound 13mCzPBfdbq of one embodiment of the present invention can be obtained.

Example 5

Synthesis Example 4

This example will describe a method for synthesizing 13-[3-(triphenylen-2-yl)phenyl]dibenzo[f,h][1]benzofuro[2,3-b]quinoxaline (abbreviation: 13mTpPBfdbq), the organic compound of one embodiment of the present invention represented by Structural Formula (110) in Embodiment 1. The structure of 13mTpPBfdbq is shown below.

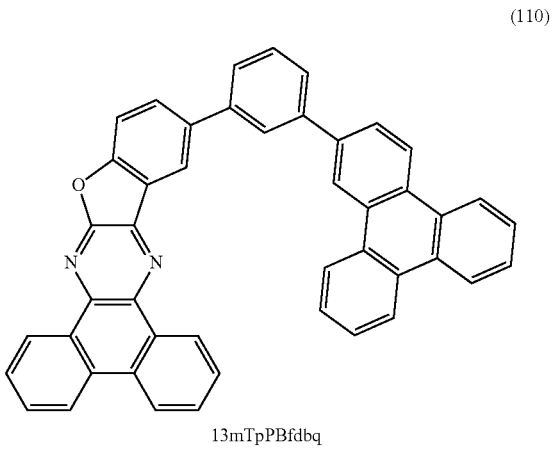 [SMILES: c1cc(-c2ccc3c4ccccc4c4ccccc4c3c2)cc(-c2ccc3oc4nc5c6ccccc6c6ccccc6c5nc4c3c2)c1]

(110)

13mTpPBfdbq

<Synthesis of 13mTpPBfdbq>

13mTpPBfdbq described in this example is synthesized by the method shown in Synthesis Scheme (d-1) below as in the synthesis method of 13mDBtPBfdbq described in Example 1.

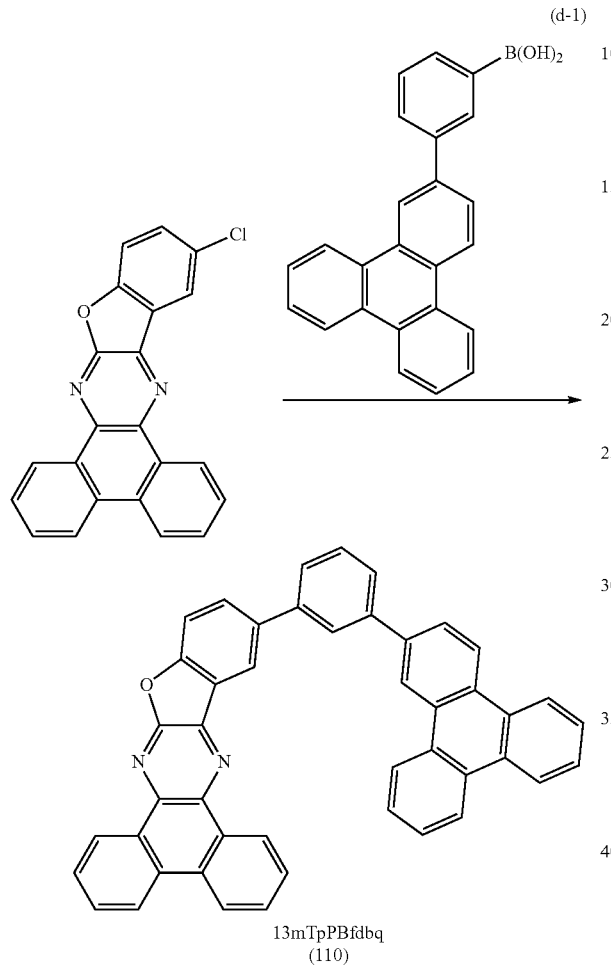

Thus, the organic compound 13mTpPBfdbq of one embodiment of the present invention can be obtained.

Example 6

Synthesis Example 5

This example will describe a method for synthesizing 13-[3-(9'-phenyl-3,3'-bi-9H-carbazol-9-yl)phenyl]dibenzo[f,h][1]benzofuro[2,3-b]quinoxaline (abbreviation: 13mPCCzPBfdbq), the organic compound of one embodiment of the present invention represented by Structural Formula (123) in Embodiment 1. The structure of 13mPCCzPBfdbq is shown below.

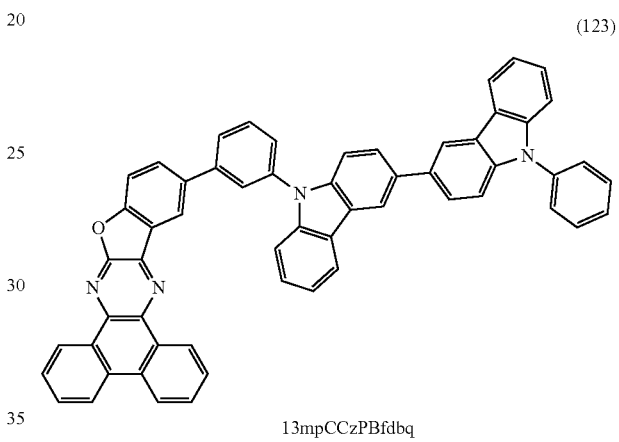

<Synthesis of 13mPCCzPBfdbq>

13mPCCzPBfdbq described in this example is synthesized by the method shown in Synthesis Scheme (e-1) below as in the synthesis method of 13mDBtPBfdbq described in Example 1.

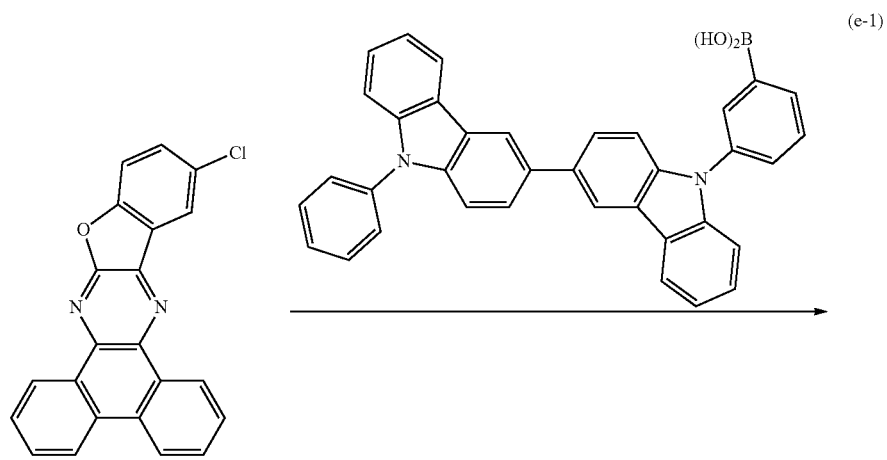

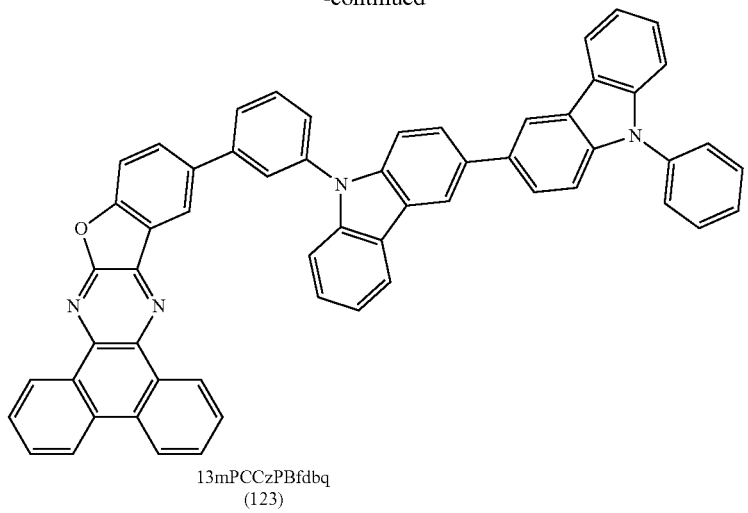

13mPCCzPBfdbq
(123)

Thus, the organic compound 13mPCCzPBfdbq of one embodiment of the present invention can be obtained.

Example 7

Synthesis Example 6

This example will describe a method for synthesizing 13-(9'-phenyl-3,3'-bi-9H-carbazol-9-yl)dibenzo[f,h][1]benzofuro[2,3-b]quinoxaline (abbreviation: 13PCCzBfdbq), the organic compound of one embodiment of the present invention represented by Structural Formula (125) in Embodiment 1. The structure of 13PCCzBfdbq is shown below.

(125)

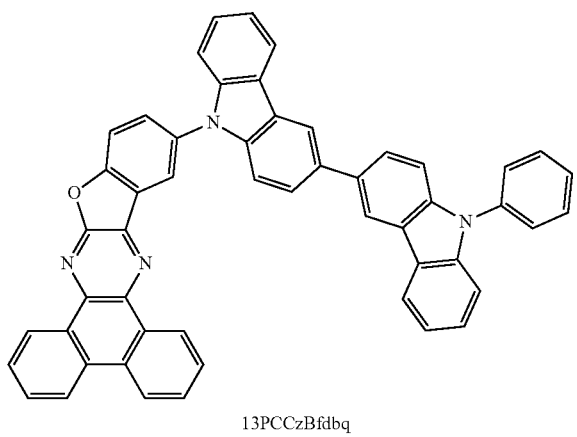

13PCCzBfdbq

<Synthesis of 13PCCzBfdbq>

Next, 0.78 g of 13-chlorodibenzo[f,h][1]benzofuro[2,3-b]quinoxaline obtained in Step 5 in Example 1, 0.90 g of 9'-phenyl-3,3'-bi-9H-carbazole, and 22 mL of mesitylene were put into a three-neck flask equipped with a reflux pipe, and the air in the flask was replaced with nitrogen. The mixture in the flask was degassed by being stirred under reduced pressure, and then, 0.42 g of sodium tert-butoxide, 0.013 g of bis(dibenzylideneacetone)palladium(0) (abbreviation: $Pd(dba)_2$), and 0.018 g of 2-dicyclohexylphosphino-2',6'-dimethoxybiphenyl (abbreviation: S-Phos) were added thereto. The resulting mixture was stirred at 150° C. for 13 hours.

After a predetermined time, the obtained mixture to which ethanol was added was subjected to suction filtration and was washed with water and ethanol. Then, purification by silica gel column chromatography using toluene as a developing solvent was performed, so that 0.56 g of a target substance (yellow solid) was obtained in a yield of 35%. The synthesis scheme of the above synthesis method described in this example is shown in (f-1) below.

(f-1)

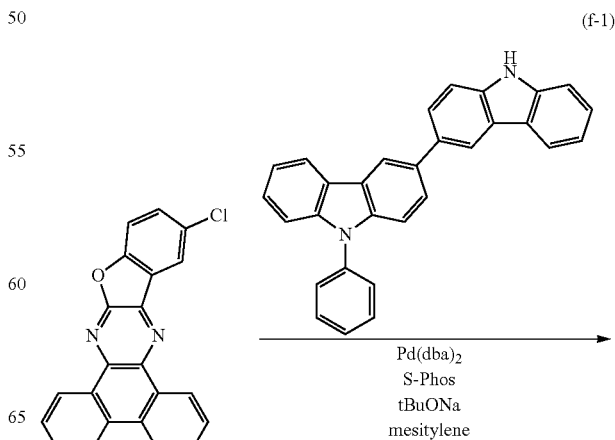

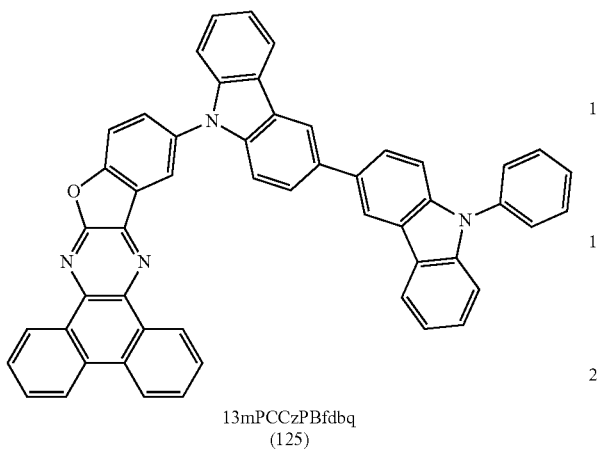

13mPCCzPBfdbq
(125)

Figure 17:
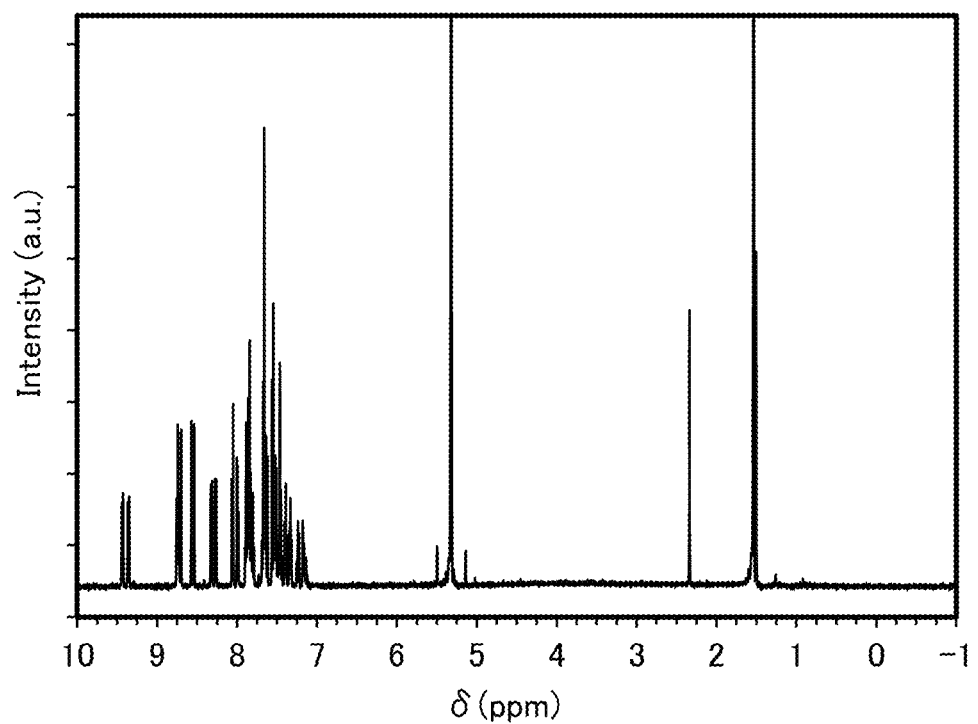
FIG. 17 shows a $^1$H-NMR chart of an organic compound represented by Structural Formula (125).

Analysis results by nuclear magnetic resonance ($^1$H-NMR) spectroscopy of the yellow solid obtained above are shown below. FIG. 17 is the $^1$H-NMR chart. The results reveal that 13PCCzBfdbq, the organic compound of one embodiment of the present invention represented by Structural Formula (125), was obtained in this example.

$^1$H-NMR. δ (CDCl$_3$): 7.33 (t, 1H), 7.39 (t, 1H), 7.45-7.56 (m, 6H), 7.62-7.69 (m, 5H), 7.79-7.90 (m, 6H), 7.95 (d, 1H), 8.06 (d, 1H), 8.27 (d, 1H), 8.32 (d, 1H), 8.56 (d, 2H), 8.70-8.76 (m, 3H), 9.36 (d, 1H), 9.44 (d, 1H).

This application is based on Japanese Patent Application Serial No. 2018-007073 filed with Japan Patent Office on Jan. 19, 2018, the entire contents of which are hereby incorporated by reference.

What is claimed is:

1. A light-emitting element comprising:
   a first electrode;
   a hole-transport layer over the first electrode;
   a light-emitting layer over the hole-transport layer; and
   a second electrode over the light-emitting layer,
   wherein the light-emitting layer comprises an organic compound and a substance that converts triplet excitation energy into light emission,
   wherein the organic compound is represented by Formula (G1):

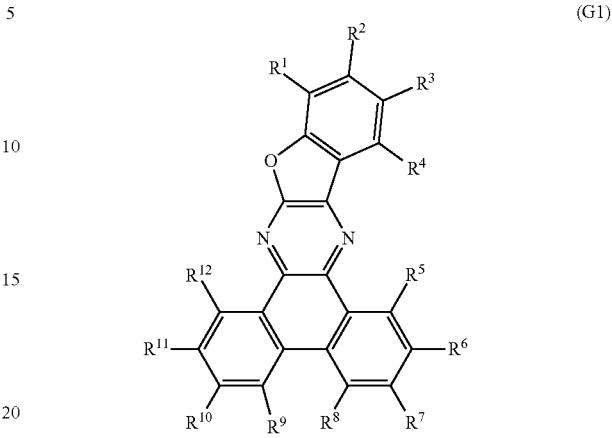

(G1)

wherein Q represents O or S, wherein at least one of $R^1$ to $R^{12}$ represents a first group which comprises a substituted or unsubstituted condensed aromatic ring or condensed heteroaromatic ring having 10 to 30 carbon atoms, wherein when a substituted or unsubstituted carbazole skeleton is directly bonded to the dibenzobenzofuroquinoxaline or dibenzobenzothienoquinoxaline skeleton as the substituted or unsubstituted condensed heteroaromatic ring having 10 to 30 carbon atoms, a nitrogen atom of the substituted or unsubstituted carbazole skeleton is bonded to the dibenzobenzofuroquinoxaline or dibenzobenzothienoquinoxaline skeleton, and wherein each of the others of $R^1$ to $R^{12}$ independently represents any one of hydrogen, a halogeno group, a hydroxy group, an amino group, a nitro group, and a group having 1 to 50 carbon atoms.

2. The light-emitting element according to claim 1, wherein the substance that converts triplet excitation energy into light emission is a phosphorescent material or a thermally activated delayed fluorescence material.

3. The light-emitting element according to claim 1, wherein the hole-transport layer comprises a r-electron rich heteroaromatic compound or a compound having an aromatic amine skeleton.

4. The light-emitting element according to claim 1, wherein the first group has a hole-transport property higher than an electron-transport property.

5. The light-emitting element according to claim 1, wherein the first group comprises any one of a fluorene skeleton, a phenanthrene skeleton, a triphenylene skeleton, a naphthalene skeleton, a dibenzothiophene skeleton, a dibenzofuran skeleton, and a carbazole skeleton.

6. A light-emitting element comprising:
   a first electrode;
   a hole-transport layer over the first electrode;
   a light-emitting layer over the hole-transport layer; and
   a second electrode over the light-emitting layer,
   wherein the light-emitting layer comprises an organic compound and a substance that converts triplet excitation energy into light emission, wherein the organic compound is represented by Formula (G1):

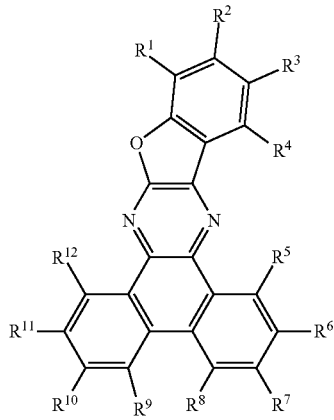

(G1)

wherein Q represents O or S,
wherein $R^3$ represents a first group comprising a substituted or unsubstituted condensed aromatic ring or condensed heteroaromatic ring having 10 to 30 carbon atoms,
wherein when a substituted or unsubstituted carbazole skeleton is directly bonded to the dibenzobenzofuroquinoxaline or dibenzobenzothienoquinoxaline skeleton as the substituted or unsubstituted condensed heteroaromatic ring having 10 to 30 carbon atoms, a nitrogen atom of the substituted or unsubstituted carbazole skeleton is bonded to the dibenzobenzofuroquinoxaline or dibenzobenzothienoquinoxaline skeleton, and
wherein each of $R^1$, $R^2$, and $R^4$ to $R^{12}$ independently represents any one of hydrogen, a halogeno group, a hydroxy group, an amino group, a nitro group, and a group having 1 to 50 carbon atoms.

7. The light-emitting element according to claim 6, wherein the substance that converts triplet excitation energy into light emission is a phosphorescent material or a thermally activated delayed fluorescence material.

8. The light-emitting element according to claim 6, wherein the hole-transport layer comprises a π-electron rich heteroaromatic compound or a compound having an aromatic amine skeleton.

9. The light-emitting element according to claim 6, wherein the first group has a hole-transport property higher than an electron-transport property.

10. The light-emitting element according to claim 6, wherein the first group comprises any one of a fluorene skeleton, a phenanthrene skeleton, a triphenylene skeleton, a naphthalene skeleton, a dibenzothiophene skeleton, a dibenzofuran skeleton, and a carbazole skeleton.

11. A light-emitting element comprising:
a first electrode;
a light-emitting layer over the first electrode; and
a second electrode over the light-emitting layer,
wherein the light-emitting layer comprises an organic compound and a thermally activated delayed fluorescence material,
wherein the organic compound is represented by Formula (G1):

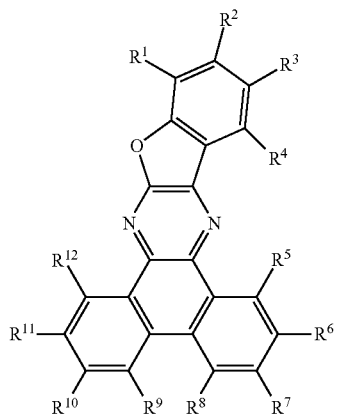

(G1)

wherein Q represents O or S,
wherein $R^3$ represents a first group comprising a substituted or unsubstituted condensed aromatic ring or condensed heteroaromatic ring having 10 to 30 carbon atoms,
wherein each of $R^1$, $R^2$, and $R^4$ to $R^{12}$ independently represents any one of hydrogen, a halogeno group, a hydroxy group, an amino group, a nitro group, and a group having 1 to 50 carbon atoms, and
wherein the substituted or unsubstituted condensed aromatic ring or condensed heteroaromatic ring having 10 to 30 carbon atoms is bonded to the dibenzobenzofuroquinoxaline or dibenzobenzothienoquinoxaline skeleton through a substituted or unsubstituted arylene group having 6 to 24 carbon atoms.

12. The light-emitting element according to claim 11, wherein the first group comprises any one of a fluorene skeleton, a phenanthrene skeleton, a triphenylene skeleton, a naphthalene skeleton, a dibenzothiophene skeleton, a dibenzofuran skeleton, and a carbazole skeleton.

13. The light-emitting element according to claim 1, wherein the substituted or unsubstituted condensed aromatic ring or condensed heteroaromatic ring having 10 to 30 carbon atoms is bonded to the dibenzobenzofuroquinoxaline or dibenzobenzothienoquinoxaline skeleton through a substituted or unsubstituted arylene group having 6 to 24 carbon atoms.

14. The light-emitting element according to claim 6, wherein the substituted or unsubstituted condensed aromatic ring or condensed heteroaromatic ring having 10 to 30 carbon atoms is bonded to the dibenzobenzofuroquinoxaline or dibenzobenzothienoquinoxaline skeleton through a substituted or unsubstituted arylene group having 6 to 24 carbon atoms.

* * * * *